US006646149B1

(12) United States Patent
Vermeulin et al.

(10) Patent No.: US 6,646,149 B1
(45) Date of Patent: Nov. 11, 2003

(54) POLYAMINE ANALOGUES AS THERAPEUTIC AND DIAGNOSTIC AGENTS

(76) Inventors: Nicolaas M. J. Vermeulin, 19334 - 196th Ave., NE., Woodinville, WA (US) 98072; Christine L. O'Day, 4404-B 216th St., SW., Mountlake Terrace, WA (US) 98043; Heather K. Webb, 5705 Seaview Ave., NW., Seattle, WA (US) 98107; Mark R. Burns, 226 NW. 184th St., Shoreline, WA (US) 98177; Donald E. Bergstrom, 3416 Hamilton St., West Lafayette, IN (US) 47906

( * ) Notice: Subject to any disclaimer, the term of this patent is extended or adjusted under 35 U.S.C. 154(b) by 0 days.

(21) Appl. No.: 09/584,175

(22) Filed: May 31, 2000

Related U.S. Application Data

(63) Continuation-in-part of application No. 09/396,523, filed on Sep. 15, 1999, which is a continuation-in-part of application No. 09/341,400, filed as application No. PCT/US98/14896 on Jul. 15, 1998, now Pat. No. 6,172,261.
(60) Provisional application No. 60/085,538, filed on May 15, 1998, provisional application No. 60/065,728, filed on Nov. 14, 1997, and provisional application No. 60/052,586, filed on Jul. 15, 1997.

(51) Int. Cl.[7] .................... C07C 271/12; A61K 31/27
(52) U.S. Cl. .................... 560/25; 549/65; 549/560; 564/83; 564/84; 564/215; 514/269; 514/270; 514/290; 514/299; 514/354; 514/361; 514/378; 514/445; 514/468; 514/478; 514/520; 514/561; 514/602; 514/616; 514/629; 514/673; 514/674; 544/300; 546/101; 546/152; 548/127; 548/248; 548/537; 558/411
(58) Field of Search .................... 560/25; 564/215, 564/83, 84, 511; 514/478, 616, 602, 673, 674, 269, 270, 290, 299, 354, 561, 378, 445, 668, 520, 629; 544/300; 546/101, 152; 548/248, 127, 537; 549/65, 460; 558/411

(56) References Cited

U.S. PATENT DOCUMENTS

| | | | |
|---|---|---|---|
| 4,309,442 A | | 1/1982 | Bey et al. |
| 4,590,288 A | * | 5/1986 | Klemann .................... 556/112 |
| 4,774,339 A | | 9/1988 | Haugland et al. |
| 4,818,770 A | | 4/1989 | Weinstein et al. |
| 4,950,744 A | * | 8/1990 | Dattagupta et al. ........... 536/27 |
| 5,187,288 A | | 2/1993 | Kang et al. |
| 5,248,782 A | | 9/1993 | Haugland et al. |
| 5,252,714 A | | 10/1993 | Harris et al. |
| 5,274,113 A | | 12/1993 | Kang et al. |
| 5,433,896 A | | 7/1995 | Kang et al. |
| 5,451,663 A | | 9/1995 | Kang et al. |
| 5,656,671 A | | 8/1997 | Bergeron, Jr. |

FOREIGN PATENT DOCUMENTS

| | | |
|---|---|---|
| WO | WO 8502769 A | 7/1985 |
| WO | WO 9214709 A | 9/1992 |
| WO | WO 9521612 A | 8/1995 |
| WO | WO 9622962 A | 8/1996 |
| WO | WO 9638464 A | 12/1996 |

OTHER PUBLICATIONS

Albanese, L., et al., "Investigations of the Mechanisms by which Mammalian Cell Growth Is Inhibited by $N^1N^{12}$–Bis(ethyl)spermine," Biochem. J., (1993) 291:131–7.

Alhonen–Hongisto, L. et al. (1980. "Intracellular Putrescine Deprivation Induces Uptake of the Natural Polyamines and Methylglyoxal Bis(Guanylhydrazone)," Biochem J 192:941–945.

Alhohen–Hongisto, L. et al. (1985). "Tumourigenicity, Cell–Surface Glycoprotein Changes and Ornithine Decarboxylase Gene Pattern in Ehrlich Ascites–Carcinoma Cells," Biochem J 229:711–715.

Aramaki, Y. et al. (1986). "Chemical Characterization of Spider Toxin, JSTX," Proc Japan Acad 62, Ser.B:359–362.

Asami, T. et al. (1989). "Acylpolyamines Mimic the Action of Joro Spider Toxin (JSTX) on Crustacean Muscle Glutamate Receptors," Biomedical Res 10:185–189.

Ask, A., et al., "Increased Survival of L1210 Leukemic Mice by Prevention of the Utilization of Extracellular Polyamines. Studies Using a Polyamine–Uptake Mutant, Antibiotics and a Polyamine–Deficient Diet," Cancer Lett., (1992) 66:29–34.

Baguley, B.C., "DNA Intercalating Anti–Tumour Agents," Anti–Cancer Drug Design, (1991)6:1–35.

Balasundaram, D., et al., "Polyamine—DNA Nexus: Structural Ramifications and Biological Implications," Mol. Cell. Biol., (1991) 100:129–40.

Bardocz, S. et al. (1993) "Polyamines in food; Implications for Growth and Health," J Biochem Nutr 4:66–71.

Bergeron, R. J., et al., "Antiproliferative Properties of Polyamine Analogues: A Structure—Activity Study," J. Med. Chem., (1994) 37:3464–76.

Bergeron, R. J., et al., "*Reagents for the Stepwise Functionalization of Spermine,*" J. Org. Chem., (1988) 53:3108–11.

Bergeron, R. J., et al., "Total Synthesis of (±)–15–Deoxyspergualin," J. Org. Chem., (1987) 52:1700–3.

Bergeron, R.J., et al., "A Comparison of Structure—Activity Relationships between Spermidine and Spermine Analogue Antineoplastics," J. Med. Chem., (1997) 40:1475–94.

Bhaskar Kanth, J. V., et al., "Selective Reduction of Carboxylic Acids into Alcohols Using $NaBH_4$ and $I_2$," J. Org. Chem., (1991) 56:5964–5.

(List continued on next page.)

Primary Examiner—Shailendra Kumar
(74) Attorney, Agent, or Firm—Burton A. Amernick; Connolly Bove Lodge & Hutz, LLP

(57) ABSTRACT

Novel "bispolyamine" inhibitor compounds of polyamine transport are disclosed. These compounds are useful pharmaceutical agents for treating diseases where it is desired to inhibit polyamine transport or other polyamine binding proteins, for example cancer and post-angioplasty injury. These compounds display desirable activities both for diagnostic and research assays and therapy.

28 Claims, 59 Drawing Sheets

OTHER PUBLICATIONS

Blagbrough, I. S., et al., "Practical Synthesis of the Putative Polyamine Spider Toxin FTX: a Proposed Blocker of Voltage–Sensitive Calcium Channels," Tetrahedron Lett., (1994) 35(13):2057–60.

Blagbrough, I.S. et al. (1998). "Practical Synthesis of Unsymmetrical Polyamine Amides," *Tetrahedron Lett* 39:439–442.

Bogle, R.G. et al. (1994). "Endothelial Polyamine Uptake: Selective Stimulation by L–arginine Deprivation," *Am J Physiol* 266:C776–C783.

Booth, R.J., et al., "Polymer–Supported Quenching Reagents for Parallel Purification," J. Am. Chem. Soc., (1997) 119:4882–6.

Borch, R.F., et al., "The Cyanohydridoborate Anion as a Selective Reducing Agent," J. Am. Chem. Soc., (1971) 93(12):2897–2904.

Brand, G., et al., *Cyclopolyamines:Synthesis of Cyclospermidines and Cyclospermines, Analogues of Spermidine and Spermine*, Tetrahedron Lett., (1994) 35(46):8609–12.

Bray, A.M., et al., *"Simultaneous Multiple Synthesis of Peptide Amides by the Multipin Method. Application of Vapor–Phase Ammonolysis,"* J. Org. Chem., (1994) 59:2197–2203.

Brown, H. C., et al., *"Solvomercuration–Demercuration. I. The Oxymercuration–Demercuration of Representative Olefins in an Aqueous System. A Convenient Mild Procedure for the Markovnikov Hydration of the Carbon—Carbon Double Bond,"* J. Org. Chem., (1970) 35(6):1844–50.

Butler, J.E., et al., "The Physical and Functional Behavior of Capture Antibodies Adsorbed on Polystyrene," J. Immunol. Meth., (1992) 150:77–90.

Byk, G., et al., "One Pot Synthesis of Unsymmetrically Functionalized Polyamines by a Solid Phase Strategy Starting from their Symmetrical Polyamine–Counterparts," Tetrahedron Lett., (1997) 38(18):3219–22.

Carrington, S. et al. (1996). "Inhibition of growth of B16 Murine Melanoma Cells by Novel Spermine Analogs," Pharm Sci 2(1):25–27.

Casero Jr., R. A., et al., "High–Specific Induction of Spermidine/Spermine $N^1$–Acetyltransferase in a Human Large Cell Lung Carcinoma," Biochem. J., (1990) 270:615–20.

Chamaillard, L. et al. (1997). "Polyamine Deprivation Prevents the Development of Tumor–Induced Immune Suppression," *Br J Cancer* 76:365–370.

Chan, P.P., et al., "Triplex DNA: Fundamentals, Advances, and Potential Applications for Gene Therapy," J. Mol. Med., (1997) 75: 267–82.

Chao, J. et al (1997). "N1–Dansyl–Spermine and N1–(n–octanesulfonyl)–Spermine, Novel Glutamate Receptor Antagonists: Block and Permeation of N–Methyl–D–Aspartate Receptors," *Mol Pharmacol* 51(5):861–871.

Chaplinski, V., et al., "A Versatile New Preparation of Cyclopropylamines from Acid Dialkylamides," Angew. Chem. Int. Ed. Engl., (1996) 35(4):413–4.

Dempcy, R. O., et al., "Design and Synthesis of Ribonucleic Guanidine: A Polycationic Analog of RNA," Proc. Natl. Acad. Sci. U.S.A, (1996) 93:4326–30.

Devraj, R., et al., "A Versatile Solid Phase Synthesis of Lavendustin A and Certain Biologically Active Analogs," J. Org. Chem., (1996) 61:9368–73.

Dhainaut et al. (1996). "New Purines and Purine Analogs as Modulators of Multidrug Resistance," *J Med Chem* 39:4099–4108.

DiPasquale, A. et al. (1978). "Epidermal Growth Factor Stimulates Putrescine Transport and Ornithine Decarboxylase Activity in Cultures Human Fibroblasts," *Exp Cell Res* 116:317–323.

Douglas, S. P., et al., "Polymer–Supported Solution Synthesis of Oligosaccharides Using a Novel Versatile Linker for the Synthesis of D–Mannopentaose, a Stuctural Unit of D–Mannans of Pathogenic Yeasts," J. Am. Chem. Soc., (1995) 117:2116–7.

Drug Fut., (1991) 16(12):1165.

Felschow, D.M., et al., "Photoaffinity Labeling of a Cell Surface Polyamine Binding Protein," J. Biol. Chem., (1995) 270(48):28705–11.

Felshow, D.M. et al. (1997). "Selective Labeling of Cell–Surface Polyamine–Binding Proteins on Leukemic and Solid–Tumor Cell Types Using a New Polyamine Photoprobe," *Biochem J* 328(3):889–895.

Flemming, S.A., "Chemical Reagents in Photoaffinity Labeling," Tetrahedron, (1995) 51(46):12479–520.

Flescher, E., et al., "Increased Polyamines May Downregulate Interleukin 2 Production in Rheumatoid Arthritis," J. Clin. Invest., (1989) 83:1356–62.

Furka, A., General Method for Rapid Synthesis of Multicomponent Peptide Mixtures, Int. J. Peptide Protein Res., (1991) 37:487–93.

Furumitsu, Y., et al., "Levels of Urinary Polyamines in Patients with Rheumatoid Arthritis," J. Rheumatology, (1993) 20(10):1661–5.

Gallop, M.A., et al., "Applications of Combinatorial Technologies to Drug Discovery. Background and Peptide Combinatorial Libraries.," J. Med. Chem., (1994) 37(9):1233–51.

Ganem, B., "New Chemistry of Naturally Ocurring Polyamines," Acc. Chem. Res., (1982) 15:290–8.

Ganem, B., et al., "Chemistry of Naturally Ocurring Polyamines. II. Unsaturated Spermidine and Spermine Derivatives," J. Org. Chem., (1987) 52:5044–6.

Ganem, B., et al., "Chemistry of Naturally Ocurring Polyamines. 10. Nonmetabolizable Derivatives of Spermine and Spermidine," J. Org. Chem., (1986) 51:4856–61.

Goodnow Jr., R., et al., *"Synthesis of Glutamate Receptor Antagonist Philanthotoxin–433 (PhTX–433) and its Analogs,"* Tetrahedron Lett., (1990) 46(9):3267–86.

Goodnow, Jr., R.A., et al., "Oligomer Synthesis and DNA/RNA Recognition Properties of a Novel Oligonucleotide Backbone Analog: Glucopyranosyl Nuclei Amide (GNA)," Tetrahedron Lett., (1997) 38(18):3199–3202.

Goodnow, Jr., R.A., et al., "Synthesis of Thymine, Cytosine, Adenine, and Guanine Containing N–Fmoc Protected Amino Acids: Building Blocks for Construction of Novel Oligonucleotide Backbone Analogs," Tetrahedron Lett., (1997) 38(18):3195–8.

Gordon, D.W., et al., *"Reductive Alkylation on a Solid Phase: Synthesis of a Piperazinedione Combinatorial Library,"* Bioorg. Med. Chem. Lett., (1995) 5(1):47–50.

Gordon, E.M., et al., "Applications of Combinatorial Technologies to Drug Discovery. Combinatorial Organic Synthesis, Library Screening Strategies and Future Directions," J. Med. Chem., (1994) 37(10):1385–1401.

Gorus, F., et al., "Applications of Bio– and Chemiluminescence in the Clinical Laboratory," Clin. Chem., (1979) 25(4):512–9.

Green, A.C. et al. (1996) "Polyamine Amides are Neuroprotective in Cerebellar Granule Cell Cultures Challenged with Excitatory Amino Acids," *Brain Research* 717/1–2:135–146.

Ha, H.C. et al., "The Role of Polyamine Catabolism in Polyamine Analogue–Induced Programmed Cell Death," Proc. Natl. Acad. Sci., (1997) 94:11557–62.

Ha, H.C. et al. (1998) "The Natural Polyamine Spermine Functions Directly as a Free Radical Scavenger," *Proc Natl Acad Sci USA* 95:11140–11145.

Han, H. et al., "Ligand–Phase Combinatorial Synthesis," Proc. Natl. Acad. Sci. USA, (1995) 92:6419–23.

Hanauske–Abel, H. M. et al., "Detection of a Sub–Set of Polysomal mRNAs Associated with Modulation of Hypusine Formation at the G1–S Boundary Proposal of a Role for eIF–5A in onset of DNA Replication," FEBS Lett., (1995) 366:92–8.

Hayashi, S. et al. (1996). "Ornithine Decarboxylase Antizyme: A Novel Type of Regulatory Protein," *TIBS* 21:27–30.

Heller, J.S. et al. (1976). "Induction of a Protein Inhibitor to Ornithine Decarboxylase by the End Products of Its Reaction," *Proc Natl Acad Sci USA* 73:1858–1862.

Hernández, A.S. et al., "Solid–Supported tert–Alkoxycarbonylation Reagents for Anchoring of Amines During Solid Phase Organic Synthesis," J. Org. Chem., (1997) 62:3153–7.

Holley, J., et al., "Uptake and Cytotoxicity of Novel Nitroimidazole–Polyamine Conjugates in Ehrlich Ascites Tumour Cells," Biochem. Pharmacol., (1992) 43(4):763–9.

Holley, J.L., et al., "Targeting of Tumor Cells and DNA by a Chlorambucil–Spermidine Conjugates," Cancer Res., (1992) 52:4190–5.

Huber, M. et al., "2,2'–Dithiobis(N–ethyl–spermine–5–carboxamide) Is a High Affinity, Membrane–Impermeant Antagonist of the Mammalian Polyamine Transport System, "J. Biol. Chem., (1996) 271(44):27556–63.

Huber, M. et al., *"Antiproliferative Effect of Spermine Depletion by N–Cyclohexyl–1,3–diaminopropane in Human Breast Cancer Cells,"* Cancer Res., (1995) 55:934–43.

Iwanowicz, E.J. et al., "Preparation of N,N'–Bis–tert–Butoxycarbonylthiourea," Synthetic Comm., (1993) 23(10):1433–5.

Janda, K.D. et al., "Combinatorial Chemistry: A Liquid–Phase Approach," Meth. Enzymol., (1996) 267:234–47.

Janne, J. et al. (1978). "Polyamines in Rapid Growth and Cancer," Biochim Biophys Acta 473:241–293.

Jasnis, M.A. et al., "Polyamines Prevent DFMO–Mediated Inhibition of Angiogenesis," Cancer Lett., (1994) 79:39–43.

Kaiser, E. et al., *"Color Test for Detection of Free Terminal Amino Groups in the Solid–Phase Synthesis of Peptides,"* Anal. Biochem., (1970) 34(2):595–8.

Kakinuma, Y. et al., "Cloning of the Gene Encoding a Putative Serine/Threonine Protein Kinase Which Enhances Spermine Uptake In *Saccharomyces Cerevisiae*," Biochem. Biophys. Res. Comm., (1995) 216(3):985–92.

Karahalios, P. et al., "The Effect of Acylated Polyamine Derivative on Polyamine Uptake Mechanism, Cell Growth, and Polyamine Pools in *Escherichia Coli*, and the Pursuit of Structure/Activity Relationships," Eur. J. Biochem., (1998) 251:998–1004.

Kashiwagi, K. et al. (1990), "Isolation of Polyamine Transport–Deficient Mutants of *Escherichia coli* and Cloning of the Genes for Polyamine Transport Proteins," J *Biol. Chem* 265:20893–20897.

Khan, N., Quemener, V. et al. (1994). "Characterization of Polyamine Transport pathways", in *Neuropharmacology of Polyamines* (Carter, C., ed.), Academic, San Diego, pp. 37–60.

Kossorotov, A. et al. (1974). "Regulatory Effects of Polyamines on Membrane–Bound Acetylcholinesterase," *Biochem J* 144:21–27.

Krapcho, A.P.. et al (1990). "Mono–Protected Diamines. N–tert–butoxylcarbonyl–ά,ω–Alkanediamines from ά,ω–Alkanediamines," *Syn Comm* 20:2559–2564.

Kremmer, T. et al., "Comparative Studies on the Polyamine Metabolism and DFMO Treatment of MCF–7 and MDA–MB–231 Breast Cancer Cell Lines and Xenografts," Anticancer Res., (1991) 11:1807–14.

Laguzza, B. C., et al., "A New Protecting Group For Amines: Synthesis of Anticapsin from L–Tyrosine," Tetrahedron Lett., (1981) 22(16):1483–6.

Lakanen, J. R., et al., "α–Methyl Polyamines: Metabolically Stable Spermidine and Spermine Mimics Capable of Supporting Growth in Cells Depleted of Polyamines," J. Med. Chem., (1992) 35:724–34.

Lam, K.S., "Application of Combinatorial Library Methods in Cancer Research and Drug Discovery," Anti–Cancer Drug Des., (1997) 12:145–67.

Lee, J., "Facile Preparation of Cyclopropylamines from Carboxamides," J. Org. Chem., (1997) 62:1584–5.

Leveque, J. et al (1998). "The Gastrointestinal Polyamine Source Depletion Enhances DFMO induced Polyamine Depletion in MCF–7 Human Breast Cancer Cells In Vivo," *Anticancer Res* 18:2663–3668.

Li, Y. et al, Synthesis and Antitumor Evaluation of a Highly Potent Cytotoxic DNA Cross–Linking Polyamine Analogue, 1,12–Diaziridinyl–4,9–diazadodecane, J. Med. Chem., (1996) 39:339–41.

Li, Y. et al. (1997). "Comparative Molecular Field Analysis–Based Predictive Model of Structure–Function Relationships of Pilyamine Transport Inhibitors in L1210 Cells," *Cancer Res* 57:234–239.

Lloyd–Williams, P., "Convergent Solid–Phase Peptide Synthesis," Tetrahedron, (1993) 49(48):11065–133.

Maillard, L., et al., Percutaneous Delivery of the Gax Gene Inhibits Vessel Stenosis in a rabbit Model of Balloon Angioplasty, Cardiovasc. Res., (1997) 35:536–46.

Marton, L.J., et al., "Polyamines as Targets for Therapeutic Intervention," Annu. Rev. Pharmacol. Toxicol., (1995) 35:55–91.

Matsufuji, S. et al. (1996). "Reading Two Bases Twice: Mammalian Antizyme Frame Shifting in Yeast," *EMBO Journal* 15:1360–1370.

Matthews, H.R. (1993). "Polyamines, Chromatin Structure and Transription," *BioAssays* 15:561–566.

Mitchell, M.F., et al. "α–Difluormethylornithine (DFMO) treatment is Associated with Decreased Blood Vessel Counts in Cervical Intraepithelial Neoplasia (CIN)," Proceedings AACR, (1998) 39(Abstract #600):88.

Moulinoux, J–P. et al. (1991). "Biological Significance of Circulating Polyamines in Oncology," Cell Mol Biol 37:773–783.

Moulinoux, J.P. et al. (1991). "Inhibition of growth of the U–251 Human Glioblastoma in Nude Mice by Polyamine Deprivation," *Anticancer Res* 11:175–180.

Moya, E. et al. (1994). "Synthesis and Neuropharmacological properties of Arthropod Polyamine Amide Toxins," *Neuropharmacology of Polyamines* (Carter, C., ed.), Academic, San Diego, pp. 167–184.

Murakami, Y. et al. (1992). "Ornithine Decarboxylase Is Degraded be the 26S Proteosome Without Ubiquitination," *Nature* 360:597–599.

Muramoto, K., Preparation and Characterization of Photoactivable Heterobifunctional Fluorescent Reagents, Agric. Biol. Chem., (1984) 48(11), 2695–9.

Nakaoka, T., et al., "Inhibition of Rat Vascular Smooth Muscle Proliferation In Vitro and In Vivo by Bone Morphogenetic Protein–2," J. Clin. Invest., (1997) 100(11):2824–32.

Nesher, G. et al., "The In Vitro Effects of Methotrexate on Peripheral Blood Mononuclear Cells," Arthr. Rheumat., (1990) 33(7):954–7.

Newton, G.L. et al., Polyamine–Induced Compaction and Aggregation of DNA—A Major Factor in Radioprotection of Chromatin under Physiological Conditions, Radiation Research, (1996) 145:776–80.

Nilsson, J.L.G. et al., "Fibrin–Stabilizing Factor Inhibitors," ACTA Pharmaceutica Suecica, (1971) 8(4):497–504.

Parchment, R. E. et al., "Polyamine Oxidation, Programmed Cell Death, and Regulation of Melanoma in the Murine Embryonic Limb," Cancer Res., (1989) 49:6680–6.

Persson, L. et al. (1998). "Curative Effect of d,l–2–Difluoromethylornithine on Mice Bearing Mutant L1210 Leukemia Cells Deficient in Polyamine Uptake," Cancer Res 48:4807–4811.

Pfitzner, K.E., et al., "Sulfoxide–Carbodiimide Reactions. I. A Facile Oxidation of Alcohols," J. Am. Chem. Soc., (1965) 87(24):5661–9.

Pohjanpelto, P. (1976) "Putrescine Transport is Greatly Increased in Human Fibroblasts Initiated to Prolifarete," *J Cell Biol* 68:512–520.

Porter, C.W. et al., "Aliphatic Chain Length Specificity of the Polyamine Transport System in Ascites L1210 Leukemia Cells," *J Cancer Res* 44:126–128.

Porter, C.W., et al., Antitumor Activity of $N^1$, $N^{11}$–Bis(ethyl)norspermine against Human Melanoma Xenografts and Possible Biochemical Correlates of Drug action, Cancer Res., (1993) 53:581–6.

Qaraw, M. et al. (1997). "Optimization of the MMT Assay for B16 Murine Melanoma Cells and Its Application in Assessing Growth Inhibition by Polyamines and Novel Polyamine Conjugates," *Pharm Sci* 3(5/6):235–239.

Quemener, V. et al. (1992). "Polyamine Deprivation Enhances Antitumoral Efficacy of Chemotherapy," *Anticancer Res* 12:1447–1454.

Quemener, V. et al. (1992). "Polyamine Deprivation: A New Tool in Cancer Treatment," Anticancer Res., (1994) 14:443–8.

Raditsch, M. et al. (1996). "Polyamine Spider Toxins and Mammalian N–Methyl–D–Aspartate Receptors. Structural Basis for Chemical Blocking and Binding of Argiotoxin 636," *Eur J Biochem* 240:416–426.

Raines, D. E., et al., Potential–Dependent Phase Partitioning of Fluorescent Hydrophobic Ions in Phospholipid Vesicles, J. Membrane Biol., (1984) 82:241–7.

Rajeev, K.G., et al., "Conformationally Restrained Chiral Analogues of Spermine: Chemical Synthesis and Improvements in DNA Triplex Stability," J. Org. Chem., (1997) 62:5169–73.

Ranganathan, R. S., et al., "Novel Analogues of Nucleoside 3',5'–Cyclic Phosphates. I. 5'–Mono–and Dimethyl Analogs of Adenosine 3',5'–Cyclic Phosphate," J. Org. Chem., (1974) 39(3):290–8.

Ransom, R.W. et al. (1998). "Cooperative Modulation of [3H]MK–801 Binding to the N–Methyl–D–Aspartate Receptor_Ion Channel Complex by L–Glutamate, Cycline, and Polyamines," *J Neurochem* 51:830–836.

Rink, H., "Solid–Phase Synthesis of Protected Peptide Fragments Using a Trialkoxy–Diphenyl–Methylester Resin," Tetrahed. Lett., (1987) 28(33):3787–90.

Russell, D. et al. (1968). "Amine Synthesis in Rapidly Growing Systems: Ortithine Decarboxylase Activity in Generating Rat Liver, Chick Embryos, and Various Tumors," *Proc Natl Acad Sci USA* 60:1420–1427.

Salemme, F.R., et al., "Serendipity Meets Precision: The Integration of Structure–Based Drug Design and Combinatorial Chemistry for Efficient Drug Discovery," Structure, (1997) 5(3):319–24.

Sarhan, S. et al. (1989). "The gasrointestial Tract as Polyamine Source for Tumor Growth," *Anticancer Res* 9:215–224.

Sasaki, Y. et al., "Solid–Phase Synthesis and Biological Properties of $\psi[CH_2NH]$ Pseudopeptide Analogues of a Highly Potent Somatostatin Octapeptide," J. Med. Chem., (1987) 30(7):1162–6.

Scalabrino, G. et al. (1981). "Polyamines in Mammalian Tumors. Part 1," *Adv Cancer Res* 35:151–268.

Scalabrino, G. et al. (1982). "Polyamines in Mammalian Tumors. Part 11," *Adv Cancer Res* 36:1–102.

Schallenberg, E. E., et al., "Ethyl Thioltrifluoroacetate As An Acetylating Agent with Particular Reference to Peptide Synthesis," J. Am. Chem. Soc., (1955) 77:2779–83.

Schecter, P.J. et al. (1987). "In Inhibition of Polyamine Metabolism, Biological Significance and Basis for New Therapies," McCann, P.P. et al., eds; pp. 345–364.

Seiler, N. (1987). "Functions of Polyamine Acetylation," *Can Pharmacol* 65:2024–2035.

Seiler, N. et al., "Polyamine Transport In Mammalian Cells," Int. J. Biochem., (1990) 22(3):211–8.

Seiler, N. (1990). "Polyamine Transport in Mammalian Cells," *Int J Biochem* 22:211–218.

Seiler, N. (1995). "Polyamine Oxydase, Properties and Functions," *Progress in Brain Res* 106:333–344.

Seiler, N. et al., "Polyamine Transport in Mammalian Cells. An Update.," Int. J. Biochem. Cell Biol., (1996) 28(8):843–61.

Seiler, N. et al. (1998). "Polyamine Sulfonamides with NMDA Antagonist Properties Are Potent Calmodulin Antagonists and Cytotoxic Agents," *Int J Biochem Cell Biol* 30(3):393–406.

Shyng, S.–L., et al., "Depletion of Intercellular Polyamines Relieves Inward Rectification of Potassium Channels," Proc. Natl. Acad. Sci. USA., (1996) 93:12014–9.

Siegel, M.G. et al., "Rapid Purification of Small Molecule Libraries by Ion Exchange Chromatography," Tetrahedron Lett., (1997) 38(19):3357–60.

Singh, S. et al., "Characterization of Simian Malarial Parasite (*Plasmodium Knowlesi*)–induced Putrescine Transport in Rhesus Monkey Erythrocytes," J. Biol. Chem., (1997) 272(21):13506–11.

Sugiyama, S. et al. (1996). "Crystal Structure of PotD, the Primary Receptor of the Polyamine Transport System in *Escherichia Coli,*" *J Biol Chem* 271:9519–9525.

Suzuki, T. et al. (1994). "Antizyme Protects Against Abnormal Accumulation and Toxicity of Polyamines in Ornithine Decarboxylase–Overproducing Cells," *Proc Natl Acad Sci USA*.

Tabor, H. et al. (1976). "1,4–Diaminobutrane (putrescine), Spermidine, and Spermine," *Ann Rev Biochem* 45:285–306.

Takagi, M.M. et al., The Watanabe Heritable Hyperlipidemic Rabbit Is A Suitable Experimental Model to Study Differences in Tissue Response Between Intimal and Medial Injury After Balloon Angioplasty, Arterioscler. Thromb. Vasc. Biol., (1997) 17(12):3611–9.

Thompson, L. A. et al., "Straightforward and General Method for Coupling Alcohols to Solid Supports," Tetahed. Lett., (1994) 35: 9333–6.

Tomitori, H. et al. (1999). "Identification of a Gene for a Polyamine Transport Protein in Yeast," *J Biol Chem* 274:3265–3267.

Tortora, G. et al., "Synergistic Inhibition of Growth and Induction of Apoptosis by 8–Chloro–cAMP and Paclitaxel or Cisplatin in Human Cancer Cells," Cancer Res., (1997) 57:5107–11.

Tsubokawa, H. et al. (1995). "Effects of a Spider Toxin and Its Analogue on Glutamate–Activated Currents in the Nippocampal CA1 Neuron after Ischemia," *J Neurophys* 74:218–225.

Valerio, R.M. et al., "Multiple Peptide Synthesis on Acid–Labile Handle Derivatized Polyethylene Supports," Int. J. Peptide Protein Res., (1994) 44:158–65.

Ventura, C. et al., "Polyamine Effects on $[Ca^{2+}]_i$ Homeostasis and Contractility in Isolated Rat Ventricular Cardiomyocytes," Am. J. Physiol., (1994) 267:H587–H592.

Veznik, F. et al. (1991). "Synthese von N1,4–Di(p–cumaroyl)spermin, einem moglichen Biogenese–Vorlaufer von Aphelandrin," *Helvetica Chimica Acta* 74:654–661.

Volkow, N. et al. (1983). "Labeled Putrescine as a Probe in Brain Tumors," *Science* 221:673–675.

Walters, D.L. et al., "A Comparison of Fluorescence Versus Chemiluminescence Detection for Analysis of the Fluorescamine Derivative of Histamine by HPLC," Biomed. Chromatogr., (1994) 8:207–11.

Wang, S.–S., "p–Alkoxybenzyl Alcohol Resin and p–Alkoxybenzyloxycarbonylhydrazide Resin for Solid Phase Synthesis of Protected Peptide Fragments," J. Am. Chem. Soc., (1973) 95(4):1128–1333.

Wanzlick, H.W., et al., "1.2–Dianilino–äthan als Aldehydreagens," Chem. Ber., (1953) 86:1463–6.

Webb, H.K. et al. (1999). "1–(N–Alkylamino)–11–(N–Ethylamino)–4,8–Diazaundecanes: Simple Synthetic Polyamine Analogues That Differentially Alter Tublin Polymerization," *J. Med Chem* (in press).

Williams, K. et al. (1991) "Minireview: Modulation of the NMDA Receptor by Polyamines," *Life Science* 48:469–498.

Williams, K. (1997). "Interaction of Polyamines with Ion Channels," *Biochem J* 325:289–297.

Wolff, J. (1998). "Promotion of Microtubule Assembly by Oligocations: Cooperatively between Charged Groups," *Biochemistry* 37:10722–10729.

Xia, C.Q. et al. (1998). "QSAR Analysis of Polyamine Transport Inhibitors in L1210 Cells," *J Drug Target* 6:65–77.

Yuan, Z.–M., et al., Proceedings of the American Association for Cancer Research, (1993) 34(Abst2ract #2264): 380.

\* cited by examiner

Figure 2A

| # | Structure | Ki (µM)[a] | R[b] | Method[c] |
|---|---|---|---|---|
| 3 | (dimethylaminonaphthalene sulfonamide-propyl-NH-butyl-NH-propyl-NH2) | 0.080 | 20 | I |
| 4 | (aminonaphthalene sulfonamide-butyl-C(O)-NH-propyl-NH-butyl-NH-ethyl-NH2) | 0.010 | 400 | IX, XIII |
| 5 | (Cl-phenyl-C(O)-NH-CH2-thiophene-SO2-NH-butyl-C(O)-NH-propyl-NH-butyl-NH-propyl-NH2) | 0.010 | 210 | XIII |
| 6 | (dibenzofuran-SO2-NH-butyl-C(O)-NH-propyl-NH-butyl-NH-propyl-NH2) | 0.005 | 220 | XIII |
| 7 | (pyrene-CH2CH2-C(O)-NH-propyl-NH-butyl-NH-propyl-NH2) | 0.10 | 3.6 | III |
| 8 | (anthracene-SO2-NH-propyl-NH-butyl-NH-propyl-NH2) | 0.110 | 3.7 | II |
| 9 | (anthracene-NH-C(O)-NH-propyl-NH-butyl-NH-propyl-NH2) | 0.440 | 2.7 | IV |
| 10 | (dimethylaminonaphthalene-SO2-NH-propyl-NH-butyl-NH-propyl-NH2) | 0.050 | >10 | XV | a  Inhibition of polyamine uptake: Ki determined from Lineweaver-Burke double reciprocal plots
b  Inhibition of Tumor Cell Growth: R is ratio of IC50 (compound alone) to IC50 (compound + DFMO)
c  Numbers refer to Examples (describing synthesis)
d  Purchased from Aldrich Chemical Company

Figure 2B

| # | Structure | Ki (μM)[a] | R[b] | Method[c] |
|---|---|---|---|---|
| 11 | 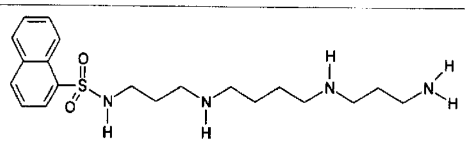 | 0.190 | 2.4 | XV |
| 12 | 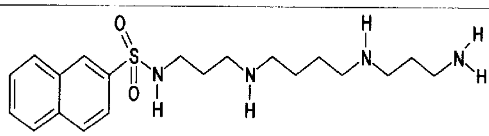 | 0.150 | 4.3 | XV |
| 13 | 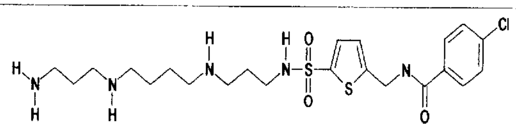 | 0.058 | >47 | XV |
| 14 | 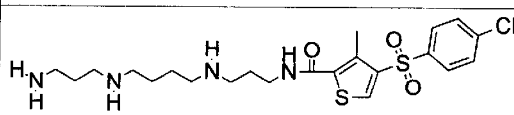 | 0.037 | 14 | XVII |
| 15 | 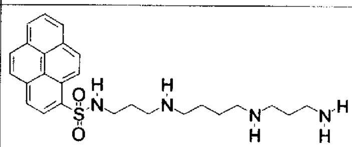 | 0.091 | 2.2 | II |
| 16 | 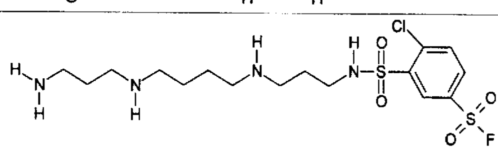 | 0.08 | 2.1 | XV |
| 17 | 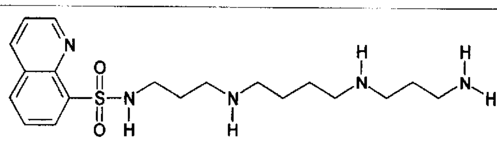 | 0.43 | >31 | XV |
| 18 | 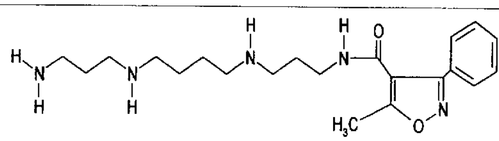 | 0.083 | 40 | XVII |
| 19 | 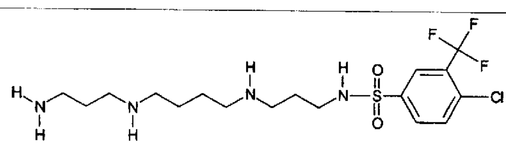 | 0.24 | >10 | XV |

Figure 2C

| # | Structure | Ki (µM)[a] | R[b] | Method[c] |
|---|---|---|---|---|
| 20 | 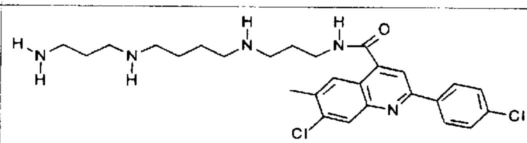 | 0.28 | 1.0 | XVII |
| 21 | 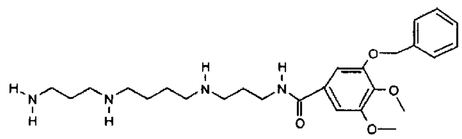 | 0.084 | 1.0 | XVII |
| 22 | 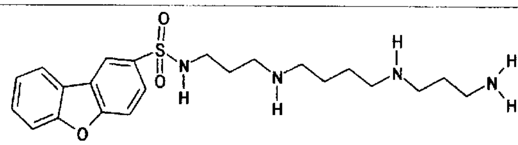 | 0.066 | 11 | XV |
| 23 | 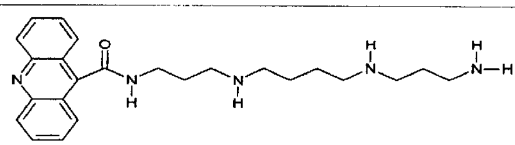 | 0.250 | 6.2 | II |
| 24 | 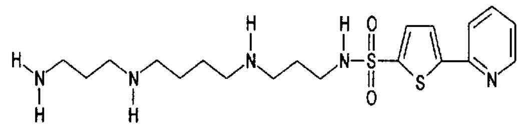 | 0.23 | 10 | XV |
| 25 | 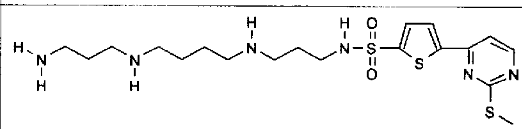 | 0.067 | 8.6 | XV |
| 26 | 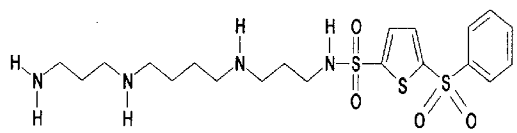 | 0.180 | 15 | XV |
| 27 | 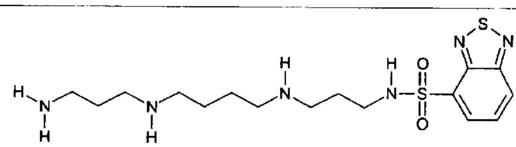 | 0.650 | 9.9 | XV |
| 28 | 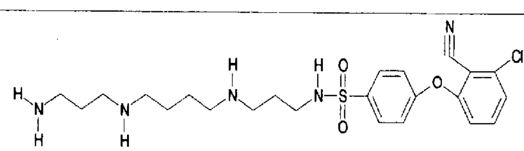 | 0.054 | 9.3 | XV |

| # | Structure | Ki (µM)[a] | R[b] | Method[c] |
|---|---|---|---|---|
| 29 | 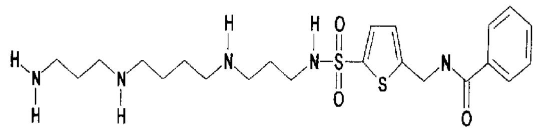 | 0.076 | >46 | XV |
| 30 | 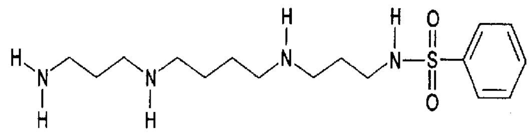 | 0.120 | >10 | XV |
| 31 | 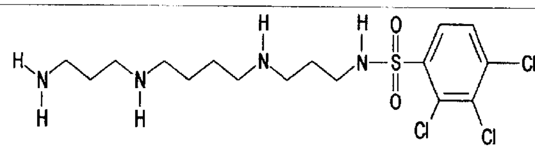 | 0.083 | >12 | XII |
| 32 | 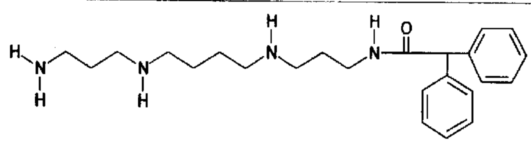 | 0.093 | 2.1 | XVII |
| 33 | 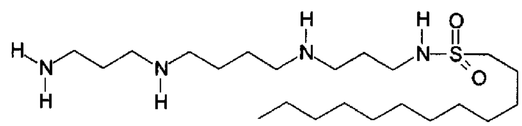 | 0.17 | 1.4 | XV |
| 34 | 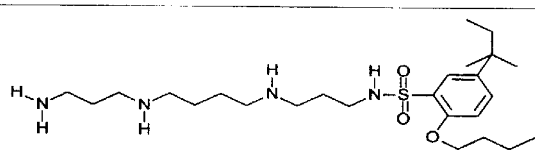 | 0.120 | 1.0 | XV |
| 35 | 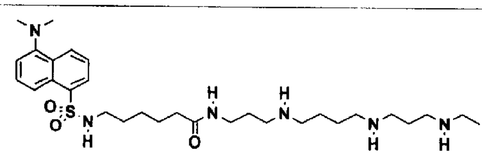 | 0.041 | 33 | XIII |
| 36 | 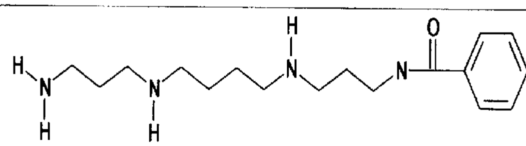 | 0.61 | >2 | XVII |
| 37 | 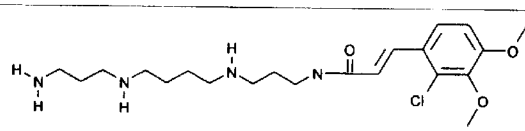 | 0.150 | 2.4 | XVII |

Figure 2E

| # | Structure | Ki (μM)[a] | R[b] | Method[c] |
|---|-----------|------------|------|-----------|
| 38 | 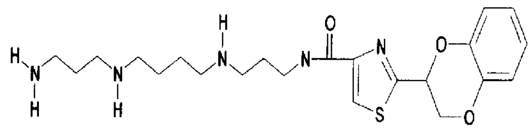 | 0.140 | 1.0 | XVII |
| 39 | 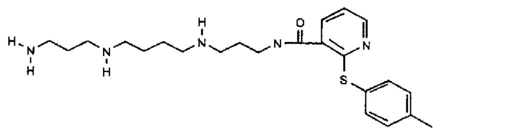 | 0.500 | 1 | XVII |
| 40 | 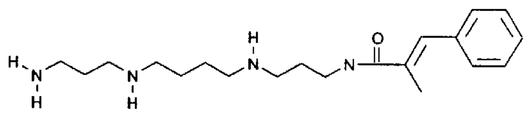 | 0.086 | 18 | XVII |
| 41 | 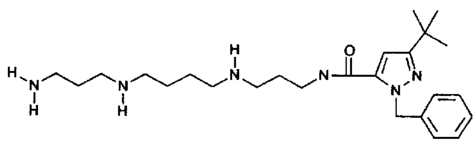 | 0.200 | 1.0 | XVII |
| 42 | 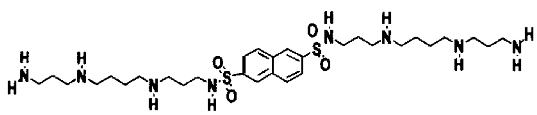 | 0.110 | 1.1 | XIV |
| 43 | 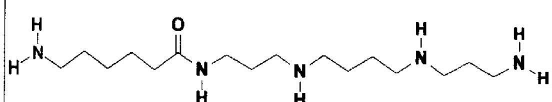 | 0.033 | 76 | XVII |
| 44 | 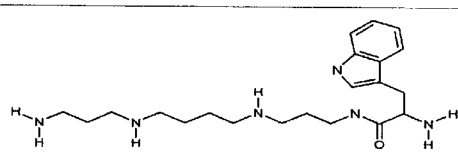 | 0.073 | 39 | XIII |
| 45 | 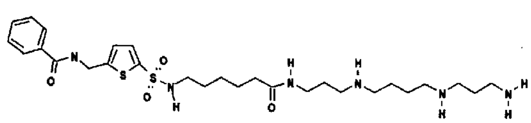 | 0.052 | 3.0 | XIII |
| 46 | 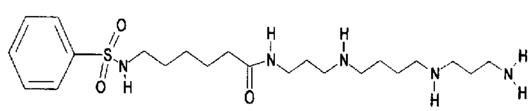 | 0.082 | 63 | XIII |

Figure 2F

| # | Structure | Ki (μM)[a] | R[b] | Method[c] |
|---|---|---|---|---|
| 47 | (structure) | 2.1 | 6.8 | XIII |
| 48 | (structure) | 0.079 | >49 | XIII |
| 49 | (structure) | 0.067 | 3.2 | XV |
| 50 | (structure) | 0.12 | 1.0 | XVII |
| 51 | (structure) | 0.083 | 1.5 | XV |
| 52 | (structure) | 0.094 | 5.3 | XV |
| 53 | (structure) | 0.18 | 1.0 | XV |
| 54 | (structure) | 0.19 | 2.0 | XV |
| 55 | (structure) | 0.079 | >1.1 | IV |

Figure 2G

| # | Structure | Ki (µM)[a] | R[b] | Method[c] |
|---|---|---|---|---|
| 56 | 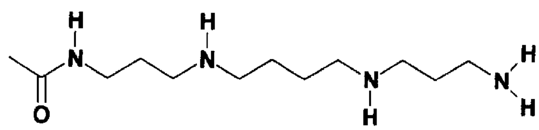 | 0.190 | | d |
| 57 | 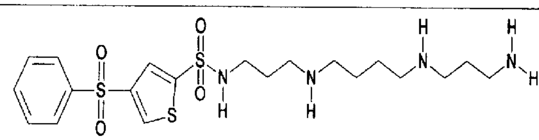 | 0.017 | 170 | XV |
| 58 | 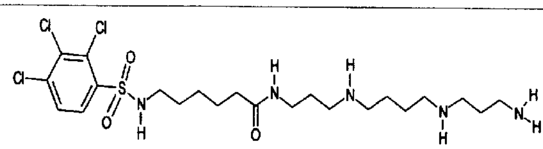 | 0.050 | 189 | XIII |
| 59 | 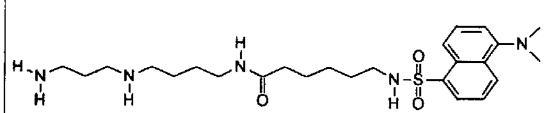 | | >1 | XIII |
| 60 | 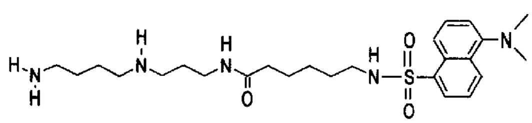 | | >1 | XIII |
| 61 | 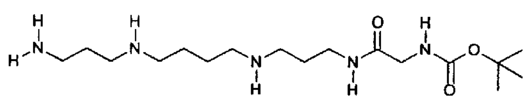 | 0.200 | 1.0 | XIII |
| 62 | 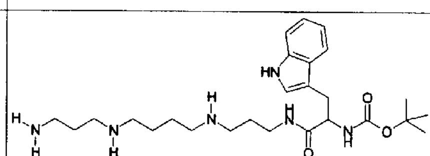 | | >2.0 | XIII |
| 63 | 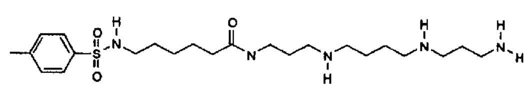 | 0.050 | >1 | XIII |
| 64 | 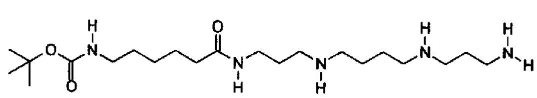 | 0.046 | | XIII |

Figure 2H

| # | Structure | Ki (µM)[a] | R[b] | Method[c] |
|---|-----------|------------|------|-----------|
| 65 | 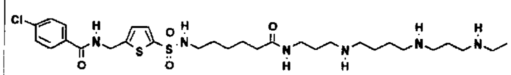 | 0.012 | | XIII |
| 66 | 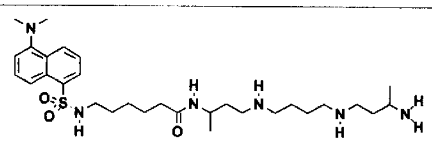 | 0.018 | 27 | XIII |
| 67 | 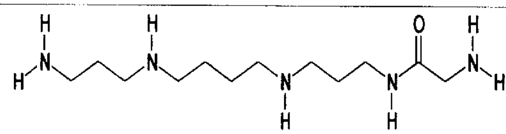 | 0.07 | 1.0 | XIII |
| 68 | 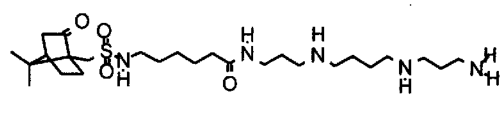 | 0.110 | >4.4 | XIII |
| 69 | 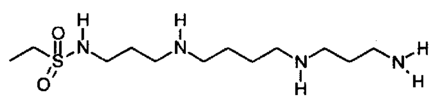 | 0.22 | 1 | XV |
| 70 | 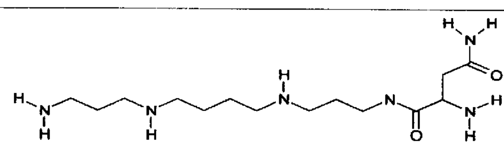 | 0.033 | >12.2 | XIII |
| 71 | 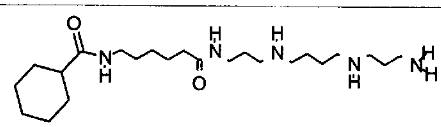 | 0.160 | >1.5 | XIII |
| 72 | 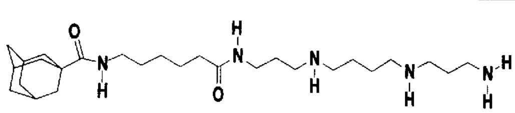 | 0.031 | >100 | XIII |
| 73 | 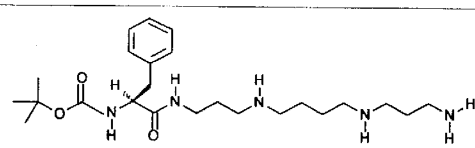 | 0.094 | >1 | XIII |

Figure 2I

| # | Structure | Ki (μM)[a] | R[b] | Method[c] |
|---|---|---|---|---|
| 74 | 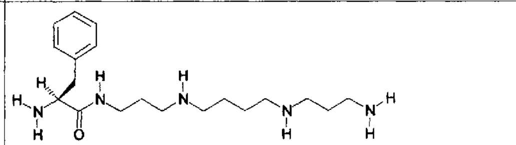 | 0.200 | 1.0 | XIII |
| 75 | 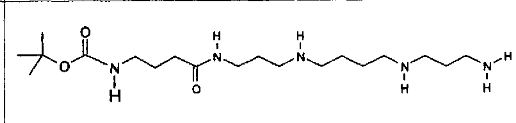 | 0.130 | >1 | XIII |
| 76 | 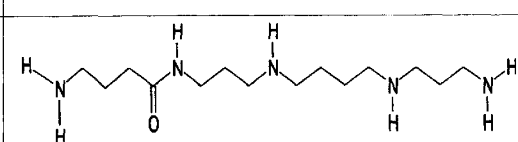 | 0.040 | 1.0 | XIII |
| 77 | 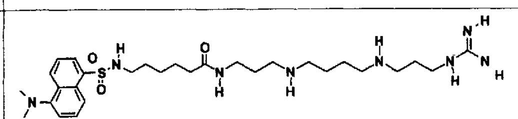 | 0.093 | 1 | XIII |
| 78 | 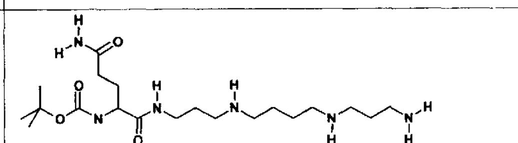 | 0.156 | | XIII |
| 79 | 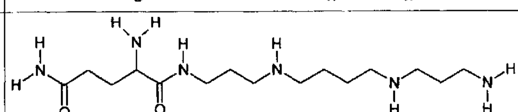 | 0.047 | 1 | XIII |
| 80 | 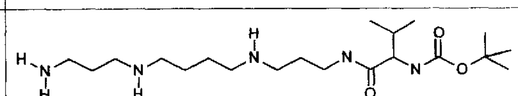 | 0.258 | | XIII |
| 81 | 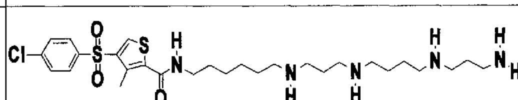 | 0.0096 | 153 | XIII |
| 82 | 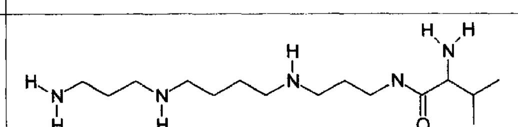 | 0.097 | >54 | XIII |

Figure 2J

| # | Structure | Ki (µM)[a] | R[b] | Method[c] |
|---|-----------|-----------|------|-----------|
| 83 | 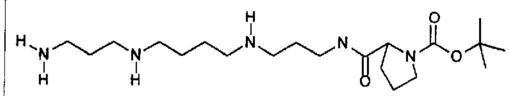 | 0.183 | | XIII |
| 84 | 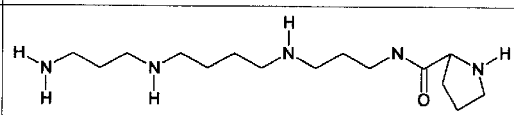 | 0.036 | >3.2 | XIII |
| 85 | 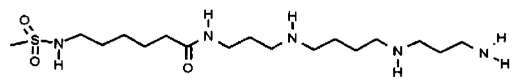 | 0.048 | >6.5 | XIII |
| 86 | 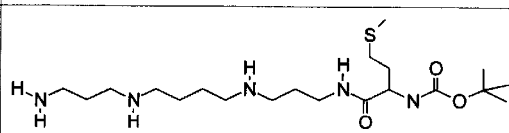 | 0.091 | | XIII |
| 87 | 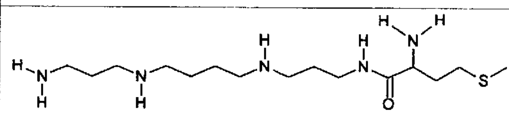 | 0.034 | >1 | XIII |
| 88 | 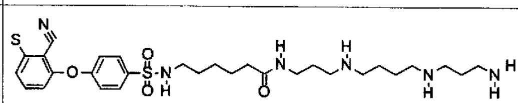 | 0.014 | >40 | XIII |
| 89 | 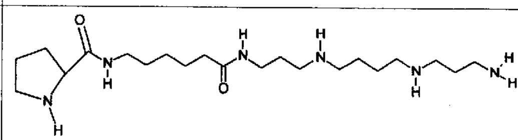 | 0.020 | >1 | XIII |
| 90 | 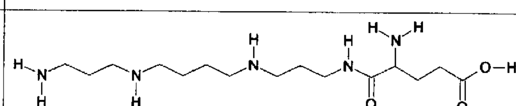 | 0.077 | | XIII |
| 91 | 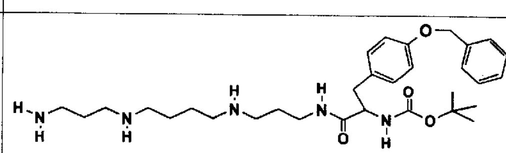 | 0.037 | 1 | XIII |

| # | Structure | Ki (μM)[a] | R[b] | Method[c] |
|---|---|---|---|---|
| 92 | 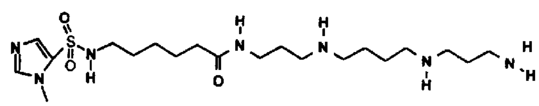 | 0.300 | 1 | XIII |
| 93 | 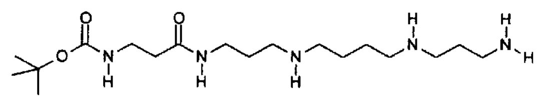 | 0.061 | 1 | XIII |
| 94 | 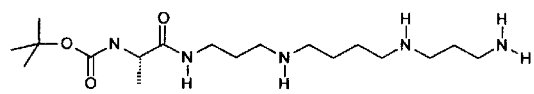 | 0.042 | 1 | XIII |
| 95 | 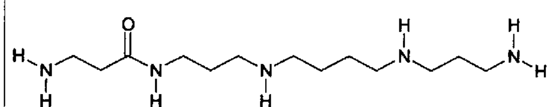 | 0.050 | 1 | XIII |
| 96 | 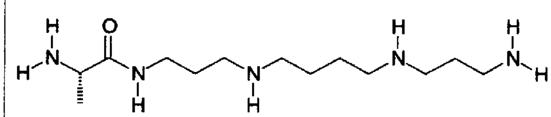 | 0.034 | 1 | XIII |
| 97 | 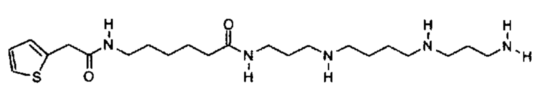 | 0.027 | 1 | XIII |
| 98 | 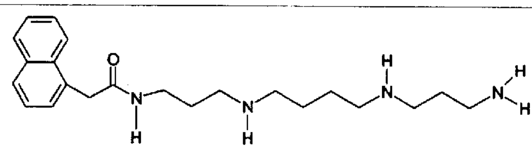 | 0.180 | 12 | d |

ORI 1202
L-Lys-Spm

ORI 1224
L-Orn-Spm

ORI 1157
L-Val-Spm n = 1 to 12 ortho, meta and para aromatic substitution

Compound ID 1236

Compound ID 1286

Compound ID 1289

N1-monosubstituted polyamines: amides, no linker

| ID | mol weight | Structure | Transport: Cell Line | Ki | Growth Inhibition: Cell Line | Half Effect Drug DFMO | IC50 |
|---|---|---|---|---|---|---|---|
| 1032 | 387.5295 | 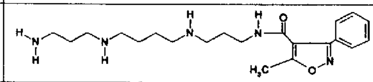 | MDA | 0.19 | MDA | 3.58 | >300 |
| 1033 | 421.9745 | 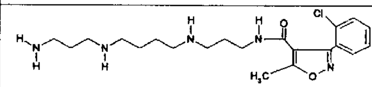 | MDA | 0.083 | MDA | | >300 |
| 1035 | 516.5189 | 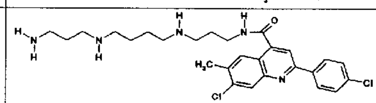 | MDA | 1.0 | MDA | | 50 |
| 1037 | 472.6331 | 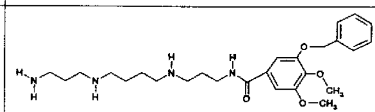 | MDA | 0.28 | MDA | | 100 |
| 1038 | 407.9474 | 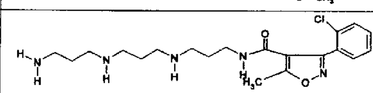 | MDA | 0.084 | MDA | | >300 |
| 1039 | 502.4918 | 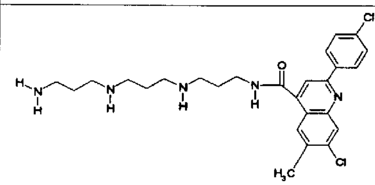 | MDA | >10 | MDA | | 30 |
| 1043 | 407.5635 | 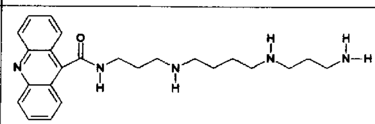 | MDA | 0.344* | MDA | 22.3 | 200 |
| | | | MDA | 0.4 | | | |
| 1053 | 394.5648 | 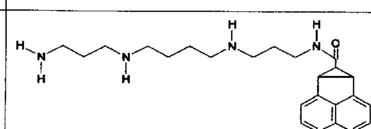 | MDA | 0.54 | MDA | | 260 |

Figure 9A-(1)

| ID | mol weight | Structure | Transport: Cell Line | Ki | Growth Inhibition: Cell Line | Half Effect Drug DFMO | IC50 |
|---|---|---|---|---|---|---|---|
| 1072 | 595.8762 | 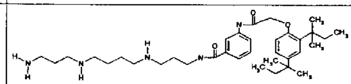 | mda | >1 | | | |
| 1073 | 306.4549 | 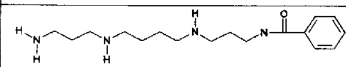 | MDA | >10 | | | |
| 1076 | 426.9911 | 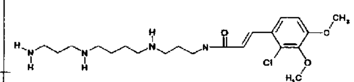 | MDA | 0.61 | mda | 150 | >300 |
| 1077 | 501.1143 | 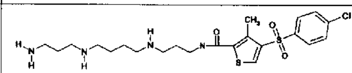 | MDA | 0.116* | mda | 28.1 | 150 |
| 1078 | 447.6040 | 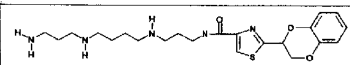 | MDA | 0.165* | mda | 2.46 | 56 |
| | | | MDA | 0.11* | mda | | 19 |
| | | | MDA | 0.037 | pc-3 | | 19.4 |
| | | | | | caco-2 | | 24.4 |
| | | | | | cem | | 6.9 |
| 1079 | 429.6323 | 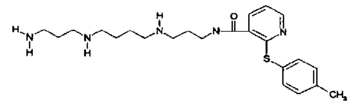 | MDA | 0.19* | pc-3 | | 83 |
| 1080 | 346.5202 | 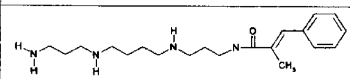 | MDA | 0.594* | mda | | 78 |
| 1081 | 442.6531 | 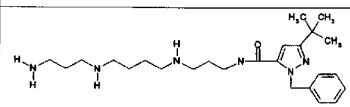 | MDA | 0.062* | mda | 7.4 | 190 |
| | | | MDA | 0.086 | mda | | 26 |
| | | | MDA | 0.297* | pc-3 | | 5.5 |
| | | | | | caco-2 | | 23.0 |

Figure 9A-(2)

| ID | mol weight | Structure | Transport: Cell Line | Ki | Growth Inhibtion: Cell Line | Half Effect Drug DFMO | IC50 |
|---|---|---|---|---|---|---|---|
| 1104 | 457.4043 | 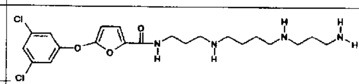 | | | cem | | 1.7 |
| | | | MDA | 0.12 | mda | | 18 |
| | | | | | pc-3 | | 20.2 |
| | | | | | caco-2 | | 36.2 |
| 1163 | 302.4638 | 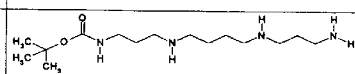 | | | cem | | 4.5 |
| 1166 | 230.3600 | 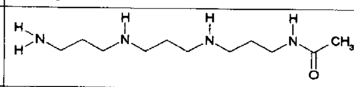 | MDA | 0.083 | | | |
| 1167 | 256.3943 | 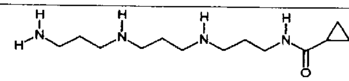 | | | mda | | >100 |
| 1169 | 412.6200 | 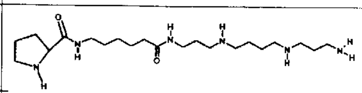 | MDA | 0.0252 | H157 | | >100 |
| 1208 | 308.4700 | 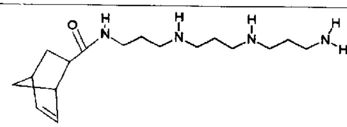 | | | mda | | >100 |
| 1210 | 352.5700 | 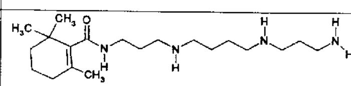 | | | h157 | | >100 |
| 1211 | 341.4100 | 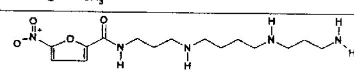 | | | mda | >300 | >300 |
| 1213 | 328.4829 | 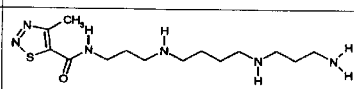 | | | pc-3 | 20.1 | >300 |

Figure 9A-(3)

| ID | mol weight | Structure | Transport: Cell Line | Ki | Growth Inhibition: Cell Line | Half Effect Drug DFMO | IC50 |
|---|---|---|---|---|---|---|---|
| 1214 | 325.4600 | 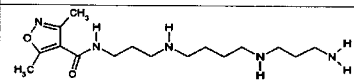 | | | | | |
| 1215 | 284.4500 | 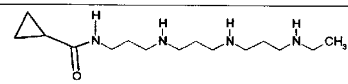 | | | | | |
| 1216 | 313.4900 | 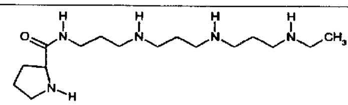 | | | | | |
| 1217 | 307.4400 | 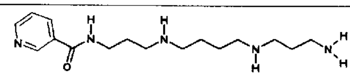 | | | | | |
| 1218 | 307.4424 | 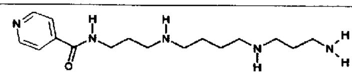 | | | | | |
| 1235 | 364.5792 | 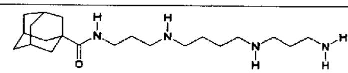 | MDA | 1.14 | | | |
| 1240 | 378.6062 | 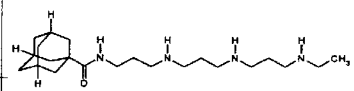 | | | mda | >300 | >300 |
| 1249 | 470.5594 | 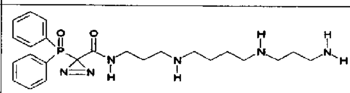 | | | pc-3 | >300 | >300 |
| 1251 | 392.5053 | 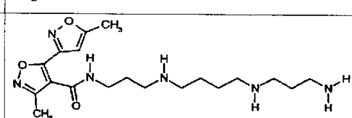 | MDA | >1 | | | |
| 1347 | 472.6795 | 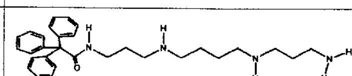 | MDA | | | | |

Figure 9B

N1-monosubstituted polyamines: amides, with linker

| ID | mol weight | Structure | Transport: Cell Line | Ki | Growth Inhibition: Cell Line | Half Effect Drug DFMO | IC50 |
|---|---|---|---|---|---|---|---|
| 1002 | 548.7972 | 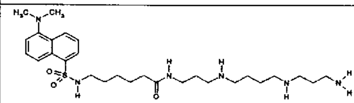 | MDA-MB-231 | .024* | MDA-MB-231 | 2.2 | >100 |
| | | | A172 | .016* | | | |
| | | | PC-3 | 0.0339* | | | |
| | | | MCF-7 | 0.012 | | | |
| | | | MDA | 0.0152* | | | |
| | | | CaCo | 0.0078* | | | |
| | | | mda | 0.0245-0.13 | MDA-MB-231 | 2.0 | >100 |
| | | | mda | 0.0052-0.03 | mda | 0.63 | 450 |
| | | | MDA | 8.6 nM | mda | 2.0 | 380 |
| | | | | | mcf-7 | | 72 |
| | | | | | casmc | | |
| 1009 | 472.6795 | 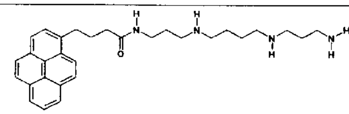 | MDA | 0.104 | MDA | <3 | 25 |
| | | | A172 | 0.12 | | | |
| 1022 | 370.5425 | 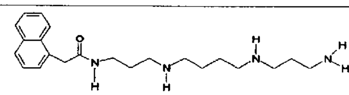 | MDA | 0.230 | MDA | 9.4 | 79 |
| 1040 | 401.5974 | 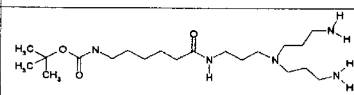 | MDA | | mda | 8.26 | >300 |
| 1055 | 398.5718 | 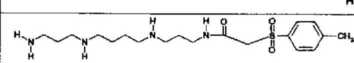 | MDA | | mda | | >100 |
| 1056 | 396.5807 | 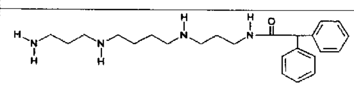 | MDA | 0.11* | MDA | | 6.9 |
| | | | | | | | 150 |

Figure 9B-(1)

| ID | mol weight | Structure | Transport: Cell Line | Ki | Growth Inhibition: Cell Line | Half Effect Drug DFMO | IC50 |
|---|---|---|---|---|---|---|---|
| 1059 | 546.8220 | 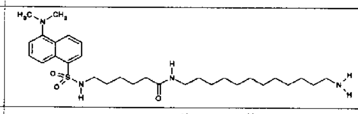 | MDA | 6.5* | mda | | 70 |
| 1060 | 439.8164 | 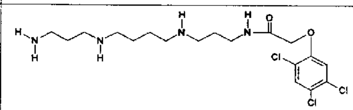 | MDA | 0.099 | mda | >300 | >300 |
| 1061 | 576.8513 | 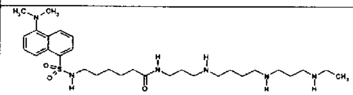 | MDA | 0.00895 | mda | <3 | 360 |
| | | | MDA | 0.0942 | | | |
| | | | MDA | 41.2 nM | mda | 9.81 | 560 |
| | | | MDA | 57.8 nM | | | |
| 1063 | 550.7666 | 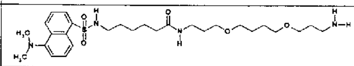 | MDA | 88* | mda | | 18 |
| 1064 | 510.7013 | 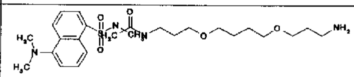 | MDA | > 30 | mda | >100 | >100 |
| 1065 | 632.9597 | 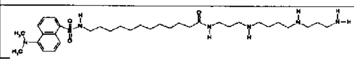 | MDA | 0.76 | mda | >30 | >30 |
| 1066 | 650.9722 | 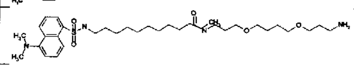 | MDA | 19.2* | mda | | 27 |
| | | | | | pc-3 | | 8.7 |
| | | | | | caco-2 | | >30 |
| | | | | | cem | | 2.9 |
| 1067 | 492.6888 | 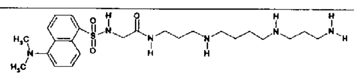 | MDA | 0.070* | mda | >30 | >30 |
| | | | MDA | 0.43 | | | |
| 1068 | 506.7567 | 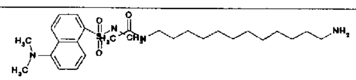 | MDA | > 30 | mda | >30 | >30 |
| 1069 | 459.4310 | 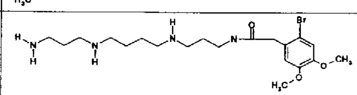 | mda | >1 | | | |

Figure 9B-(2)

| ID | mol weight | Structure | Transport: Cell Line | Ki | Growth Inhibition: Cell Line | Half Effect Drug DFMO | IC50 |
|---|---|---|---|---|---|---|---|
| 1083 | 401.5974 | 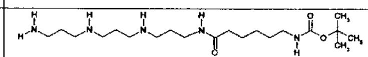 | MDA | 0.74 | | | |
| 1085 | 373.5025 | 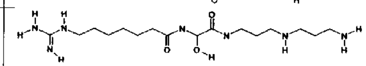 | mda | 81.3 | mda | | >100 |
| 1086 | 481.6000 | 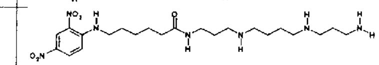 | mda | 2.2 | mda | | >300 |
| 1090 | 629.2897 | 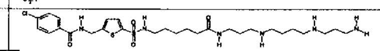 | mda | 0.0147 | mda | 0.960 | 300 |
| | | | MDA | 0.00997 | | | |
| | | | PC-3 | 0.070* | | | |
| | | | MDA | 0.01324 | | | |
| | | | MCF-7 | 0.0252 | | | |
| | | | CaCo | 0.013* | | | |
| | | | MDA | 0.022* | | | |
| | | | MDA | 13.3 - 15.7 nM | mda | 1.54 | >300 |
| | | | MDA | 0.0216 Pre-Incubation | | | |
| | | | MDA | 0.0273 | | | |
| | | | HT-29 | 0.0812 | | | |
| | | | Du145 | 0.016 | | | |
| 1093 | 630.9845 | 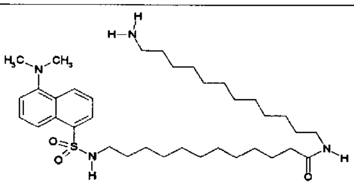 | mda | >30 | | | |
| 1096 | 594.8446 | 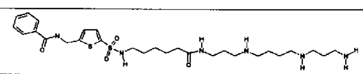 | MDA | 0.094* | mda | 26.5 | 190 |
| | | | MDA | 0.0397 | | | |
| | | | MDA | 0.117 | | | |

Figure 9B-(3)

| ID | mol weight | Structure | Transport: Cell Line | Ki | Growth Inhibition: Cell Line | Half Effect Drug DFMO | IC50 |
|---|---|---|---|---|---|---|---|
| 1097 | 455.6678 | 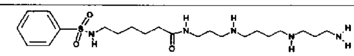 | MDA | 0.0817 | mda | 5.24 | 1200 |
| 1098 | 590.8348 | 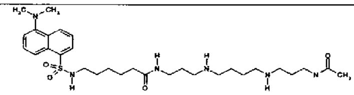 | MDA | 2.1 | mda | 5.52 | 1200 |
| 1100 | 545.7500 | 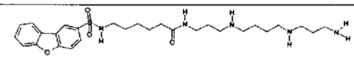 | MDA | 0.0195* | mda | 263 | >1000 |
| | | | MDA | 0.00485 | | | |
| | | | PC-3 | 0.0164 | | | |
| | | | MDA | 0.0105* | mda | 0.588 | 180 |
| | | | MCF-7 | 0.0196 | | | |
| | | | CaCo | 0.00663 | | | |
| 1101 | 513.7292 | 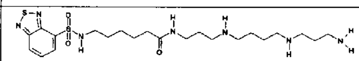 | MDA | 0.0793 | pc-3 | 3.0 | >300 |
| 1107 | 314.5186 | 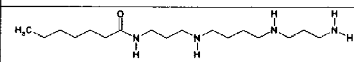 | MDA | 0.182 | mda | 6.17 | >300 |
| 1111 | 565.7189 | 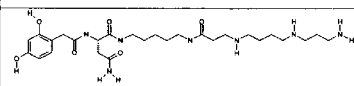 | MDA | 0.19 | | | 63 |
| 1113 | 564.8402 | 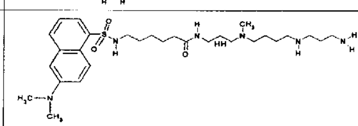 | MDA | 0.0167 | mda | 1.44 | 380 |
| 1114 | 559.0029 | 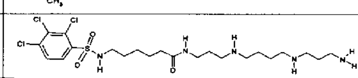 | MDA | 0.073 | pc-3 | 1.43 | 320 |
| | | | | | mda | 1.59 | >300 |

Figure 9B-(4)

| ID | mol weight | Structure | Transport: Cell Line | Ki | Growth Inhibition: Cell Line | Half Effect Drug DFMO | IC50 |
|---|---|---|---|---|---|---|---|
| 1115 | 491.7012 | 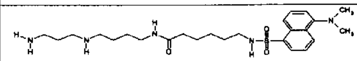 | | | pc-3 | | >300 |
| | | | | | mda | 315 | >300 |
| 1116 | 491.7012 | 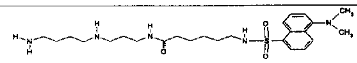 | | | pc-3 | | >300 |
| | | | | | mda | 315 | >300 |
| 1119 | 469.6949 | 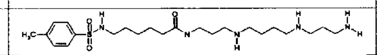 | MDA | 0.0568* | pc-3 | 5.1 | >10 |
| 1120 | 415.6245 | 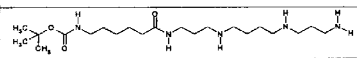 | MDA | 0.0687* | mda | 11.5 | >10 |
| 1122 | 343.5604 | 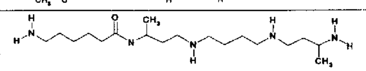 | MDA | 0.248 | | | |
| | | | MDA | 0.397 | | | |
| 1123 | 657.3438 | 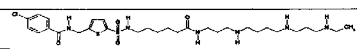 | MDA | 0.012 | MDA | 5.20 | 255 |
| | | | MDA | 0.0136 | PC-3 | 1.23 | 530 |
| | | | PC-3 | 0.038 | | | |
| | | | Du145 | 0.0985 | | | |
| 1124 | 576.8513 | 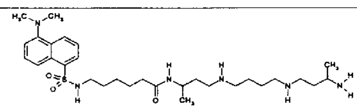 | MDA | 0.0178 | mda | 13.2 | >300 |
| | | | MDA | 0.0466 | | | |
| 1129 | 529.7915 | 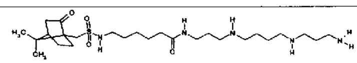 | MDA | 0.17* | mda | 68.2 | >300 |
| | | | | | pc-3 | 71.3 | >300 |
| 1135 | 425.6633 | 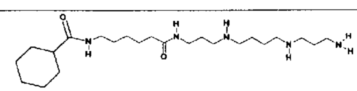 | MDA | 0.167* | pc-3 | 29.2 | >300 |
| | | | | | mda | 66.5 | >100 |
| 1136 | 477.7398 | 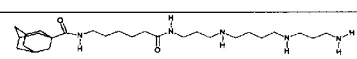 | MDA | 0.0446* | mda | 9.68 | >1000 |
| | | | MDA | 0.0344 | | 9.23 | >1000 |

Figure 9B-(5)

| ID | mol weight | Structure | Transport: Cell Line | Ki | Growth Inhibition: Cell Line | Half Effect Drug DFMO | IC50 |
|---|---|---|---|---|---|---|---|
| 1149 | 387.5703 | 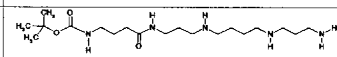 | MDA | 0.136* | mda | >100 | >100 |
| 1152 | 590.8377 | 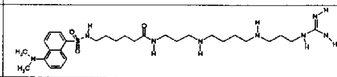 | MDA | 0.0903 | pc-3 | | 99 |
| 1156 | 614.2750 | 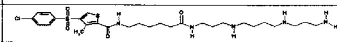 | MDA | 0.085 | mda | 1.55 | >100 |
| | | | MDA | 0.00955 | mda | 2.56 | >300 |
| 1160 | 393.5961 | 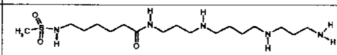 | MDA | 0.0564* | pc-3 | 45.8 | >300 |
| | | | | | pc-3 | | 64 |
| 1161 | 357.5438 | 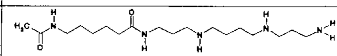 | MDA | > 0.3 | mda | >300 | >300 |
| | | | MDA | >1 | pc-3 | >300 | >300 |
| 1165 | 607.2209 | 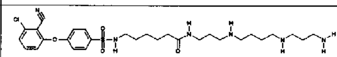 | MDA | 0.0143 | mda | <3 | 199 |
| | | | | | pc-3 | <3 | 188 |
| 1174 | 459.6600 | 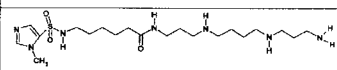 | MDA | 0.3 | mda | >300 | >300 |
| | | | | | pc-3 | >300 | >300 |
| 1175 | 373.5432 | 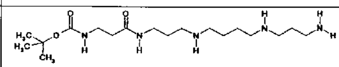 | MDA | 0.061 | mda | >300 | >300 |
| | | | | | pc-3 | 24.7 | >300 |
| 1179 | 369.5550 | 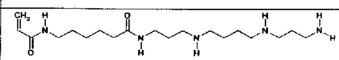 | MDA | > 1 uM | mda | >300 | >300 |
| 1180 | 439.6684 | 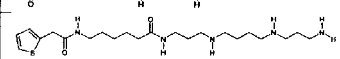 | MDA | 0.0265 | mda | >300 | >300 |
| 1203 | 244.3832 | 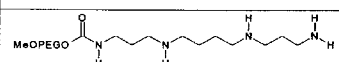 | | | | | |
| 1209 | 359.5200 | 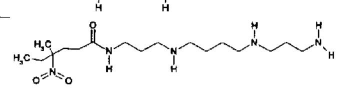 | MDA | >1 | mda | 62 | 277 |

Figure 9B-(6)
| ID | mol weight | Structure | Transport: Cell Line | Ki | Growth Inhibition: Cell Line | Half Effect Drug DFMO | IC50 |
|---|---|---|---|---|---|---|---|
| 1233 | 587.2084 | 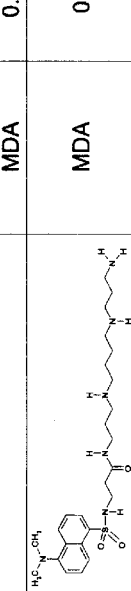 | MDA | 0.0355* | pc-3 | 72 | 227 |
| 1234 | 506.7159 | 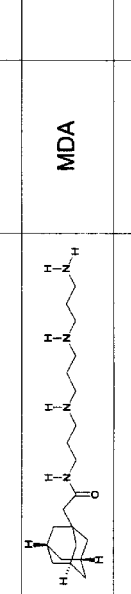 | MDA | 0.0185* | mda | 1.9 | >300 |
| 1238 | 364.5792 | 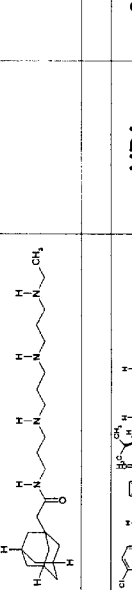 | MDA | 0.0565 | pc-3 | 0.56 | >300 |
| 1239 | 392.6333 | 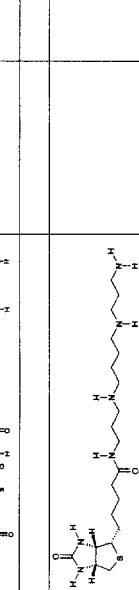 | MDA | >1 | mda | 1.6 | >300 |
| 1241 | 615.2626 | 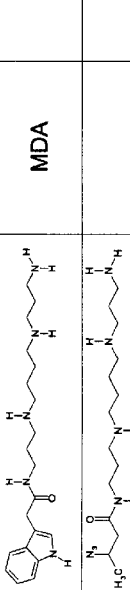 | | | pc-3 | 0.87 | >300 |
| 1243 | 428.6448 | 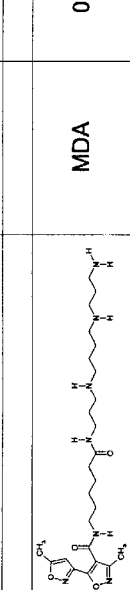 | MDA | 0.0262 | mda | | 235 |
| 1244 | 359.5189 | 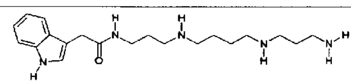 | | 0.48 | pc-3 | | 208 |
| 1245 | 313.4495 | 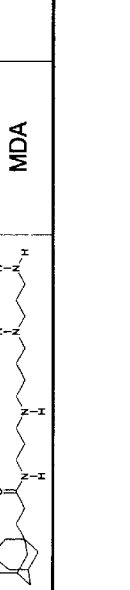 | MDA | | mda | | 195 |
| 1254 | 505.6660 | 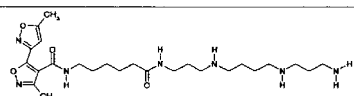 | MDA | 0.0577 | pc-3 | | 173 |
| 1281 | 392.6333 | 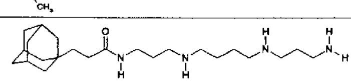 | MDA | >1 | | | |

Figure 9B-(7)

| ID | mol weight | Structure | Transport: Cell Line | Ki | Growth Inhibition: Cell Line | Half Effect Drug DFMO | IC50 |
|---|---|---|---|---|---|---|---|
| 1298 | 413.5865 | 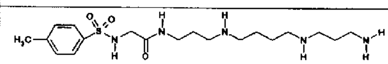 | | | | | |
| 1305 | 348.5361 | 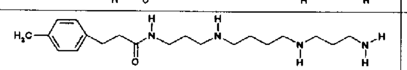 | | | | | |
| 1315 | 477.4338 | 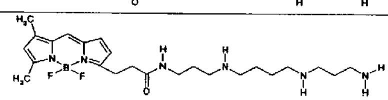 | | | | | |
| 1340 | 644.3043 | 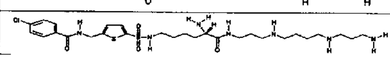 | | | | | |

Figure 9C

N1-monosubstituted polyamines: amides, amino alkyl

| ID | mol weight | Structure | Transport: Cell Line | Ki | Growth Inhibition: Cell Line | Half Effect Drug DFMO | IC50 |
|---|---|---|---|---|---|---|---|
| 1091 | 301.4791 | 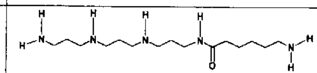 | | | mda | | >100 |
| 1094 | 315.5062 | 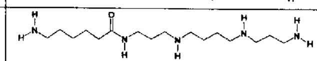 | MDA | 0.075 | mda | 18 | >300 |
| | | | MDA | 0.117 | mda | 51.5 | >1000 |
| | | | MDA | 0.040 | | | |
| | | | MDA | 0.028 - 0.078 | mda | 54 | >300 |
| 1110 | 244.3832 | 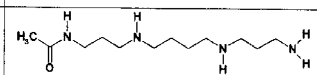 | MDA | 0.043 | | | |
| | | | MDA | 0.162 | MDA | | |
| | | | MDA | 0.190 | | | |
| 1121 | 343.5604 | 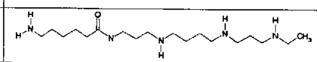 | MDA | 0.64 | MDA | >300 | >300 |
| | | | MDA | 0.5 | PC-3 | | >300 |
| 1122 | 343.5604 | 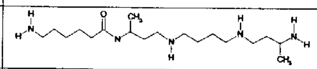 | MDA | 0.248 | | | |
| | | | MDA | 0.397 | | | |
| 1126 | 301.4791 | 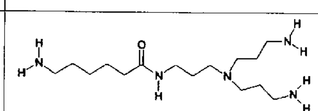 | MDA | > 10 | mda | | >100 |
| 1150 | 287.452 | 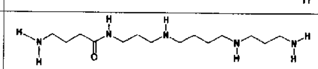 | MDA | 0.043* | mda | | >100 |
| 1177 | 273.4249 | 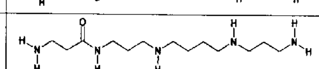 | MDA | 0.0756* | mda | >300 | >300 |
| | | | PC-3 | 0.0636 | pc-3 | <3 | >300 |
| | | | Du145 | 0.147 | MDA | >100 | >100 |
| | | | | | PC-3 | 2.85 | >100 |
| 1197 | 301.4791 | 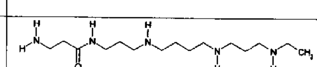 | MDA | 0.39 | MDA | | >300 |
| | | | | | PC-3 | >300 | 460 |

Figure 9C-(1)

| ID | mol weight | Structure | Transport: Cell Line | Ki | Growth Inhibition: Cell Line | Half Effect Drug DFMO | IC50 |
|---|---|---|---|---|---|---|---|
| 1198 | 301.4791 | 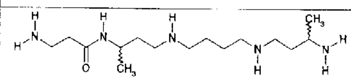 | MDA | 0.424 | MDA | >300 | >300 |
| | | | | | PC-3 | 299 | >300 |

Figure 9D

N1-monosubstituted polyamines: amides, protected amino acid head group

| ID | mol weight | Structure | Transport: Cell Line | Ki | Growth Inhibition: Cell Line | Half Effect Drug DFMO | IC50 |
|---|---|---|---|---|---|---|---|
| 1117 | 359.5161 | 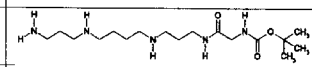 | MDA | 0.232* | mda | | >100 |
| 1118 | 488.679 | 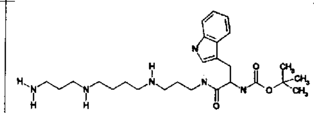 | | | pc-3 | 22.64 | >300 |
| 1127 | 458.6526 | 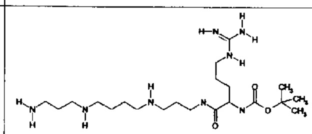 | | | mda | 50.4 | >100 |
| 1147 | 481.7281 | 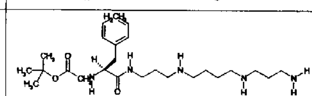 | MDA | 0.098* | mda | >100 | >100 |
| 1151 | 416.5685 | 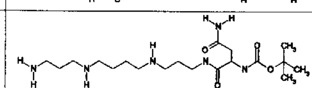 | MDA | >1 | | | |
| 1153 | 430.5955 | 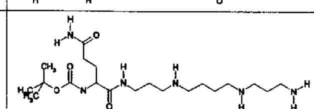 | mda | 0.156 | | | |
| 1155 | 401.5974 | 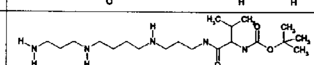 | MDA | 0.258 | | | |
| 1158 | 399.5815 | 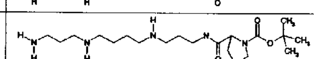 | MDA | 0.183 | | | |
| 1162 | 433.6614 | 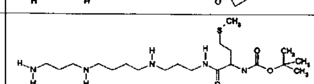 | MDA | 0.0913 | | | |
| | | | MDA | 0.083 | | | |
| 1170 | 521.7061 | 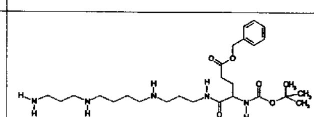 | MDA | >1 | mda | >300 | >300 |

Figure 9D-(1)
| ID | mol weight | Structure | Transport: Cell Line | Ki | Growth Inhibition: Cell Line | Half Effect Drug DFMO | IC50 |
|---|---|---|---|---|---|---|---|
| 1172 | 555.7673 | 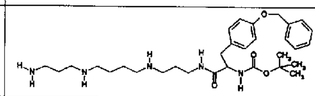 | MDA | 37.1 | pc-3 | >300 | >300 |
|  |  |  |  |  | mda |  | 20 |
| 1176 | 373.5432 |  | MDA | 0.0418 | pc-3 |  | 20 |
|  |  |  | MDA |  | mda | >300 | >300 |
| 1176 | 373.5432 |  | MDA | 0.0418 | pc-3 | 14.0 | >300 |
|  |  |  | MDA |  | mda | >300 | >300 |
| 1176 | 373.5432 |  | MDA | 0.0418 | pc-3 | 14.0 | >300 |
|  |  |  | MDA |  | mda | >300 | >300 |
| 1176 | 373.5432 |  | MDA | 0.0418 | pc-3 | 14.0 | >300 |
|  |  |  | MDA |  | mda | >300 | >300 |
| 1176 | 373.5432 |  | MDA | 0.0418 | pc-3 | 14.0 | >300 |
| 1189 | 493.6956 | 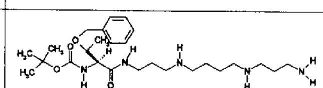 | MDA | 0.465 | MDA | 52 | >300 |
|  |  |  |  |  | PC-3 | 100 | >300 |
| 1193 | 415.6245 | 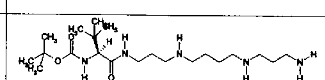 | MDA | 0.265 | pc-3 | >300 | >300 |
|  |  |  |  |  | MDA | 89.2 | >300 |
| 1195 | 401.5974 | 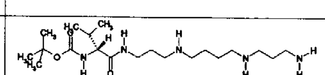 | MDA | 0.271 | PC-3 | 91.9 | >300 |
|  |  |  |  |  | MDA | 37.9 | >300 |
|  |  |  |  |  | PC-3 | 70.9 | >300 |

Figure 9D-(2)

| ID | mol weight | Structure | Transport: Cell Line | Ki | Growth Inhibition: Cell Line | Half Effect Drug DFMO | IC50 |
|---|---|---|---|---|---|---|---|
| 1199 | 564.775 | 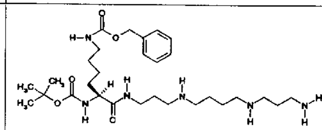 | MDA | 0.060* | MDA | 15.5 | >300 |
| 1200 | 464.6567 | 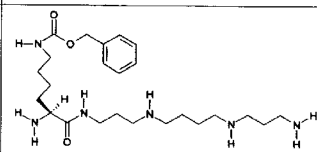 | MDA | 0.039 | PC-3 | 9.20 | >300 |
| | | | | | MDA | 29.8 | >300 |
| 1201 | 430.6392 | 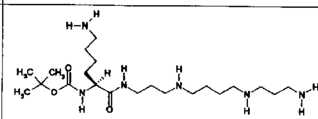 | MDA | 0.191 | MDA | 41.3 | >300 |
| | | | | | PC-3 | 7.87 | >300 |
| | | | | | PC-3 | 8.51 | >300 |
| 1205 | 403.5697 | 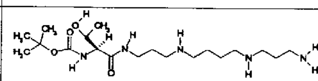 | MDA | 0.1094 | MDA | 36.9 | >300 |
| 1206 | 393.5773 | 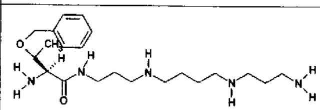 | | | PC-3 | 16.9 | 430 |
| | | | | | mda | 100 | >300 |
| 1219 | 387.5703 | 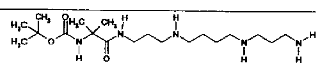 | | | pc-3 | >300 | >300 |
| | | | | | mda | 19 | >300 |
| 1221 | 550.7479 | 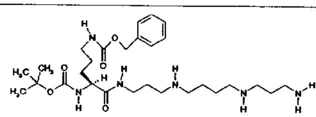 | | | pc-3 | 67 | >300 |

Figure 9D-(3)

| ID | mol weight | Structure | Transport: Cell Line | Ki | Growth Inhibition: Cell Line | Half Effect Drug DFMO | IC50 |
|---|---|---|---|---|---|---|---|
| 1222 | 450.6296 | 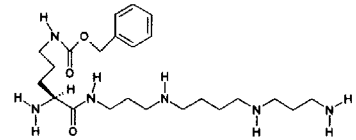 | | | | | |
| 1223 | 416.6121 | 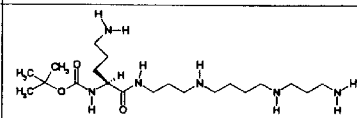 | | | | | |
| 1229 | 415.6245 | 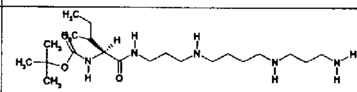 | | | | | |
| 1231 | 415.6245 | 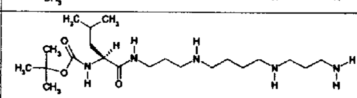 | | | | | |
| 1259 | 760.9417 | 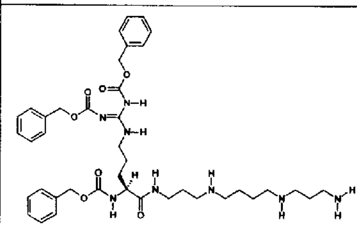 | | | | | |

Figure 9E

N1-monosubstituted polyamines: amides, natural alpha-amino acid head group

| ID | mol weight | Structure | Transport: Cell Line | Ki | Growth Inhibition: Cell Line | Half Effect Drug DFMO | IC50 |
|---|---|---|---|---|---|---|---|
| 1095 | 388.5607 | 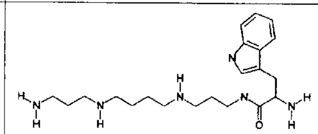 | MDA | 0.073 | mda | 5.3 | >300 |
| | | | | | mda | 8.44 | 560 |
| | | | MDA | 0.011 - 0.042 | pc-3 | 14.05 | >1000 |
| | | | | | mda | 30.0 | >300 |
| 1125 | 259.3978 | 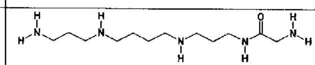 | MDA | 0.07 | mda | | >100 |
| 1131 | 316.4501 | 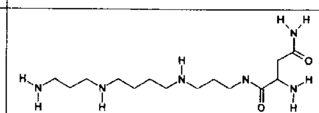 | MDA | 0.1036* | | | |
| | | | MDA | 0.0325 | pc-3 | 57.0 | >300 |
| | | | | | mda | 81.97 | >1000 |
| | | | | | mda | 113 | >300 |
| | | | | | pc-3 | 57 | >300 |
| 1148 | 349.5237 | 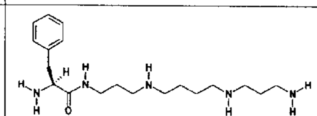 | MDA | 0.214* | mda | | >100 |
| 1154 | 330.4772 | 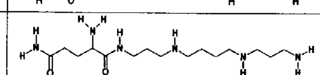 | MDA | 0.047 | mda | >300 | >300 |
| | | | | | pc-3 | >300 | >300 |
| 1157 | 301.4791 | 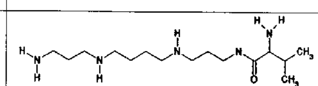 | MDA | 0.160* | mda | 5.58 | >300 |
| | | | MDA | 0.0392 | pc-3 | 14.35 | >300 |
| | | | PC-3 | 0.149 | MDA | 26.42 | >300 |
| | | | Du145 | 0.109 | PC-3 | 3.86 | >300 |
| | | | MDA | 0.0514 | pc-3 | 5.28 | >300 |
| | | | Du145 | 0.0467 | | | |

Figure 9E-(1)

| ID | mol weight | Structure | Transport: Cell Line | Ki | Growth Inhibition: Cell Line | Half Effect Drug DFMO | IC50 |
|---|---|---|---|---|---|---|---|
| 1159 | 299.4632 | 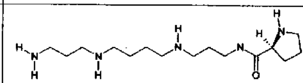 | MDA | 0.0255 | mda | 92.8 | >300 |
| | | | MDA | 0.0499 | pc-3 | 16.5 | 81 |
| 1164 | 333.5431 | 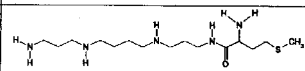 | MDA | 21.5 - 50 nM | mda | >100 | >100 |
| | | | | | pc-3 | 12.1 | >100 |
| 1171 | 331.462 | 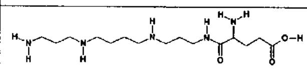 | MDA | 0.0335 | mda | >300 | >300 |
| | | | | | pc-3 | >300 | >300 |
| 1173 | 365.5231 | 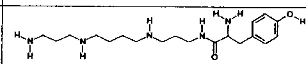 | MDA | 0.0765 | MDA | 300 | >300 |
| | | | MDA | 0.13 | PC-3 | 185 | >300 |
| 1178 | 273.4249 | 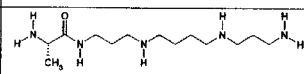 | MDA | 0.0768 | MDA | 94.6 | >300 |
| | | | | | PC-3 | 42.7 | >300 |
| 1186 | 317.4349 | 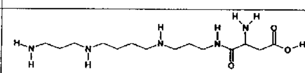 | MDA | 0.0526* | mda | >300 | >300 |
| | | | | | pc-3 | >300 | >300 |
| 1187 | 289.4243 | 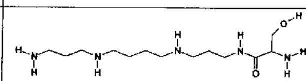 | MDA | 0.167 | MDA | 300 | >300 |
| | | | MDA | 0.38 | PC-3 | 213 | >300 |
| 1202 | 330.5209 | 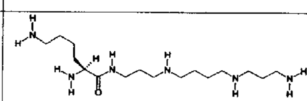 | MDA | 0.0453 | MDA | 25.5 | >300 |
| | | | | | PC-3 | 20.8 | >300 |
| | | | MDA | 0.0295 | MDA | 4.75 | >300 |
| | | | PC3 | 0.748 | PC-3 | 5.30 | >300 |
| | | | MDA | 0.147 | pc-3 | 1.7 | |
| | | | MDA | 0.032* Pre-Incubation | | | |

Figure 9E-(2)

| ID | mol weight | Structure | Transport: Cell Line | Ki | Growth Inhibition: Cell Line | Half Effect Drug DFMO | IC50 |
|---|---|---|---|---|---|---|---|
| | | | MDA | 0.05 | | | |
| | | | HT-29 | 0.185 | | | |
| 1207 | 303.4514 | 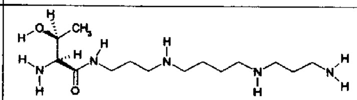 | MDA | 0.13 | mda | 6.5 | >300 |
| 1228 | 315.5062 | 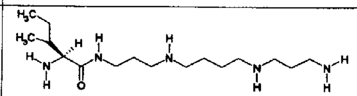 | MDA | 0.124 | pc-3 | 62 | >300 |
| 1230 | 315.5062 | 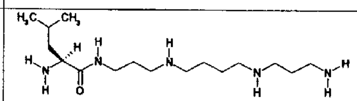 | MDA | 0.0323 | mda | 9.1 | >300 |
| | | | | | pc-3 | 4.0 | >300 |
| 1237 | 374.6181 | 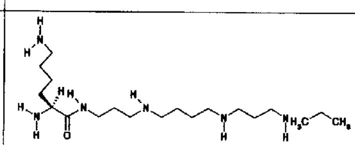 | MDA | 0.113 | mda | >300 | >300 |
| | | | | | pc-3 | 6.2 | >300 |
| 1260 | 358.5343 | 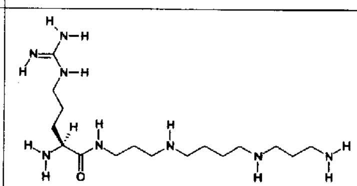 | MDA | 0.099 | mda | >300 | >300 |
| | | | | | mda | 6.80 | >100 |
| | | | | | pc3 | 3.04 | >100 |

Figure 9H

| N1-monosubstituted polyamines: sulfonamides | | | | | | | |
|---|---|---|---|---|---|---|---|
| ID | mol weight | Structure | Transport: Cell Line | Ki | Growth Inhibition: Cell Line | Half Effect Drug DFMO | IC50 |
| 1001 | 435.6365 | | MDA | .039 | MDA | 20 | 600 |
| | | | A172 | .08 | A172 | | |
| 1003 | 421.6094 | | MDA | 1 | MDA | 100uM | >300 |
| 1005 | 318.3975 | | A172 | 23 | A172 | | 28 uM |
| 1006 | 446.6164 | | mda | 1.46 | MDA | | 40 uM |
| 1007 | 302.4389 | | A172 | 60 | A172 | | 20 |
| | | | | | MDA | | 50 |
| 1008 | 416.6308 | | MDA | >10 | mda | | >300 |
| | | | MDA | 0.110 | MDA | 1.7 | >300 |
| 1010 | 442.6282 | | A172 | 0.082 | MDA | 1.05 | 20 |
| | | | | | MDA | | 18 |

Figure 9H-(1)

| ID | mol weight | Structure | Transport: Cell Line | Ki | Growth Inhibition: Cell Line | Half Effect Drug DFMO | IC50 |
|---|---|---|---|---|---|---|---|
| 1011 | 435.6365 | 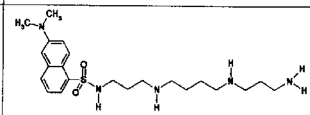 | MDA | 0.066* | MDA | 6.0 | 50 |
| 1012 | 421.6094 | 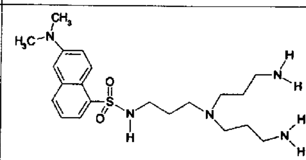 | MDA | >10 | MDA | <3.0 | 50 |
| 1013 | 435.6365 | 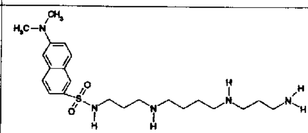 | MDA | 3.5 | MDA | 13.4 | 150 |
| 1014 | 421.6094 | 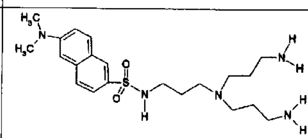 | A172 | 1.34 | MDA | | 50 |
| | | | MDA | >10 | | | |
| 1015 | 489.6881 | 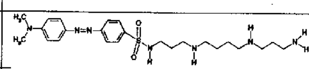 | MDA | 2.9 | MDA | | 15 |
| | | | A172 | 1.6 | pc-3 | | >30 |
| | | | | | caco-2 | | 18.2 |
| | | | | | cem | | >30 |
| 1016 | 475.661 | 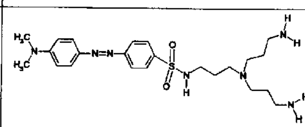 | MDA | >10 | MDA | | 13 |
| 1017 | 392.5676 | 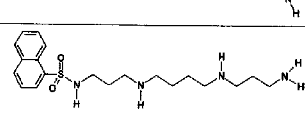 | MDA | .187 | MDA | 14.2 | 50 |

Figure 9H-(2)

| ID | mol weight | Structure | Transport: Cell Line | Ki | Growth Inhibition: Cell Line | Half Effect Drug DFMO | IC50 |
|---|---|---|---|---|---|---|---|
| 1018 | 278.3758 | 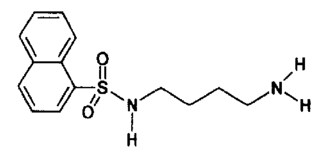 | A172 | .24 | | | |
| 1019 | 392.5676 | 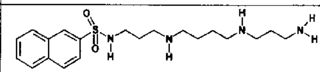 | mda | >30 | MDA | | 120 |
| 1020 | 379.5281 | 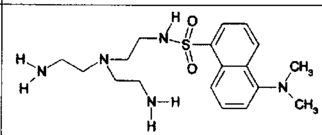 | MDA | 0.2* | MDA | 7.5 | 50 |
| | | | A172 | 0.37 | MDA | 4.4 | 50 |
| 1023 | 466.6505 | 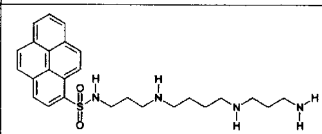 | MDA | >30 | MDA | | 110 |
| | | | A172 | .091 | | | |
| | | | | .075 | MDA | | 22 |
| 1024 | 407.5823 | 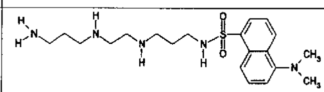 | MDA | 5.4 | MDA | | 50 |
| 1025 | 365.501 | 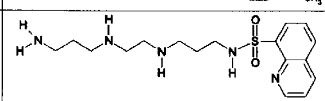 | MDA | 4.3 | MDA | | >300 |
| 1026 | 364.5135 | 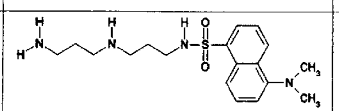 | MDA | 2.7 | MDA | | 50 |
| 1027 | 322.4322 | 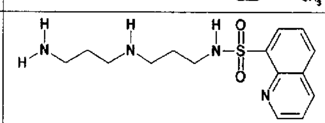 | MDA | >10 | MDA | | >300 |

Figure 9H-(3)
| ID | mol weight | Structure | Transport: Cell Line | Ki | Growth Inhibition: Cell Line | Half Effect Drug DFMO | IC50 |
|---|---|---|---|---|---|---|---|
| 1028 | 421.6094 | 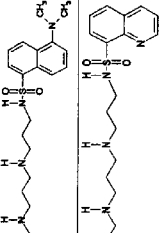 | MDA | 11.4 | MDA | | 50 |
| 1029 | 379.5281 | 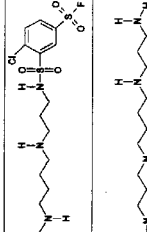 | MDA | 3.4 | MDA | | >300 |
| 1030 | 459.0054 | 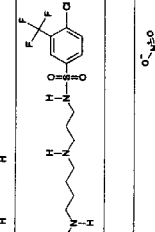 | MDA | 0.08 | MDA | 125 | >250 |
| 1031 | 393.5552 | 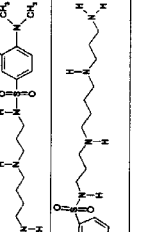 | MDA | 0.43 | MDA | <10 | >300 |
| 1034 | 444.9505 | 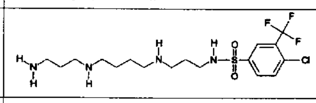 | MDA | 0.24 | MDA | <3 | 50 |
| 1036 | 430.5735 | 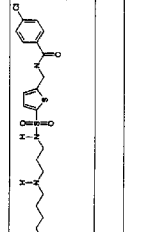 | MDA | 0.84 | mda | 8.7 | 50 |
| | | | | | MDA | | >300 |
| 1041 | 432.5893 | 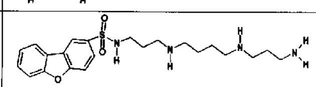 | MDA | 0.066 | MDA | .95 | 12 |
| | | | | | pc-3 | | 6.2 |
| | | | | | caco-2 | | 16.1 |
| | | | | | cem | | 0.79 |
| | | | | | mda | 12.6 | 53.0 |
| | | | | | pc-3 | | 12.4 |
| | | | | | mda | | 46.1 |
| | | | | | pc-3 | | 6.5 |
| 1044 | 516.129 | 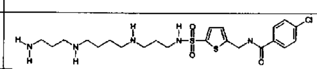 | MDA | 0.156* | MDA | 3 | 180 |
| | | | MDA | 0.0582 | mda | <3.0 | 190 |
| | | | MDA | 0.130 | | | |
| | | | MDA | 0.13 | | | |

Figure 9H-(4)
| ID | mol weight | Structure | Transport: Cell Line | Ki | Growth Inhibition: Cell Line | Half Effect Drug DFMO | IC50 |
|---|---|---|---|---|---|---|---|
| 1045 | 425.6192 | 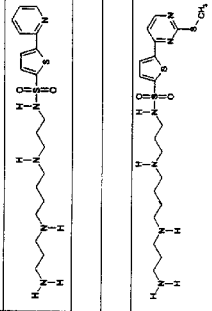 | MDA | 0.228 | MDA | 13 | 180 |
|  |  |  | MDA | 0.164 | mda | 7.3 | 140 |
| 1046 | 472.6979 | 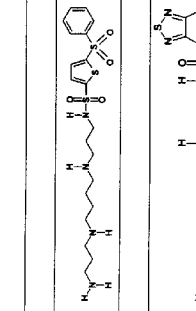 | MDA | 0.32 |  |  |  |
|  |  |  | MDA | 0.44 | mda | 6.92 | 58 |
|  |  |  | MDA | 0.0677 | pc-3 |  | 34.8 |
|  |  |  |  |  | caco-2 |  | >30 |
|  |  |  |  |  | cem |  | 8.9 |
| 1047 | 488.6944 | 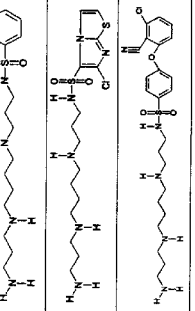 | MDA | 0.375 | mda | 7.3 | 170 |
|  |  |  | MDA | 0.177 |  |  |  |
| 1048 | 400.5686 | 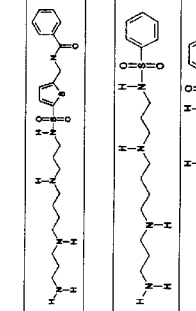 | MDA | 0.421 | mda | 26.7 | >300 |
| 1049 | 423.0024 | 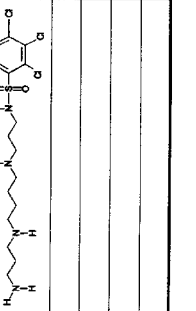 | MDA | > 3 | mda | | >300 |
| 1050 | 494.0602 | 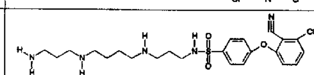 | MDA | 0.108 | MDA | 2.26 | 140 |
|  |  |  | MDA | 0.0537 |  |  |  |
| 1051 | 481.684 | 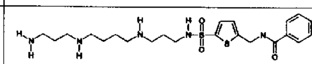 | MDA | 0.28 | mda | 6.5 | >300 |
|  |  |  | MDA | 0.076 |  |  |  |
| 1052 | 342.5071 | 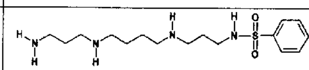 | MDA | 0.16* | MDA | 30 | >300 |
| 1054 | 445.8422 | 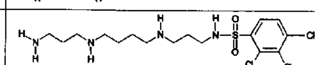 | MDA | 0.025 | mda | <3.0 | 50 |
|  |  |  | MDA | 0.0829 | pc-3 | 7.89 | 20 |
|  |  |  |  |  | caco-2 |  | 19.8 |
|  |  |  |  |  | cem |  | 27.1 |
|  |  |  |  |  |  |  | 2.6 |

Figure 9H-(5)

| ID | mol weight | Structure | Transport: Cell Line | Ki | Growth Inhibition: Cell Line | Half Effect Drug DFMO | IC50 |
|---|---|---|---|---|---|---|---|
| 1057 | 434.7334 | 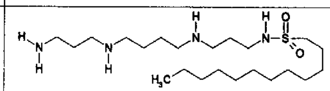 | MDA | 0.17 | mda | | 100 |
| 1058 | 484.7503 | 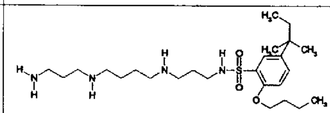 | MDA | 0.17* | mda | | 6 |
| | | | | | pc-3 | | 5.9 |
| | | | | | caco-2 | | 14.8 |
| | | | | | cem | | 0.71 |
| 1070 | 587.7877 | 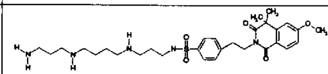 | MDA | > 10 | mda | | 13 |
| | | | | | pc-3 | | >30 |
| | | | | | caco-2 | | >30 |
| | | | | | cem | | >30 |
| 1074 | 437.606 | 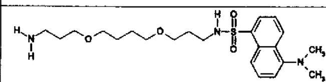 | MDA | > 30 | MDA | | |
| 1075 | 433.6206 | 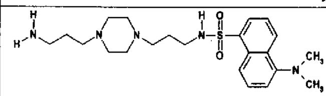 | MDA | > 100 | | | |
| 1082 | 412.6426 | 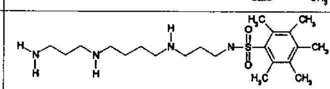 | MDA | > 3 | mda | | 140 |
| 1088 | 278.3758 | 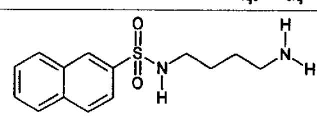 | mda | 5.4* | | | |
| 1103 | 488.6944 | 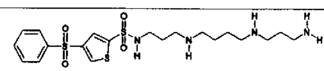 | MDA | 0.067 | mda | 3.5 | 58 |
| 1105 | 557.6804 | 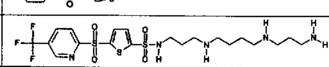 | MDA | 0.083 | mda | | 44 |

Figure 9H-(6)

| ID | mol weight | Structure | Transport: Cell Line | Ki | Growth Inhibition: Cell Line | Half Effect Drug DFMO | IC50 |
|---|---|---|---|---|---|---|---|
| 1106 | 356.5342 | 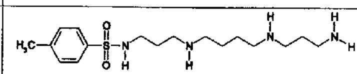 | MDA | 0.094 | mda | | 160 |
| 1108 | 322.5167 | 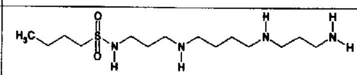 | MDA | 0.19 | mda | | 150 |
| 1130 | 294.4625 | 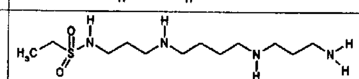 | MDA | 0.22 | mda | >300 | >300 |
| 1330 | 348.5329 | 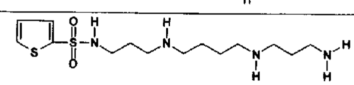 | | | | | |

Figure 9I

N1-monosubstituted polyamines: N1-monosubstituted amines

| ID | mol weight | Structure | Transport>Cell Line | Ki | Growth Inhibtion>Cell Line | Half Effect Drug DFMO | IC50 |
|---|---|---|---|---|---|---|---|
| 1004 | 372.4712 | 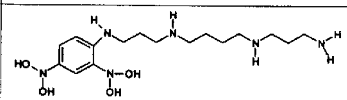 | | | | | |
| 1350 | 316.5374 | 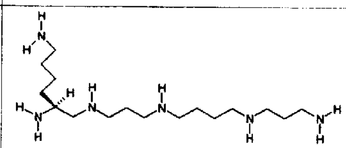 | MDA<br>A172 | 2.2<br>3 | MDA | | 5 |

Figure 9J

N1-monosubstituted polyamines: Other

| ID | mol weight | Structure | Transport>Cell Line | Ki | Growth Inhibition>Cell Line | Half Effect Drug | DFMO IC50 |
|---|---|---|---|---|---|---|---|
| 1021 (urea) | 421.5906 | 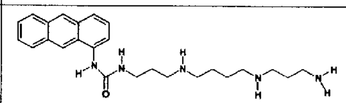 | MDA | 0.44 | MDA | 8.2 | 35 |
| 1042 (urea) | 569.7752 | 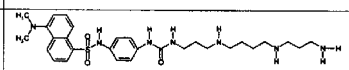 | A172 MDA | .04* 1 | MDA | 14.8 | 100 |
| 1071 | 641.0454 | 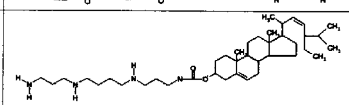 | MDA | | | | |
| 1109 (urea) | 563.8118 | 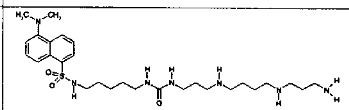 | MDA | 0.0674 | pc-3 | 30 | >100 |
| 1295 (thiourea) | 591.735 | | MDA MDA | 0.090 >3 | mda | 95 | >100 | stereochemistry:
L is S, D is R

| R' | | R' | |
|---|---|---|---|
| -H | Gly | HS-CH2- | Cys |
| -CH3 | Ala | -S-CH2CH3 (CH3-S-CH2-) | Met |
| -CH(CH3)2 | Val | H2N-C(=O)-CH2- | Asn |
| -CH2CH(CH3)2 | Leu | H2N-C(=O)-CH2CH2- | Gln |
| -CH(CH3)CH2CH3 | Ile | HO-C(=O)-CH2- | Asp |
| -CH2-C6H5 | Phe | HO-C(=O)-CH2CH2- | Glu |
| -CH2-C6H4-OH | Tyr | H2N-(CH2)4- | Lys |
| | | H2N-(CH2)3- | Orn |
| -CH2-(indolyl) | Trp | H2N-C(=NH)-NH-(CH2)3- | Arg |
| HO-CH2- | Ser | imidazolyl-CH2- | His |
| CH3-CH(OH)- | Thr | proline | Pro |

A. Reporter and Immobilization handles are both N¹-terminal

B. Reporter Handle is internal and Immobilization handle is N-terminal.

C. Immobilization and Reporter handles are both N¹ and N¹² terminal, respectively

Figure 16A

| ID | Mol Weight | Structure | Transport Cell Line | Ki (µM) | Growth Inhibition Cell Line | Half Effect Drug DFMO (µM) | IC50 (µM) |
|---|---|---|---|---|---|---|---|
| 1092 | 656.9600 | 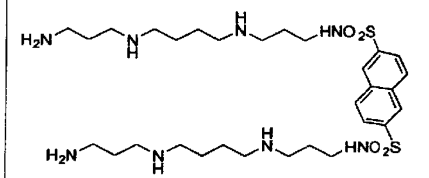 | MDA | 0.079 | MDA | 279 | >300 |
| 1236 | 486.7504 | 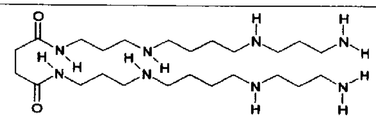 | MDA<br>MDA | 0.0288<br>0.0152 | MDA<br>PC-3 | 6<br>1.8 | >300<br>>300 |
| 1261 | 620.9735 | 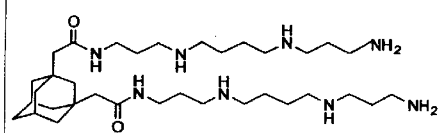 | MDA | 0.402 | | | |
| 1275 | 528.8317 | 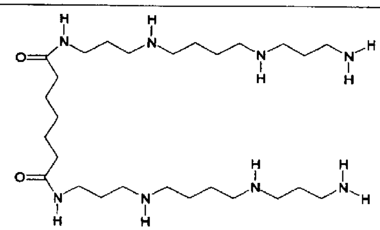 | MDA | 0.219 | | | |
| 1286 | 514.8046 | 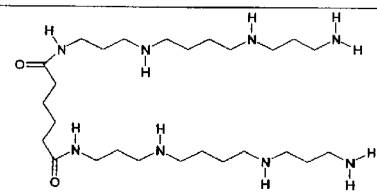 | MDA | 0.0595 | | | |

Figure 16B

| ID | Mol Weight | Structure | Transport Cell Line | Ki (µM) | Growth Inhibition Cell Line | Half Effect Drug DFMO (µM) | IC50 (µM) |
|---|---|---|---|---|---|---|---|
| 1287 | 570.9129 | 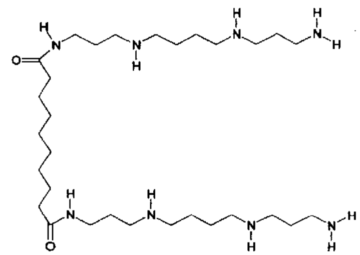 | MDA | 0.0986 | | | |
| 1288 | 500.7775 | 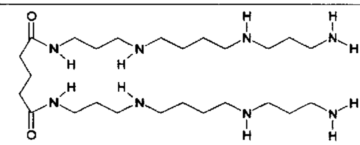 | | | | | |
| 1289 | 542.8587 | 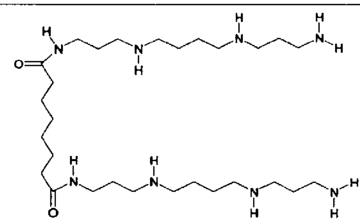 | | | | | |
| 1290 | 556.8858 | 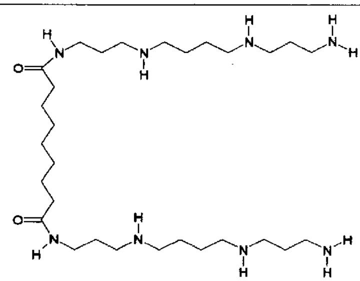 | | | | | |

| ID | Mol Weight | Structure | Transport Cell Line | Ki (µM) | Growth Inhibition Cell Line | Half Effect Drug DFMO (µM) | IC50 (µM) |
|---|---|---|---|---|---|---|---|
| 1299 | 598.9671 | 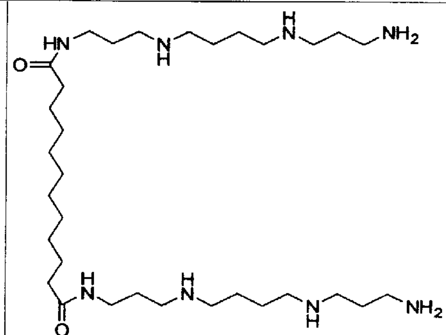 | | | | | |

Bispolyamine derivatives: protected

| ID | mol weight | Structure |
|----|------------|-----------|
| 1262 | 686.9870 | 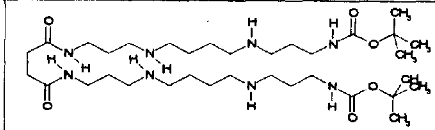 |
| 1263 | 757.1225 | 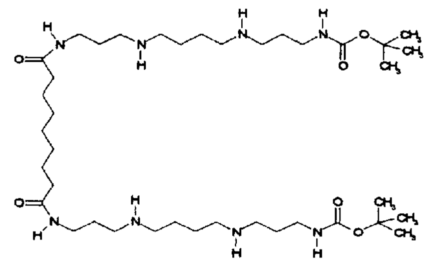 |
| 1264 | 771.1495 | 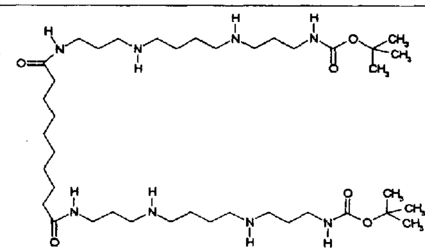 |
| 1265 | 729.0683 | 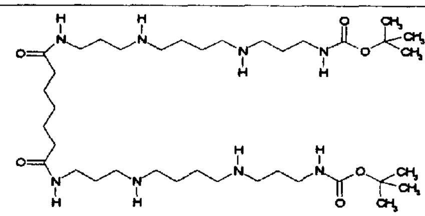 |
| 1267 | 701.0141 | 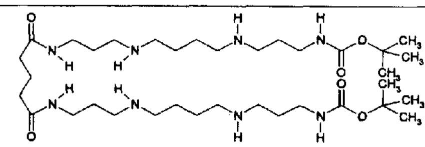 |
| 1268 | 799.2037 | 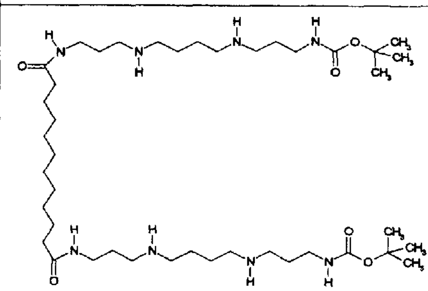 |
| 1269 | 743.0954 | 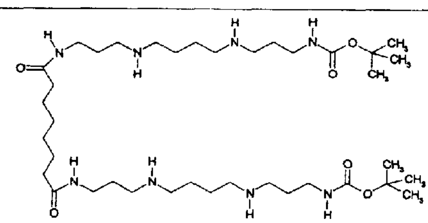 |

Figure 17B
Bispolyamine derivatives: protected

| ID | mol weight | Structure |
|---|---|---|
| 1285 | 715.0412 | 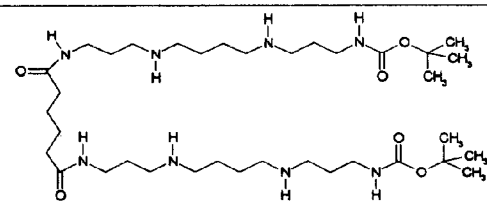 |

POLYAMINE ANALOGUES AS THERAPEUTIC AND DIAGNOSTIC AGENTS

RELATED APPLICATIONS

This is a continuation-in-part of U.S. application Ser. No. 09/341,400, filed Sep. 3, 1999, now U.S. Pat. No. 6,172,261, which is the U.S. national phase application of PCT/US98/14896 filed Jul. 15, 1998, which claims benefit of priority from U.S. Provisional Applications 60/052,586, filed Jul. 15, 1997; 60/065,728, filed Nov. 14, 1997; and 60/085,538, filed May 15, 1998; and a continuation-in-part of U.S. application Ser. No. 09/396,523, filed Sep. 15, 1999, all of which are hereby incorporated by reference as if fully set forth.

FIELD OF THE INVENTION

The invention in the field of chemistry and biochemistry relates to the synthesis and use of novel polyamine transport (PAT) inhibitor compounds with pharmacological or agricultural uses and as probes for biochemical assays or for purification of selected polyamine binding targets. As drugs, these compounds are used to treat disorders of undesired cell proliferation, primarily cancer, alone or combined with other agents such as polyamine synthesis inhibitors.

The invention also relates to the synthesis and use of such novel polyamine compounds as part of combinatorial libraries. These libraries are used to discover compositions that inhibit PAT and/or that bind to a cellular polyamine transporter (PATr). Various members of these libraries or compounds discovered through use of the libraries have utility as drugs, agricultural chemicals, and as probes.

BACKGROUND OF THE INVENTION

Decades of research on the myriad of biological activities that the polyamines, putrescine, spermidine and spermine play in cellular processes have shown the profound role they play in life (Cohen, S. S., "A Guide to the Polyamines" 1998, Oxford University Press, New York). As polycations at physiological pH, they bind tightly to and strongly modulate the biological activities of all of the anionic cellular components. Specific and strong interactions have been associated with DNA and RNA together with their associated chromatin proteins (Tabor, H. et al. 1,4-Diaminobutrane (putrescine), spermidine, and spermine. *Ann Rev. Biochem.* 1976, 45, 285–306; Matthews, H. R. Polyamines, chromatin structure and transcription. *BioEssays*, 1993, 15, 561–566). Spermine has been shown to function directly as a free radical scavenger that protects DNA from insults by reactive oxygen species (Ha, H. C. et al. *Proc. Natl. Acad. Sci. USA*, 1998, 95, 11140–11145). Specific interactions of multicationic polyamines with microtubules has been recently shown (Wolff, J. Promotion of Microtubule Assembly by Oligocations: Cooperativity between Charged Groups. *Biochemistry*, 1998, 37, 10722–10729; Webb, H. K. et al.,*J. Med. Chem.* 1999, in press). Allosteric regulation of membrane-bound enzymes including acetylcholinesterase has been shown (Kossorotow, A. et al. Regulatory effects of polyamines on membrane-bound acetylcholinesterase. *Biochem. J.* 1974, 144, 21–27). Polyamines have a direct influence on many neurotransmitter receptors and ion channels (Carter, C. The Neuropharmacology of Polyamines, 1994, Academic Press, San Diego, Calif.; Williams, K. Interaction of polyamines with ion channels, *Biochem. J.*, 1997, 325, 289–297). Specific polyamine binding sites have also been demonstrated for the NMDA receptor complex (Ransom, R. W. et al. Cooperative modulation of [$^3$H]MK-801 Binding to the N-Methyl-D-Aspartate Receptor-Ion Channel Complex by L-Glutamate, Glycine, and Polyamines.*J. Neurochem.* 1988, 51, 830–836; Williams, K. et al. Minireview: Modulation of the NMDA receptor by polyamines. *Life Sci.* 1991, 48, 469–498).

Many stimuli involved in both normal and neoplastic growth activate the polyamine biosynthetic pathway. A great number of multidisciplinary studies have shown that the intracellular concentrations of the polyamines is highly regulated at many steps in their biosynthesis, catabolism and transport. The fact that cells contain such complex apparatus for the tight control of the levels of these molecules shows that only a very narrow concentration range is tolerated. Ornithine decarboxylase (ODC), the rate-limiting enzyme in polyamine biosynthesis, catalyzes the production of putrescine from its precursor ornithine. This enzyme, with a very short biological half-life, is one of the most inducible mammalian enzymes known (Russell, D. et al. Amine synthesis in rapidly growing tissues: ornithine decarboxylase activity in regenerating rat liver, chick embryo, and various tumors. *Proc. Natl. Acad. Sci. USA*. 1968, 60, 1420–1427). Many biological stimuli involved in cellular growth have been shown to induce this enzyme and a distinct growth advantage is gained by induction of ODC (Alhonen-Hongisto, L. et al. Tumourigenicity, cell-surface glycoprotein changes and ornithine decarboxylase gene pattern in Ehrlich ascites-carcinoma cells. *Biochem. J.* 1985, 229, 711–715). An increase in the activity of ODC has been associated with tumor growth (Jänne, J. et al. Polyamines in rapid growth and cancer. *Biochim. Biophys. Acta* 1978, 473, 241–493; Scalabrino, G. et al. Polyamines in mammalian tumors. Part I. *Adv. Cancer Res.* 1981, 35, 151–268; Scalabrino, G. et al. Polyamines in mammalian tumors. Part II. *Adv. Cancer Res.* 1982, 36, 1–102). Feedback inhibition of ODC activity is mediated by ODC-antizyme protein. Following elevation of polyamine concentrations, a polyamine-stimulated +1 frameshift of the ODC-antizyme mRNA reading frame causes elevation of this ODC-inhibiting protein (Hayashi, S. et al. Ornithine decarboxylase antizyme: a novel type of regulatory protein. *TIBS*, 1996, 21, 27–30; Matsufuji, S. et al. *EMBO Journal*, 1996, 15, 1360–1370). The ODC-antizyme protein binds to ODC with high affinity to form an inactive complex that is then tagged for degradation in an ATP-dependent fashion by the 26S proteosome (Heller, J. S. et al. *Proc. Natl. Aced. Sci. USA*. 1976, 73,1858–1862; Murakami, Y. et al. Ornithine decarboxylase is degraded by the 26S proteosome without ubiquitination. *Nature*, 1992, 360, 597–599). ODC-antizyme also represses the polyamine uptake system of cells (Suzuki, T. et al. Antizyme protects against abnormal accumulation and toxicity of polyamines in ornithine decarboxylase-overproducing cells. *Proc. Natl. Acad. Sci. USA*. 1994, 91, 8930–8934).

The polyamine catabolism pathway is important to prevent the toxic effects of excess polyamines on cells (Seiler, N. Functions of polyamine acetylation. *Can. J. Physiol. Pharmacol.* 1987, 65, 2024–2035; Seiler, N. Polyamine oxidase, properties and functions. *Progress in Brain Res.* 1995, 106, 333–344). This pathway is used by the cell to interconvert the various polyamines and to eliminate excess polyamines before they reach toxic levels. This pathway introduces no additional carbon precursors into the polyamine pool.

Polyamine transport into mammalian cells is energy and temperature dependent, saturable, carrier mediated and operates against a substantial concentration gradient (Seiler, N. et al. Polyamine transport in mammalian cells. *Int. J Biochem.* 1990, 22, 211–218; Khan, N. A.; Quemener, V. et al.

Characterization of polyamine transport pathways, in *Neuropharmacology of Polyamines* (Carter, C., ed.), 1994, Academic, San Diego, pp. 37–60). Ample experimental proof exists that polyamine concentration homeostasis is mediated via this transport system. Changes in the requirements for polyamines in response to growth stimulation is reflected by increases in the transport activity. Stimulation of human fibroblasts to cell proliferation by serum or epidermal growth factor was followed by an 18–100 fold increase in the uptake of putrescine (DiPasquale, A. et al. Epidermal growth factor stimulates putrescine transport and ornithine decarboxylase activity in cultures human fibroblasts. *Exp. Cell Res*. 1978, 116, 317–323; Pohjanpelto, P. Putrescine transport is greatly increased in human fibroblasts initiated to proliferate. *J. Cell Biol*. 1976, 68, 512–520). Tumors have been shown to have an increased rate of putrescine uptake (Volkow, N. et al. Labeled putrescine as a probe in brain tumors. *Science*, 1983, 221, 673–675; Moulinoux, J-P. et al. Biological significance of circulating polyamines in oncology. *Cell. Mol. Biol*. 1991, 37, 773–783). Inhibition of polyamine biosynthesis in cells in culture by α-difluoromethylornithine (DFMO), a well-studied mechanism-based inhibitor of ODC, causes a substantial depletion of intracellular putrescine and spermidine with resultant cell growth inhibition. Upon supplementing the culture media with exogenous polyamines this depletion causes transport activity to rise several-fold (Bogle, R. G. et al. Endothelial polyamine uptake:. selective stimulation by L-arginine deprivation or polyamine depletion. *Am. J. Physiol*. 1994, 266, C776–C783; Alhonen-Hongisto, L. et al. Intracellular putrescine deprivation induces uptake of the natural polyamines and methylglyoxal bis (guanylhydrazone). *Biochem. J*. 1980, 192, 941–945). The cells then returned to their original rate of growth.

Several experimental lines of evidence support the conclusion that increased effectiveness of ODC inhibition can be obtained by interfering with the polyamine transport apparatus. A mutant L1210 leukemia cell line was shown to have greatly reduced polyamine transport activity following selection for resistance to methylglycoxal bis (guanylhydrazone) (MGBG), an extremely cytotoxic AdoMetDC inhibitor that is taken up by the same transport system as the polyamines. Mice inoculated with these cells had a much greater response to DFMO treatment (87% increase in median survival time; 13 of 40 mice cured) than mice inoculated with the parental cell line (22% increase in median survival time). See Persson, L. et al. Curative effect of d,1-2-difluoromethylornithine on mice bearing mutant L1210 leukemia cells deficient in polyamine uptake. *Cancer Res*. 1988, 48, 4807–4811. A significant source of extracellular polyamines is produced by the microbial flora in the gastrointestinal tract (Sarhan, S. et al. The gastrointestinal tract as polyamine source for tumor growth. *Anticancer Res*. 1989, 9, 215–224). When this source of polyamines is removed by decontamination of this flora, DFMO's previous moderate growth inhibitory effects on Lewis lung carcinoma cells or L1210 zenografts is markedly potentiated (Hessels, J. et al. Limitation of dietary polyamines and arginine and the gastrointestinal synthesis of putrescine potentiates the cytostatic effect of a-difluoromethylornithine in L1210 bearing mice. *Int. Symp. Polyamines in Biochemical and Clinical Research*, Sorrento (Italy), 1988, Abstr. P105). An additional source of polyamines is from dietary sources (Bardocz, S. et al. Polyamines in food; implications for growth and health. *J. Biochem Nutr*. 1993, 4, 66–71). By feeding a polyamine-free diet to DFMO-treated nude mice the MCF-7 human breast cancer zenografts contained greatly reduced levels of putrescine in comparison to DFMO treatment alone (Lêveque, J. et al. The gastrointestinal polyamine source depletion enhances DFMO induced polyamine depletion in MCF-7 human breast cancer cells in vivo. *Anticancer Res*. 1998, 18, 2663–2668). In additional animal models, complete polyamine deprivation also enhanced DFMO's growth inhibitory effectiveness (Moulinoux, J. P. et al. Inhibition of growth of the U-251 human glioblastoma in nude mice by polyamine deprivation. *Anticancer Res*. 1991, 11, 175–180; Quemener, V. et al. Polyamine deprivation enhances antitumoral efficacy of chemotherapy. *Anticancer Res*. 1992, 12, 1447–1454; Chamaillard, L. et al. Polyamine deprivation prevents the development of tumour-induced immune suppression. *Br. J. Cancer* 1997, 76, 365–370).

The Polyamine Transporter (PATr)

The increased demand for polyamines by rapidly growing, transformed cancer cells is only partially met by an increased rate of synthesis. To exploit this increased need for polyamines, synthesis inhibitors have been sought. Additionally, lowering polyamine concentrations can result in aberrations in chromatin structure leading to cell death or inhibition of proliferation (Quemener, V. et al., *Anticancer Res*. 14:443–448, 1994; Porter, C. W. et al, *Cancer Res*. 53:581–586, 1993). It has become increasingly apparent that the initial disappointing results observed in the clinic with polyamine synthesis inhibitors arises from compensatory increases in transport of polyamines by a specific active transport system (Seiler, N. et al., *Int. J. Biochem*. 22:211–218, 1990; Seiler, N. et al, *J. Biochem. Cell Biol*. 28:843–861, 1996). The promising results observed in cell culture with a suicide substrate inhibitor of ornithine decarboxylase, α-difluoromethylornithine (DFMO), or with an inhibitor of S-adenosylmethionine decarboxylase, methylglyoxal bis(guanylhydrazone) (MGBG) did not transfer to human clinical trials (Schecter, P. J. et al., In *Inhibition of Polyamine Metabolism. Biological Significance and Basis for New Therapies*; McCann, P. P. et al., eds; 1987, pp 345–364). Since the only two avenues for carbon transfer into polyamine pools are synthesis or transport, simultaneous inhibition of both of these pathways is considered by the present inventors to be a promising anti-cancer therapeutic approach.

A study confirming the validity of this chemotherapeutic approach used transplanted murine L1210 leukemia cells that were deficient in PAT. Mice transplanted with the wild-type L1210 cancer cells (with intact PAT) died after 12 days, even when treated with DFMO. In contrast, DFMO mice transplanted with PAT-deficient L1210 cells lived longer than 60 days (Ask, A. et al., *Cancer Lett*. 66:29–34, 1992). These authors also showed that treatment of mice harboring wild-type L1210 cells with a combination of (1) DFMO (2) a low polyamine diet and (3) antibiotics (which decrease polyamine production by gut flora) resulted in prolonged survival compared to treatment with DFMO alone.

Augmented PAT into cancer cells promotes cell killing. J. L. Holley et al. (*Cancer Res*. 52:4190–4195, 1992) showed up to a 225-fold increase in cytotoxicity of a chlorambucil-spermidine conjugate compared to chlorambucil alone. A series of nitroimidazole-polyamine conjugates were also effective (Holley, J. L. et al., *Biochem. Pharmacol*. 43:763–769, 1992). Others showed that mice infected with a multi-drug resistant strain of malaria were cured by treatment with a chloroquinoline-putrescine conjugate (Singh, S. et al., *J. Biol. Chem*. 272:13506–13511, 1997).

Thus, the effectiveness of cytotoxic compounds could be enhanced by their conjugation with polyamines. These effects may have been due to the exploitation of the PAT system to deliver these compounds into cancer cells.

The gene for the polyamine transport protein has been cloned from *Escherichia coli* and recently from yeast (Kashiwagi, K. et al. *J. Biol. Chem.* 1990, 265, 20893–20897; Tomitori, H. et al. Identification of a gene for a polyamine transport protein in yeast. *J. Biol. Chem.* 1999, 274, 3265–3267). The genes for the mammalian transporter await identification. The transporter from *E. coli* has been crystallized and its X-ray structure has been determined (Sugiyama, S. et al. Crystal structure of PotD, the primary receptor of the polyamine transport system in *Escherichia Coli*. *J. Biol. Chem.* 1996, 271, 9519–9525). This structure represents one of only a few but growing number determined for spermidine-binding proteins. Since this structure was determined on a prokaryotic species its use in the design of mammalian transport inhibitors was deemed to be of limited value. Despite this, several insights were obtained and used through analysis of this structure. In addition to the expected presence of carboxylate residues positioned to form salt bridges with the protonated amino groups of spermidine, numerous aromatic residues, especially tryptophan residues appeared to strengthen hydrophobic interactions with the methylene groups of the substrate. Additionally, a $H_2O$ molecule was positioned at one end of spermidine substrate, providing stronger interactions with the ionic residues in this position.

Several researchers have studied the ability of polyamine analogs to inhibit the uptake of $^3$H-spermidine into cells. Bergeron and coworkers studied the effect of addition of different alkyl group substitution on the terminal nitrogen atoms of spermidine or spermine analogs (Bergeron, R. J. et al. Antiproliferative properties of polyamine analogues: a structure-activity study. *J. Med. Chem.* 1994, 37, 3464–3476). They showed larger alkyl groups diminished the ability to prevent uptake of radiolabeled spermidine. They later concluded that increases in the number of methylenes between the nitrogen atoms decreased the ability to compete for $^3$H spermidine uptake (Bergeron, R. J. et al. A comparison of structure-activity relationships between spermidine and spermine antineoplastics *J. Med. Chem.* 1997, 40, 1475–1494). Of greater importance to the present work was their conclusion that the polyamine transport apparatus requires only three cationic centers for polyamine recognition and transport (Porter, C. W. et al. *J. Cancer Res.* 1984, 44, 126–128). Two groups analyzed literature examples of the polyamine analogs ability to inhibit $^3$H spermidine uptake into L1210 cells by CoMFA and QSAR methods (Li, Y. et al. Comparative Molecular field analysis-based predictive model of structure-function relationships of polyamine transport inhibitors in L1210 cells. *Cancer Res.* 1997, 57, 234–239; Xia, C. Q. et al. QSAR analysis of polyamine transport inhibitors in L1210 cells. *J. Drug Target.* 1998, 6, 65–77).

Polyamine Transport (PAT) Assays

There is no known high-throughput assay for measuring PAT. A radiochemical assay is used for biochemical analysis of transport and has been used to study PAT in yeast and a variety of mammalian cells (Kakinuma, Y. et al., *Biochem. Biophys. Res. Comm.* 216:985–992, 1995; Seiler, N. et al., *Int. J. Biochem. Cell Biol.* 28:843–861, 1996). See, for example Huber, M. et al. *Cancer Res.* 55:934–943, 1995.

The radiometric assay uses radiolabeled polyamines such as putrescine, spermidine or spermine, but, due to the low signal, large numbers of adherent or non-adherent cells are required. Additional care is required with spermine due to its non-specific adsorption to cells and plastics. Cells are mixed with the test compounds and the radiolabeled polyamine to initiate the assay. The cells are incubated for 1–60 minutes, depending on cell type. The assay is terminated by removal of the medium and cooling the plates to 4° C. The cells are then washed with cold medium three times, dissolved in 0.1% sodium dodecyl sulfate and the radioactivity in solution is then determined by scintillation counting. This assay is difficult to scale up to a high throughput procedure due to the low signal from the radiolabel and the handling requirements inherent in procedures with radioactivity.

A great number of polyamine amide natural products have been recently been discovered in the venom of arthropods such as spiders and wasps. These acylpolyamine analogs have been shown to have specific and strong interactions with the neuromuscular junctions of insects (Moya, E. et al. Syntheses and neuropharmacological properties of arthropod polyamine amide toxins. *Neuropharmacology of Polyamines* (Carter, C., ed.), 1994, Academic, San Diego, pp. 167–184). With this capability these toxins give the insect predators the ability to paralyze or kill their prey. Most of these natural products have the common molecular features of a polyamine moiety (many with structurally diverse polyamine analogs) connected through an amide with an aromatic amino acid structural analog. Simpler synthetic analogs have been sought that attempt to maximize interactions with either crustacean neuromuscular synapses or mammalian glutamate receptors (Asami, T. et al. Acylpolyamines mimic the action of Joro spider toxin (JSTX) on crustacean muscle glutamate receptors. *Biomedical Res.* 1989, 10, 185–189; Raditsch, M. et al. Polyamine spider toxins and mammalian N-methyl-D-aspartate receptors. Structural basis for channel blocking and binding of argiotoxin$_{636}$. *Eur. J. Biochem.* 1996, 240, 416–426; Tsubokawa, H. et al. Effects of a spider toxin and its analogue on glutamate-activated currents in the nippocampal CA1 Neuron after ischemia. *J. Neurophys.* 1995, 74, 218–225).

Citation of the above documents is not intended as an admission that any of the foregoing is pertinent prior art. All statements as to the date or representation as to the contents of these documents is based on the information available to the applicant and does not constitute any admission as to the correctness of the dates or contents of these documents.

SUMMARY OF THE INVENTION

The present invention is directed to various polyamine analogues and derivatives and their use as drugs, as agricultural or as environmentally useful agents. The invention defines sites and structures within these compounds that are key to their binding (and polyamine binding) to membrane (and soluble) proteins, particularly the PATr.

The compositions of the present invention include polyamine derivatives substituted at one or more positions. Monosubstituted polyamines are preferably substituted at a terminal nitrogen, but may be alternatively or additionally substituted at internal nitrogen and/or internal carbon atoms.

A preferred embodiment is a highly specific PAT inhibitor with pharmaceutical utility as an anti-cancer chemotherapeutic. These include polyamine derivatives comprised of two linear polyamines linked to each other. The two polyamines may be identical or different and may be substituted at an internal carbon and/or nitrogen atom. Preferably, one terminal position of each polyamine is used in the linkage. The other terminal position may also be substituted.

Preferred substituents are structures that increase binding affinity or otherwise enhance the irreversibility of binding of the compound to a polyamine binding molecule, such as the PATr, an enzyme or DNA. Such additional substituents include the aziridine group and various other aliphatic, aromatic, mixed aliphatic-aromatic, or heterocyclic multi-ring structures. Reactive moieties which, like aziridine, bind irreversibly to a PATr or another polyamine binding molecule, are also within the scope of this invention. Examples of reactive groups that react with nucleophiles to form covalent bonds include chloro-, bromo- and iodoacetamides, sulfonylfluorides, esters, nitrogen mustards, etc Such reactive moieties are used for affinity labeling in a diagnostic or research context, and subserve pharmacological activity as sites within a drug that inhibit PAT or polyamine synthesis. The reactive group can be a reactive photoaffinity group such as an azido or benzophenone group. Chemical agents for photoaffinity labeling are well-known in the art (Flemming, S. A., *Tetrahedron* 51:12479–12520, 1995). Photoreactive compounds for cancer treatment are also known in the art.

More specifically, a polyamine analogue or derivative of the invention includes one that binds to a polyamine-binding site of a molecule and/or inhibits polyamine transport, and has the formula

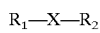

wherein $R_1$ and $R_2$ are each a polyamine, or analogue or derivative thereof; and X is a linker moiety connecting the two polyamines.

Polyamine analogues or derivatives, preferably having a reactive group at one end, may also be employed as assay or biochemical probes.

Additional substituents which may be present on the polyamine portion of analogues or derivatives (with or without a reporter group), are structures which increase binding affinity, or otherwise enhance the irreversibility of binding of the compound to a polyamine binding molecule, such as a PATr, an enzyme or DNA. Such additional substituents include the aziridine group and various other aliphatic, aromatic or heterocyclic multi-ring structures.

A reactive moiety, which, like aziridine, can bind irreversibly to a PATr or another polyamine binding molecule is also contemplated. Examples of groups which react with nucleophiles to form covalent bonds include chloro-, bromo- and iodoacetamides, sulfonylfluorides, esters, nitrogen mustards, etc Such reactive moieties are used for affinity labeling in a diagnostic or research context, and subserve pharmacological activity as parts of drugs that inhibit PAT or polyamine synthesis. The reactive group can also be a reactive photoaffinity group such as an azido- and benzophenone group. Chemical reagents in photoaffinity labeling are well-known (Flemming, S. A., *Tetrahedron* 51:12479–12520, 1995). Moreover, photoreactive compounds for cancer treatment are known in the art.

The polyamine analogues and derivatives of the invention may be categorized in a variety of ways. One category of polyamine analogues and derivatives is the bispolyamines, which may be viewed as analogues or derivatives containing two linked polyamines, which may be identical or different. In preferred embodiments, the individual polyamine groups are linear and have two terminal amino groups. Examples of such polyamines include the naturally occurring polyamines: putrescine, spermidine, and spermine. One terminal amino group in each of such polyamines may be used in the linkage between the two individual polyamines. The remaining terminal amino group may be left as an amine group or further derivatized.

Examples of polyamines for linkage into bispolyamines include $N^1$-dansylspermine (also termed monodansylspermine or MDS (1), $N^1$-dansylspermidine (also termed monodansylspermidine or MDSd, $N^1$-[($N^6$-dansyl)-6-aminocaproyl]spermine (termed DACS, 4), $N^1$-[($N^6$-dansyl)-6-aminocaproyl]spermidine (DACSd), $N^1$-[($N^6$-5-(4-chlorobenzamidomethyl)-thiophene-2-sulfonyl)-6-aminocaproyl]spermine 5 or $N^1$-[($N^6$-(2-dibenzofuransulfonyl)-6-aminocaproyl]spermine 6.

Additional polyamines for linkage into bispolyamines include $N^1$-acyl aminoacid-spermine conjugates. These include natural and non-natural amino acid amides of spermine which are by themselves very effective polyamine transport inhibitors. Examples of such polyamines include L-Lys-spermine (compound 1202), L-Val-spermine (compound 1157) and L-Orn-spermine (compound 1224).

More polyamines for linkage into bispolyamines are acyl polyamines, such as $N^1$-monosubstituted. Monosubstituted polyamines can be further classified into categories such as amides, sulfonamides, $N^1$-monosubstituted amines and other. Among the amides, further classification into those without linkers, those with linkers, amino alkyls, and amino acid head groups is possible. The amino acid head groups can be further categorized as those that are protected, natural α-amino acids, non-natural α-amino acids, and amino acid derivatives.

Once a polyamine analogue which inhibits polyamine transport at a desirable level has been identified, it can readily be further optimized by structural and functional comparisons with other polyamine analogues in the same or different categories to improve its utility. Examples of such improvements include, but are not limited to, increased inhibitory activity, enhanced metabolic stability, enhanced specificity, ease of handling and administration, binding affinity, non-incorporation into cellular polyamine pools, and decreases in side effects.

The present invention is also directed to a pharmaceutical composition useful for treating a disease or condition in which the inhibition of polyamine transport is desirable, comprising a composition as described above and a pharmaceutically acceptable excipient. The pharmaceutical composition may further include an inhibitor of polyamine synthesis; preferably DFMO. Other combinations include the above pharmaceutical composition and one or more additional agents known to be useful for treating said disease or condition This invention also provides a method for treating a disease or a condition in a subject associated with undesired cell proliferation and/or which is treatable by inhibition of polyamine transport, comprising administering to said subject an effective amount of a pharmaceutical composition as described above. The undesired cell proliferation may be associated with proliferation of cells of the immune system, cell of the vascular neontima, tumor cells or with undesired angiogenesis. Preferred diseases to be treated as above include cancer or post-angioplasty injury.

Thus the analogues and derivatives of the invention, alone or in combination with other agents, may be used for the treatment of cancer and other diseases of unwanted cellular proliferation, including angiogenesis and post-injury cell growth. Preferably, such treatments act by inhibiting PAT, deoxyhypusyl synthase, or cell growth or by the induction of apoptosis. As such, they may act by cytostatic and/or cytotoxic mechanisms. The analogues and derivatives of the invention, individually or in combinations with or without other agents, may also be used to treat hypertension, osteoporosis, Alzheimer's disease, ischemia, autoimmune diseases, psychosis, depression, strokes, cardiovascular disease, infection with microorganisms or parasites, plant pathogens including fungi. Cellular processes susceptible to inhibition by the analogues and derivatives of the invention, alone or in combination with other agents, include those involving nucleic acids (DNA or RNA), such as replication, transcription or translation. The analogues and derivatives of the invention may also be efficacious as anti-diarrheal, anti-peristaltic, anti-spasmodic, anti-viral, anti-psoratic and insecticidal agents.

The invention is also directed in part to rapid and efficient testing of many such analogues and derivatives for their transport into cells. By creating a database of structure-activity-relationships (SARs) of such analogues and derivatives, the invention identifies elements that are key for polyamine binding to membrane proteins such as PATr or soluble proteins. With such information, the invention permits predictions as to the transportability and activity of novel polyamine analogues and derivatives.

The polyamine analogues and derivatives of the invention may also be employed as assay or biochemical probes. A preferred assay method employs a polyamine analogue or derivative with a moiety that serves as a detectable label (a "reporter"), preferably a fluorophore, most preferably the dansyl group, or another substituent that can be detected through a variety of means, including by ELISA. A preferred assay method employs an analogue or derivative immobilized to a solid support.

The present invention is also directed to a series of polyamine analogues useful in diagnostic compositions. Methods for the synthesis of such compounds are also described.

Details concerning SARs databases, the use of polyamine analogues as assay probes, and diagnostic compositions are set forth in PCT/US98/14896.

The invention further identifies elements that are key for polyamine binding to membrane proteins such as the PATr (PATr), and to soluble proteins.

BRIEF DESCRIPTION OF THE DRAWINGS

FIGS. 9a to 9j contain tables classifying a large number of $N^1$-monosubstituted polyamines which may be used to form bispolyamines of the invention.

DETAILED DESCRIPTION

Figure 1:
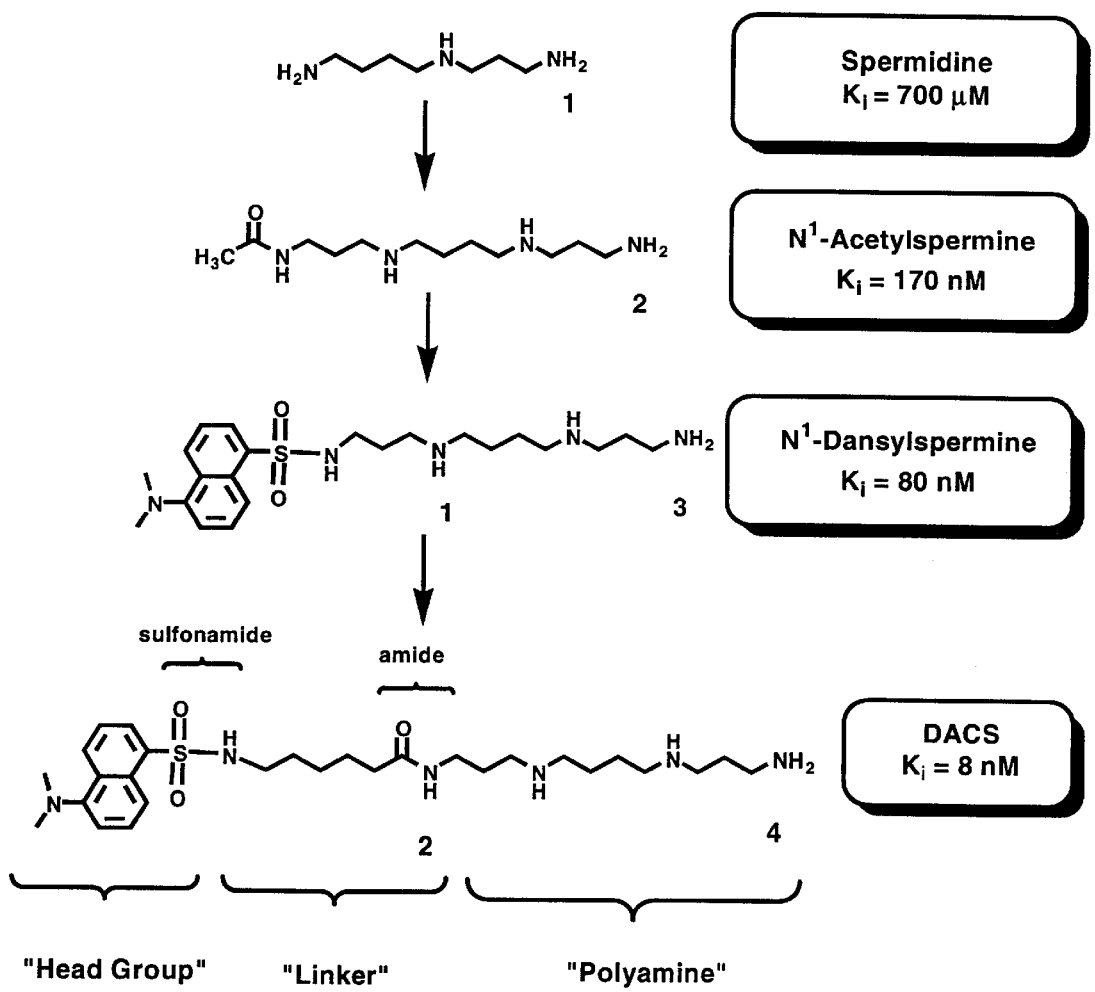
FIG. 1 shows the structure and activity relationships (SAR) between spermidine, MDS and DACS. $K_i$ values are the inhibitory constants obtained in a PAT inhibition assay.
Figure 2D:
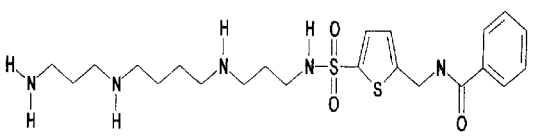
FIG. 2 is a tabular representation of a large number of chemical structures 3–98 that were tested for their effects on cell growth. R, an index of growth inhibitory activity, is the ratio of the growth of cells in the presence of the test compound to the growth in the presence of the compound plus DFMO. The $K_i$, (inhibition constant) reflects a compound's inhibition of PAT in cell culture. These biological effects provide a basis for SAR analysis.
Figure 2D:
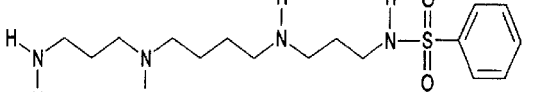
Figure 2D:
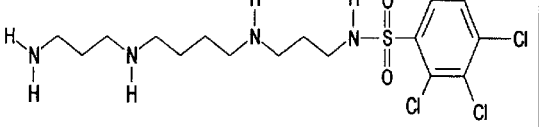
Figure 2D:
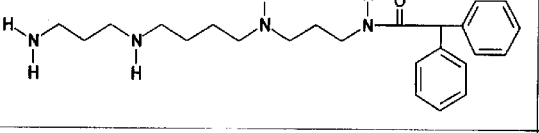
Figure 2D:
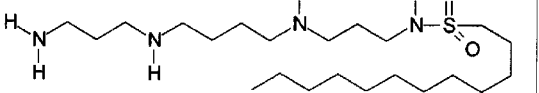
Figure 2D:
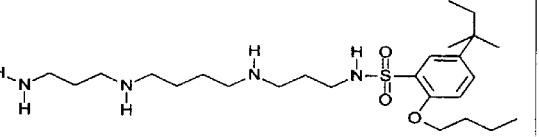
Figure 2D:
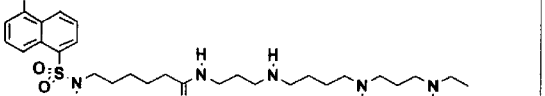
Figure 2D:
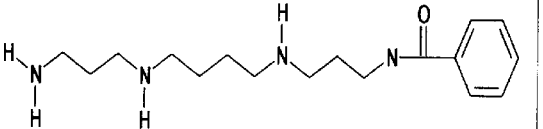
Figure 2D:
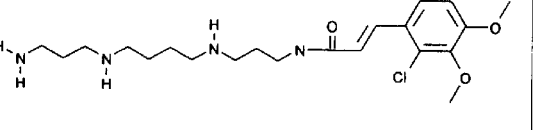
Figure 2K:
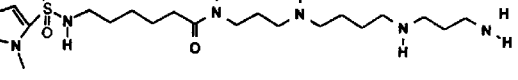
Figure 2K:
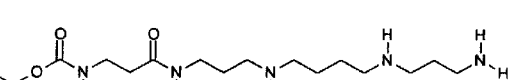
Figure 2K:
Figure 2K:
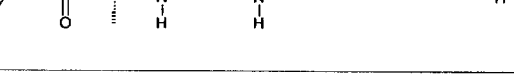
Figure 2K:
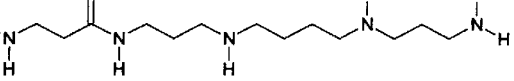
Figure 2K:
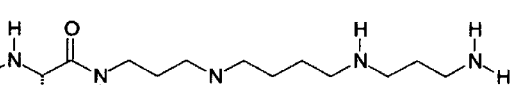
Figure 2K:

The present inventors have designed novel compounds for therapeutic uses and have devised tests using such compounds as probes for measuring PAT and polyamine binding in an efficient, high throughput assay. Using the novel methods, they have screened for and discovered compounds with high affinity for the PATr that inhibit uptake, both competitively and non-competitively. Such compounds are useful as drugs in a number of diseases, particularly cancer. They can also be used as a component of novel drug combinations with, for example, a polyamine synthesis inhibitor such as DFMO (which inhibits ornithine decarboxylase) or with other agents. The compounds of the present invention are also useful in other diseases or conditions in which polyamines play a role as described above, and have agricultural and environmental uses.

The inventors found that formation of a bispolyamine from individual polyamines give it advantageous properties as an inhibitor of PAT or as a probe in an assay of PAT and for drug screening. Such chemical modification does not destroy the effective binding and, in fact, may enhance the affinity of the derivatized polyamine for the PATr. Hence, these compounds are useful for discovery of inhibitors of polyamine uptake.

Definitions

As used herein, the term "polyamine" includes putrescine, spermine or spermidine, as well as longer linear polyamines, branched polyamines, and the like, which may have between 2 and about 10 nitrogens. Also included in this definition are polyamine derivatives or analogues comprising a basic polyamine chain with any of a number of functional groups bound to a C atom or a terminal or internal N atom. A polyamine derivative may include a terminal linker or spacer group between the polyamine core and a derivatizing function.

A "head group" is defined as a moiety bonded either directly to the polyamine or attached to a linker that is bonded to the polyamine. It is preferably an aromatic or heterocyclic group, although aliphatic groups or aroalkyl groups are included. Thus, a head group may be a fluorescent moiety, which also serves as a "reporter."

An "inhibitor" moiety or group is a chemical group derivatizing a polyamine that (1) causes the derivative to bind to the PATr with higher affinity than does a native polyamine and/or (2) by other means blocks the uptake of a polyamine (or a probe of this invention) into a cell or a subcellular PATr preparation. The inventors disclose herein compounds that efficiently inhibit PAT in MDA-MB-231 human breast carcinoma cell and other cells. A number of different types of such inhibitors have been synthesized; various of the synthetic schemes are disclosed herein.

A "reporter moiety" is a chemical moiety forming part of a probe which renders the probe detectable (either directly or, for example, through enzymatic enhancement) and hence permits the determination of the activity of the PATr to which the probe binds. A reporter is detectable either because it itself emits a detectable signal, or by virtue of its affinity for a reporter-specific partner which is detectable or becomes so by binding to, or otherwise reacting with, the reporter. In a preferred embodiment the polyamine analogue is immobilized to a solid support which enables removal of the analogue and any interacting/binding molecules from a complex mixture.

The various inhibitor compounds disclosed herein are identified by various numerical designations, including a counting scheme (using values from 1 to 166 and above) and an identifier number scheme (using four digit compound numbers alone or in combination with an "ORI" or "Ori" identifier). Irrespective of what identifying scheme is used, the identifier merely represents the actual molecular structure of the compound involved and imposes no limitation on said compound.

Overview of Structure-Activity Relationships (SARs)

The PAT inhibitors were developed by modification of the natural substrate of the transporter, spermidine. The present inventors discovered that introduction of a 3-amidopropyl group to the diaminobutyl part of spermidine produced a significantly better transport inhibitor as shown in FIG. 1. The optimal amido or sulfonamide substituent was found to be a medium sized aromatic group, leading to the invention of $N^1$-dansylspermine (MDS) as both a transport inhibitor and a transport assay reporter molecule. MDS has increased binding affinity to cells compared to spermidine and $N^1$-acetylspermine. Significantly enhanced inhibition of cell growth and PAT resulted from the introduction of a 6-carbon atom linker between the aromatic "head" group of MDS and the polyamine core. This new molecule, $N^1$-[($N^6$-dansyl)-6-aminocaproyl]spermine (or DACS) 4, is one of the most potent PAT inhibitors known. In its interaction with biological systems, DACS shows many of the desired properties set forth above. The present inventors have studied DACS and other related analogues extensively.

The SARs around DACS 4 as a lead compound have been explored extensively as shown in FIG. 2 (in particular, compounds 73–98). As discussed above, changes were made in each of several regions of DACS, and effects on transporter binding were measured. The impact of changing the aromatic "head" group was explored by synthesizing a number of different activated 4-nitrophenyl esters with different aromatic and non-aromatic N-sulfonamides at the distal amino end. Another series of "headless" analogues were synthesized to explore the importance of the hydrophobic aromatic grouping. In sum, the present inventors have designed and synthesized a large number of compounds that efficiently inhibit PAT. As described herein, all mono, di and multi-substituted polyamines with the various substituents are intended for use as drugs.

$N^1$-substituted polyamine analogues may be prepared as described in related applications U.S. Ser. Nos. 09/341,400 and 09/396,523, which often presents representative reactions with spermine as a non-limiting example of a polyamine core for use in the present invention. The preferred mono-protected polyamine intermediates for use in preparing bispolyamines were the amino terminal tBoc derivatives produced according to Blagbrough et al, (*Tetrahedron Lett.* 35:2057–2060, 1994), using di-tert-butyldicarbonate in tetrahydrofuran.

Lead polyamine analogue compounds may be further modified to produce analogues for the production of bispolyamines. For example, following structural explorations around the amide, sulfonamide or urea substituent, it was determined that introduction of a six carbon, straight chain aliphatic linker between the polyamine core and the head group led to a 10-fold increase in binding to the PATr (see FIG. 1). Given the high affinity this compound, DACS 4, to its biological target, it was selected as a lead compound for further modification. Methods for the further derivatization of this lead compound is described in related applications U.S. Ser. Nos. 09/341,400 and 09/396,523.

A fruitful general approach to realize selectivity of binding to a target (e.g., protein) of interest has been to synthesize conformationally or stereochemically defined analogues of a binding molecule. By significantly reducing the number of possible rotomers or conformations a molecule can adopt, one can attain increased binding to the desired site. Since the molecule no longer has to search the entire "conformational space," its energy of interaction with the target increases many times.

Figure 10:
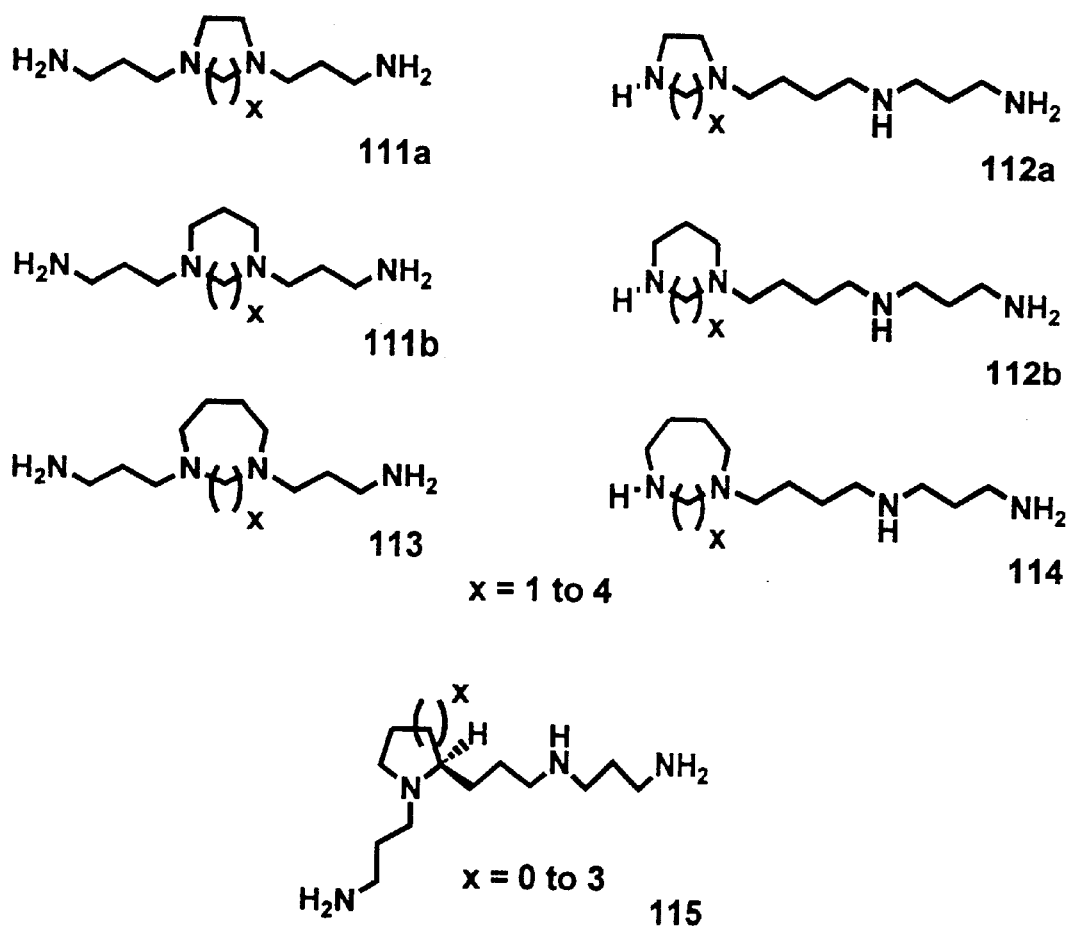
FIG. 10 shows four classes (11–114) of conformationally restricted polyamine analogues, and at the bottom, a stereochemically defined, internally cyclic polyamine analogues (116) that may be used in the preparation of the bispolyamines of the invention.

Others have tried to solve the selectivity problem with polyamine analogues by synthesizing conformationally restricted analogues. Ganem replaced the butyl portion of spermine with 2-butene and 2-butyne diamino derivatives (Ganem, B., *J. Org. Chem.* 1987, 52, 5044–5046). Rajeev, K. G. et al., *J. Org. Chem.* 1997, 62, 5169–5173, incorporated a stereochemically defined, conformationally restrained pyrrolidine ring into the spermine backbone (FIG. 10; 115, x=1) Brand, G. et al., *Tetrahedron Lett.* 1994, 35, 8609–8612, synthesized cyclopolyamine analogues of spermidine and spermine. See, for example FIG. 10 (113, x=3, 4, and 5). The present inventors extended this work by producing the other analogues shown in FIG. 10. These analogues are synthesized using variations of known methods. The analogues where x=1 are produced by reacting spermine or N,N'-bis(3-aminopropyl)-1,3-propanediamine with formaldehyde as described by Ganem, B., *Acc. Chem. Res.*, 1982, 15, 290). The primary amines are protected as N-tBoc derivatives for the analogues 111 and 113. Acid deprotection then gives the desired products. The derivative 112, where x=1, was also synthesized Ganem.

Analogues 111 and 113 (FIG. 10), where x=2 to 4, were produced by reductive alkylation. $N^1,N^{14}$-Bis(tBoc) spermine was reacted with the dialdehyde, $OHC(CH_2)_{x-2}CHO$ and $NaBH_4$ in EtOH. Compounds 112 and 114 were made by the same procedure on a suitable $N^1,N^4$-bisprotected spermine derivative.

Stereochemically defined, internally cyclic structures (FIG. 10, 115) are synthesized using an intermediate aldehyde produced from the corresponding alcohol. This protected alcohol can be oxidized to the aldehyde using Swern conditions. Aldehyde extension by the Wittig reaction with formylmethylene triphenylphos-phorane, followed by reduction (overreduced alcohol can be reoxidized to the aldehyde using pyridinium chlorochromate) and reductive amination/cyclization completed the sequence to make the analogues where x=2. By Wittig reaction with 3-bromopropyl triphenylphosphonium bromide, deprotection and intramolecular alkylative cyclization, the analogue where x=3 can be produced. Either stereoisomer can be produced by starting with L- or D-ornithine. Polyamines containing a guanidinium group are synthesized according to Iwanowicz, E. J. et al, *Synthetic Comm.* 23 1443–1445, 1993.

The natural polyamines, including putrescine, spermidine and spermine, are incorporated into the compositions of this invention by coupling them to various "head" and "linker" groups. Other naturally occurring polyamines that can be employed similarly include: $N^1$-acetylspermine, $N^1$-acetylspermidine, $N^8$-acetylspermidine, $N^1$-guanidinospermine, cadaverine, aminopropylcadaverine, homospermidine, caldine (norspermidine), 7-hydroxyspermidine, thermine (norspermine), thermospermine, canavalmine, aminopropylhomospermidine, N,N'-bis(3-aminopropyl) cadaverine, aminopentylnorspermidine, $N^4$-aminopropylnorspermidine, $N^4$-aminopropylspermidine, caldopentamine, homocaldopentamine, $N^4$-bis(aminopropyl)norspermidine, thermopentamine, $N^4$-bis(aminopropyl)spermidine, caldohexamine, homothermohexamine and homocaldohexamine.

The metabolic stability in vivo of monosubstituted polyamine analogues is increased by modifying these compounds to resist enzymatic degradation. For example, substitution of the terminal primary amine group with an alkyl group would achieve this by preventing oxidative metabolism. This invention also includes compounds with alkylated secondary amino groups. N-alkylation of the amide nitrogens slows down proteolytic degradation.

Figure 11:
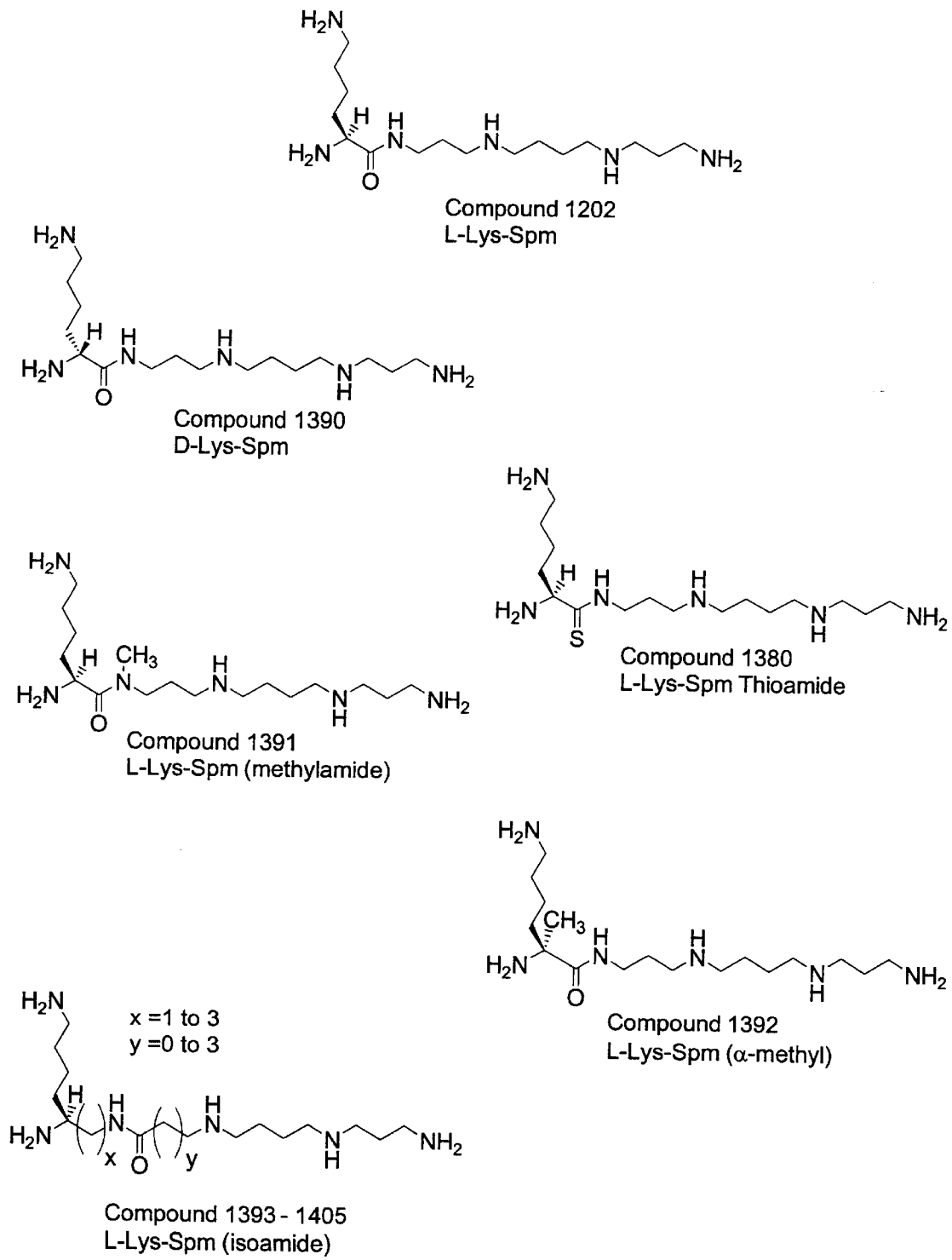
FIG. 11 shows compound 1202 L-Lys-spermine and variations of that compound, which may be used in preparing bispolyamines of the invention.

An additional method to prevent metabolic degradation of amide bonds is to produce the thioamide derivative. FIG. 11*a* shows these changes implemented into compound 1202 L-Lys-spermine conjugates before its use in the bispolyamines of the invention. Combinations of these changes are also encompassed as part of the present invention.

The foregoing changes can be achieved by a number of synthetic routes. Substitution of carbon atoms α to secondary nitrogens and acylation of nitrogens can also slow degradation by polyamine oxidase. Such chemical modifications may minimize potential pharmacological side effects of these compounds.

Alternatively, methyl groups can be introduced α to the terminal amino groups of spermine (Lakanen, J. R. et al, *J. Med. Chem.* 35:724–734, 1992). The 1,12-dimethylspermine analogue 121 was very resistant to normal metabolic degradation. This compound is easily coupled as part of a bispolyamine.

Polyamine analogues of 4 with acetyl (47), N-ethyl (35) and α-dimethyl (66) substitution have been synthesized and shown to have $K_i$'s (for the MDA-MB-231 cell PATr) of 2100, 41, 18 nM, respectively.

Detectably labeled polyamine derivatives can be synthesized using radiolabeled $^{14}C$-spermine or other radiolabeled polyamine as starting material.

Various polyamine analogues alkylated at internal carbons can also be synthesized. 5-carboxyspermine, tetra tBoc-5-carboxyspermine and its acid chloride are synthesized according Huber, H. et al., *J. Biol. Chem.* 271:27556–27563, 1994. The resulting acid chloride can then be reacted with various nucleophilic reagents to produce carboxy-substituted polyamine analogues following removal of the tBoc group. These analogues can then be coupled to the reagents that donate the linker and/or head group. Alternatively, the carboxy intermediate can be reduced to an intermediate that is used to synthesize numerous analogues. Such analogues are of interest in the present invention as alkylating agents (e.g., internal aziridine spermine derivatives) or as enzyme-activated irreversible inhibitors of enzymes involved in polyamine biosynthesis, utilization and degradation (e.g., spermine synthase, deoxyhypusine synthase, polyamine oxidase). Any enzyme that acts on the substituted carbon atom will generate a highly reactive intermediate that can alkylate the enzyme's active site residues.

Many polyamine derivatives are available commercially, and these can easily be derivatized further to make the polyamine analogues of the present invention.

Preferred Bispolyamines

Preferred bispolyamine compounds include those produced by linking polyamine analogs as presented in FIGS. 2 and 9*a* to 9*j* as well as derivatives thereof with pharmaceutical utility as an anti-cancer, anti-viral, anti-microbial, or anti-fungal chemotherapeutic. Particularly preferred compounds include those presented in FIGS. 16 and 17 as well as derivatives thereof.

The further derivatization or optimization of bispolyamine compounds having a desirable activity may be achieved by structural and functional comparisons with other bispolyamine analogues and derivatives of the invention to incorporate particular structural elements of other analogues into the compound being optimized. The structural elements will be selected based on the expectation of improving functionalities such as, but not limited to, inhibitory activity, metabolic stability, specificity, handling and administration, binding affinity, non-incorporation into cellular polyamine pools, and decreases in side effects.

The resultant compounds modified by the introduction of such structural elements may be of any structure, including those within the limits of the bispolyamine analogues and derivative structures defined herein. Stated differently, the resultant compounds may have one or more additional atoms or functional groups and/or removal of one or more atoms or functional groups after optimization, resulting in a compound either within or beyond the limits of the bispolyamine analogues and derivative structures defined herein.

Multiple iterations of optimizing compounds with preferred activity may be conducted to further improve the bispolyamine analogue.

The design of some bispolyamine analogues and derivatives of the invention was driven by several requirements of any compound that would act in concert with an ODC inhibitor in a combination therapy to deplete cellular polyamines through both the biosynthetic and transport pathways. Such compounds need to be good inhibitors extracellular uptake of polyamines (putrescine, spermidine, and spermine) while not being themselves substrates for the transporter or for maintenance of cellular polyamine levels. If such were substrates of the transporter and could function as the natural polyamines (or be metabolized to polyamines), the compounds would defeat their purpose of depleting cellular polyamine levels.

In addition to the use of amino acid groups, the bispolyamine analogues and derivatives of the invention may comprise a polyamine with a head group linked to a polyamine where coupler such as —C(=O)NH—, —S(=O)$_2$NH—, —NHC(=O)—, —HNS(=O)$_2$—, —HNC(=O)NH—, —HNC(=S)NH—, O—C(=O)NH—, —O—, —S—, —CH$_2$— or —NH— is used to combine the "head" group and the linker moiety.

Head Groups

1. General Description

As stated above, bispolyamines of the invention are composed of polyamine derivatives that are linked together via terminal amino groups. One example of polyamine derivatives that may be made part of a bispolyamine are polyamine lead compounds derivatized with a head group.

The general construction of the lead compounds shown below indicates the connections between the head group, linker and polyamine:

where coupler$_1$ is —C(=O)NH—, —S(=O)$_2$NH—, —NHC(=O)—, —HNS(=O)$_2$—, —HNC(=O)NH—, —HNC(=S)NH—, O—C(=O)NH—, —O—, —S—, —CH$_2$— or —NH—; and coupler$_2$ is —C(=O)NH—, —S(=O)$_2$NH—, —HNC(=O)NH—, —HNC(=S)NH— or —NH—. A number of coupling chemistries can be used to combine the "head" group and the linker moiety. Types of "head" groups are disclosed below as are additional groups that can be substituted onto these head groups.

The coupling between the polyamine and linker will be described below before description of the linkers. What follows is the definition of the head groups.

The structural diversity of preferred head groups is very large, and most organic groups that can be covalently attached to an amine are potential candidates.

The following table provides guidance regarding the intended head groups but is by no means is intended to be limiting. Additional examples of head groups suitable for use in the polyamine analogues of the invention include those in column "R2" of Table 1 in Dhainaut et al. (1996) "New purines and purine analogs as modulators of multi-drug resistance." J. Med. Chem. 39:4099–4108, which is incorporated herein in its entirety as if fully set forth. Mono and multi-substitutions on the ring structures of the head groups are also intended.

| LIST OF HEAD GROUP SUBSTITUENTS | | | |
|---|---|---|---|
| halogen | cyclohexyl | ethoxyl | propyl ester |
| methyl | cycloheptyl | propoxyl | isopropyl ester |
| ethyl | cyclooctyl | thio | cyano |
| propyl | cyclononyl | methyl thio | isocyanato |
| isopropyl | cyclodecyl | ethylthio | trifluoromethyl |
| butyl | hexyl | propylthio | trichloromethyl |
| isobutyl | 2-hexyl | butylthio | tribromomethyl |
| tert-butyl | 3-hexyl | isopropylthio | azido |
| pentyl | allyl | nitro | Acetoxy |
| 2-pentyl | vinyl | amino | Carboxamide |
| 3-pentyl | acetylenic | acetamide | N-methylcarboxamide |
| neopentyl | propargylic | formamide | N,N-dimethylcarbox- |
| cyclopentyl | homopropargylic | carboxylic | amide |
| cyclopropyl | hydroxyl | methyl ester | N-ethylcarboxamide |
| cyclobutyl | methoxyl | ethyl ester | N,N-diethylcarboxamide |

2. Aromatic Groups

Aromatic groups include phenyl naphthyl, 1-, 2-, or 3-biphenyl, indenyl, acenaphthylenyl, anthracenyl, phenanthrenyl, phenalenyl, triphenylenyl pyrenyl, diphenylmethylenyl, etc.

3. Heterocyclic Groups

Heterocyclic groups include pyrrolidinyl, piperidinyl, piperazinyl, morpholinyl, biphenyl, furanyl, pyrrolyl, 1,2-diazolyl, imidazolyl, 1H,1,2,3-triazolyl, 1H-1,2,3,4-tetrazolyl, thiazolyl, oxazolyl, 1,3,4-thiadiazolyl, pyridinyl, pyrimidyl, 1,2-diazinyl, 1,4-diazinyl, 1,3,5-trizinyl, dibenzofuranyl, acridinyl, 2,1,3-benzothiadiazole, isoquinolinyl, quinolinyl, benzofuranyl, isobenzofuranyl, 1,3-benzodiazinyl, phenazinyl, phenoxazinyl, phenothiazinyl, pyran, chromenyl, xanthenyl, indolizinyl, isoindolyl, indolyl, purinyl, phthalazinyl, naphthyridinyl, quinoxalinyl, quinazolinyl, cinnolinyl, ptericinyl, carbazolyl, β-carbolinyl, phenanthridinyl, acridinyl, perimidinyl, phenanthrolinyl, isothiazoly, furazanyl, indolinyl, isoindolinyl, quinuclidinyl, and biotinyl.

4. Aliphatic Groups

This class includes straight-chain, branched and cyclic hydrocarbons attached to the linker. The group includes $C_{2-10}$ alkanes; $C_{3-10}$ alkenes containing 1 to 3 unsaturations; $C_{3-10}$ alkynes containing 1 to 3 unsaturations; branched $C_{3-10}$ alkanes, alkenes and alkynes; polycyclic aliphatic hydrocarbons and steroid-like ring systems that include $C_{3-8}$ cycloalkyl, adamantyl, camphoryl, cholesteryl, etc.

5. Miscellaneous a. DNA Intercalators:

Coupling an intercalator to the polyamine will yield an agent with much higher affinity for nucleic acid targets. Examples of intercalating agents amenable to this use are acridine, 9-aminoacridine, proflavine, actinomycin D, daunorubicin, doxorubicin, nogalamycin, menogaril, ellipticine, BD-40, amsacrine, acodazole, 2-pheylquinoline carboxamide, crisnatol, nitracrine, pyrazoloacridine, mitonoafide, ametantrone, mitoxantrone, oxanthrazole, bisantrene, echinomycin. For a review of DNA intercalating agents see Baguley, B. C., *Anti-Cancer Drug Design* 1991, 6, 1–35.

b. Biochemical Conjugates

Drug selectivity is achieved by targeting specific cells or enzymes/receptors on cells. The following biochemicals are candidates for coupling to polyamines for producing a selective pharmaceutical agent: steroids, prostaglandins, phospholipids; enzyme cofactors including nucleotide containing molecules such as NADH, AcetylCoA, AdoMet, flavin, tryptophantryptophyl quinone (TTQ), etc.

An additional series of head groups comprises polyamines conjugated to polyethylene glycol (PEG) or O-methylated PEG (abbreviated MeOPEG) polymers of various sizes.

6. Multiple Ring Head Groups

Figure 15:
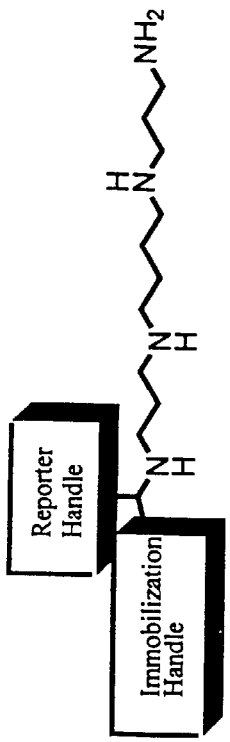
FIG. 15, panels A and B, is a schematic illustration showing the possible sites for modifying a polyamine to create an "immobilization handle" and a "reporter handle" combination. These modified polyamines may be used in the present invention to produce bis-polyamines.
Figure 15:
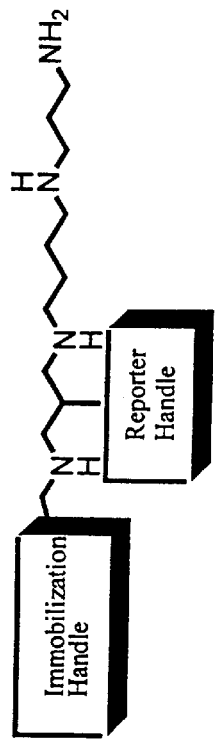
Figure 15:
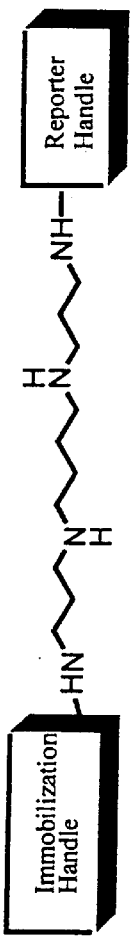

Head groups can vary from simple alkyl substitutions to multi-ring and multi-single-ring substitutions. Some of the structural variations are schematically represented in FIG. 15 of U.S. patent application Ser. No. 09/341,400.

Linker Group

1. General Description

The linker portion of polyamine analogues for use in bispolyamine compounds can be represented by a general structure with an amino group at one end and an acid group on the other. One group of linkers contains diamino groups that are bonded via a urea linkage to the polyamine and via an amide, urea or sulfonamide linkage to the head group. The head group can also be bonded through other couplings such as ether, thioether and C—C bonds. The schematic structure shown above (in the section labeled "Head Groups, 1. General Description) shows the function of the linker moiety connecting the head group to the polyamine and possessing a desired length and combination of steric, conformational and hydrophobic properties. Also shown are the possible combination of coupling methods. Each coupling method can be used in combination with any of the three methods in FIG. 3 of U.S. patent application Ser. No. 09/341,400 at the other position to result in a wide array of desired properties.

The linker group can have a range of properties that are reflected by the number of variations discussed below. Changes in the linker structure will be affect the properties of the whole polyamine analogue such as hydrophobicity, hydrophilicity, distance between head and polyamine portions, steric arrangement of head and polyamine portions, conformational properties, solubility and electronic properties.

2. Aliphatic Straight Chain Linkers

A series of linkers was been synthesized to test the effect of different distances between head group and polyamine. This series is most simply represented by the straight-chain aliphatic linkers having various carbon chain lengths shown below as compound 148).

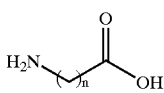

n = 1 to 12

The present inventors discovered that linker length had dramatic effects on the PAT inhibitory activity and the cell growth inhibitory activity. A low $K_i$ is optimal for $C_6$ linkers in the presence of an aromatic head group. However, in the absence of a head group, differences in growth or transport inhibitory, activities have not been dramatic. Thus, "headless" compounds have $K_i$s in the order of about 25 nM but have more attenuated inhibitory effects cell growth (breast cancer cell line) most likely due to their ability to actually be transported. A prostate cancer cell line is more powerfully inhibited by these "headless" inhibitors. The C3-headless compound had dramatic effects on cell growth.

The synthetic route to this series of compounds, starting with various polyamines and head groups, is represented by the DACS 4 synthetic scheme depicted in FIG. 9 of U.S. patent application Ser. No. 09/341,400. The amino group is protected by the N-'Boc group, and the carboxylic acid is then activated by forming the p-nitrophenyl ester. After acid deprotection of the N-'Boc group, the amino group can be reacted with an acid or sulfonamide chloride of the desired head group. After purification, direct reaction with the polyamine of choice in methanol gives the desired product. This can be purified by either (1) reverse-phase silica gel chromatography using 2:9 MeOH/0.5 N HCl or (2) cation-exchange chromatography over BioRex 70 resin ($NH_4$ form) using a linear gradient of from 0 to 2N $NH_4OH$.

3. Unsaturated Straight-chain Aliphatic Linkers

Varying degrees of unsaturation (alkene and alkyne) together with the geometric isomers of the alkene derivatives can be introduced into the linker moiety as depicted below (149 and 156) These variations allow introduction of conformational restraint into the final product.

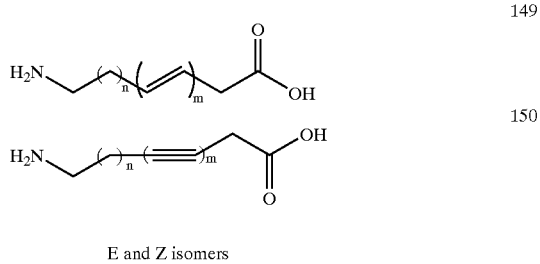

E and Z isomers where n=0 to 7 and m=1 to 4

4. Carbon-substituted and Cyclic Aliphatic Linkers

Branched chain and cyclic saturated aliphatic linker groups impose conformational restraint on the desired polyamine analogue. Compounds 151 and 152 below illustrates this class of structure.

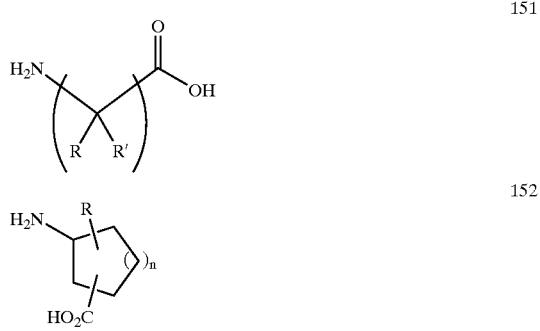

where n=1–10; R and R' vary independently and can be H or $CH_3(CH_2)_m$, and where m=1 to 10.

5. Chiral Carbon-substituted Amino Acid Linkers

Figure 12:
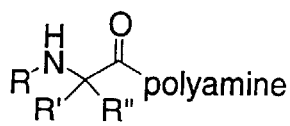
FIG. 12 lists amino acid-polyamine conjugates where the amino acid moiety may vary in chirality. These amino acids may also be used to form bispolyamines of the invention.
Figure 13:
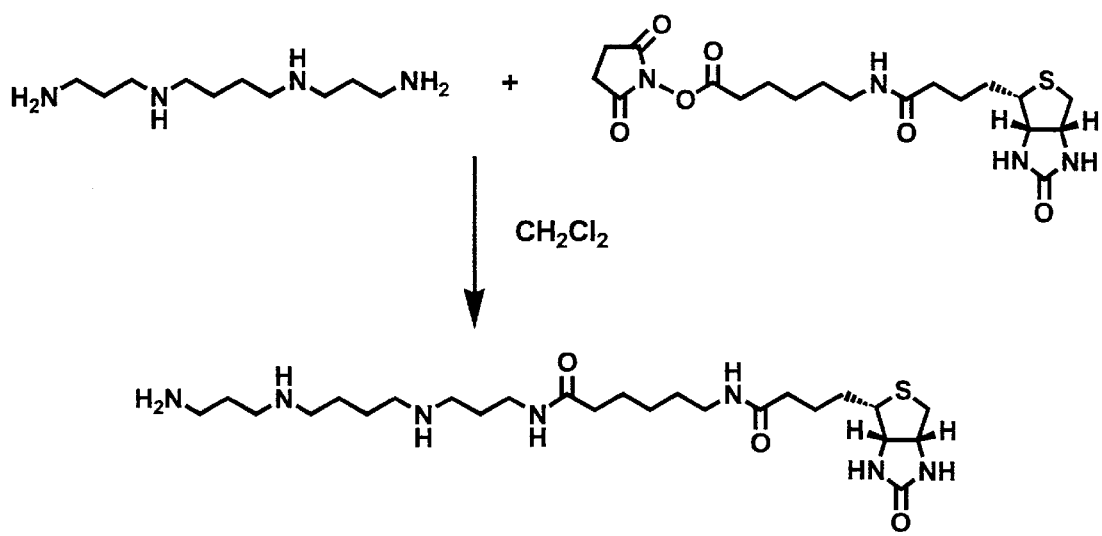
FIGS. 13 and 14 show the synthesis of biotin modified polyamines $N^1$-[($N^6$-(biotinyl)-6-aminocaproyl)]spermine and $N^1$-(biotinyl)spermine, which may be used in preparing the bispolyamines of the invention.
Figure 14:
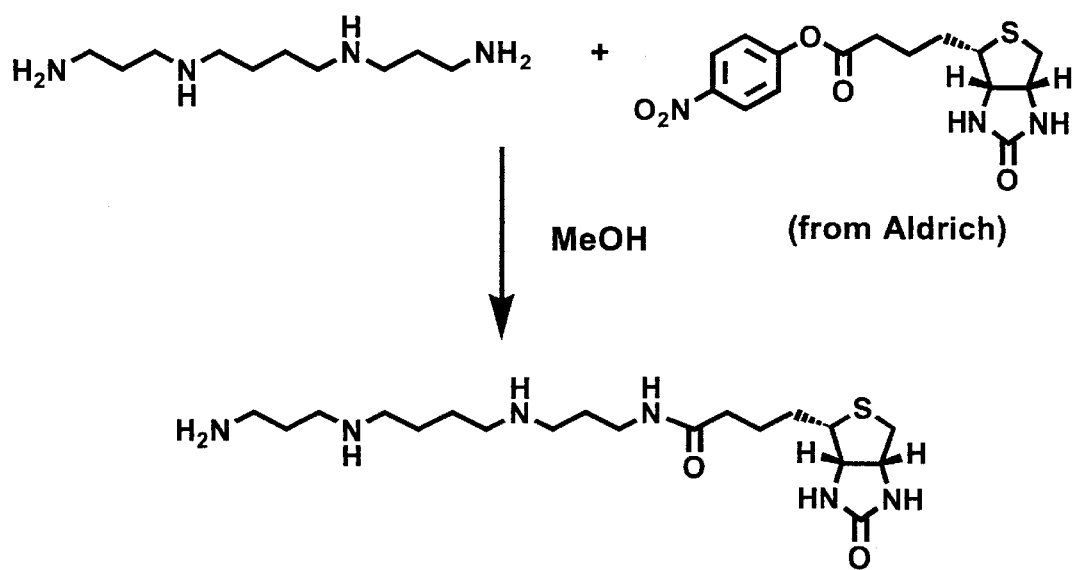

Great structural diversity can be incorporated quickly into the polyamine analogues by using any of the large number of chiral amino acids that are available commercially. Many of the chiral amino acid intermediates are also available commercially, including some N-'Boc protected amino acids and some N-'Boc protected amino acid p-nitrophenyl esters. FIG. 12 (153) illustrates a variety of derivatives that have been produced by this method. These amino acid-polyamine conjugates contain variable chirality in the amino acid moiety. The amino acids can also be used as "linkers" to other N-substituted "head groups".

Figure 8:
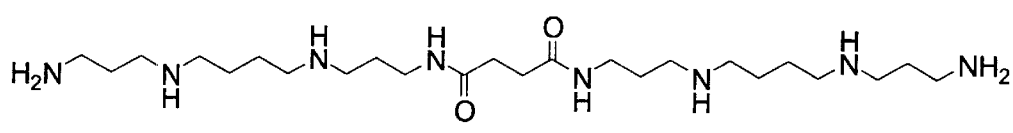
FIG. 8 shows preferred linked bis-amide dimers of spermine.
Figure 8:
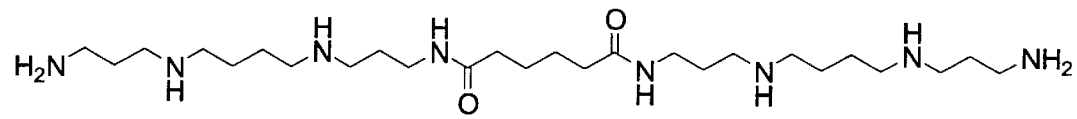
Figure 8:
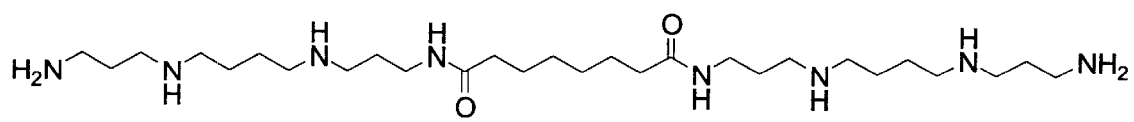
Figure 9A:
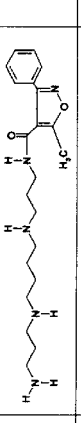
Figure 9A:
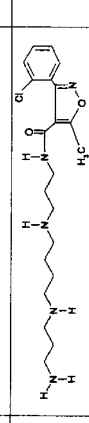
Figure 9A:
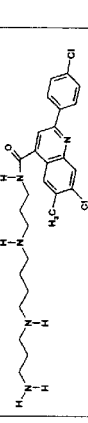
Figure 9A:
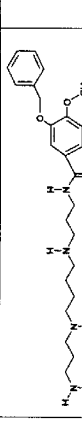
Figure 9A:
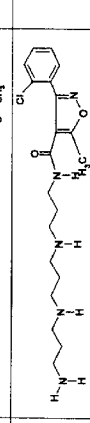
Figure 9A:
Figure 9A:
Figure 9A:
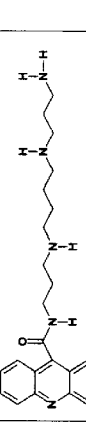

An additional thousand α-amino acid analogues known in the art can be used to form polyamine adducts. These are very easily incorporated into the present invention through synthetic sequences described in FIGS. 8 and 9 of U.S. patent application Ser. No. 09/341,400. Several key examples are; t-butylglycine, ornithine, α-aminoisobutyric acid, 2-aminobutyric acid, α-aminosuberic acid, 4-chlorophenylalanine, citrulline, β-cyclohexylalanine, 3,4-dehydroproline, 3,5-diiodotyrosine, homocitrulline, homoserine, hydroxyproline, β-hydroxvaline, 4-nitrophenylalanine, norleucine, norvaline, phenylglycine, pyroglutamine, β-(2-thienyl)alanine, etc. Several important β-amino acids are easily incorporated into the present invention through the chemistry discussed above. A key example is β-alanine, etc.

Both stereoisomers of the natural L-amino acids (L=S) or D-amino acids (D=R) can be used in this invention. Because each isomer can be used individually, the structural diversity of the analogues is markedly enhanced.

6. "Headless" Linkers

The desired biological properties do not always depend upon the presence of a head group. Hence, a large series of so-called "headless" derivatives, containing a polyamine and linker without a head group were synthesized and tested. These derivatives are made by reacting the active ester (p-nitrophenyl or N-hydroxylsuccinimide) of the N-$^t$Boc amino acid with the polyamine of interest. The resulting N-$^t$Boc protected derivatives are then purified by cation-exchange chromatography over BioRex 70 ($NH_4$ form) resin using a linear gradient from 0 to 2N $NH_4OH$. The $^t$Boc group can then be cleaved by acid treatment. Both the tBoc and acid deprotected derivatives can be tested for biological activity. The full series of amino acids discussed above, together with other derivatives have been synthesized.

Reactive, Irreversible Polyamine Transport Inhibitors

A. Alkylating Reagents

1. Aziridines

Polyamines substituted with fluorophores and other bulky end group were found to have the intrinsic property of high avidity binding to the PATr. This suggested that, in addition to utility as a diagnostic or research tool, they are useful as therapeutic agents for treating diseases or conditions wherein it is desirable to inhibit PAT. Their intrinsic affinity for other polyamine targets such as DNA broadens even further the scope of their therapeutic utility. Correspondingly, bispolyamines containing such modified polyamines are expected to display the same activities.

In a preferred embodiment the polyamine core is substituted with the aziridinyl group. Aziridinyl-substituted polyamines react with nucleophilic groups in target binding complexes (receptors, transporters, enzymes and nucleic acids). In addition they can be exploited to bind other reactive moieties to polyamines. These mono- and di-substituted polyamine analogues are useful as drugs because of their inhibition of (a) the PATr, (b) polyamine synthesis and (c) reactions that use nucleic acids as substrates.

In another embodiment, a reactive group other than aziridine is introduced into a polyamine already substituted with a head group and a linker. This reactive group allows the labeled polyamine to bind covalently to an appropriate nucleophilic site on a polyamine-binding target molecule such as the PATr. Compounds of this type are used to covalently label receptors, enzymes or nucleic acids; thus, the modified polyamine serves as an affinity label that is useful in diagnostic assays and as a tool to isolate a polyamine binding target. Again, such compounds used as drugs will treat diseases or conditions which are ameliorated by blocking PAT or DNA-polyamine interactions. By virtue of the relative irreversibility of their binding, such compounds can be used at lower doses or at decreased frequency compared to compounds known in the art.

Disubstituted polyamines are synthesized by using the appropriate amine protecting groups on the polyamines. Reagents for the stepwise fuctionalization of spermine are known (Bergeron, R. J. et al., *J. Org. Chem.* 53: 3108–3111 (1988); Byk, G. et al., *Tetrahedron Lett.* 38: 3219–3222 (1997)). Bergeron et al (supra) described the use of four independent amine-protecting groups: benzyl, t-butoxycarbonyl, trifluoroacetyl, and 2,2,2-trichloro-t-butoxycarbonyl. Conditions that allow the selective removal of each protecting group were also described. These reaction conditions allow independent and selective derivatization of each nitrogen of spermine. Thus this invention includes derivatization of monofunctionalized spermine with a linker/head group on any one of the four nitrogens and the synthesis of polyamine analogues with more than one functionalized nitrogen.

Methods to introduce an aziridine group into spermine (Li et al, *J. Med. Chem.*, 39:339–341 (1996) and into derivatives of spermidine (Yuan et al, *Proc. Am. Assoc. Cancer Res.*, 34: 380 (1993) are available.

2. Other Reactive Groups

Other useful moieties that can be added instead of the aziridine group and that react with nucleophiles to form covalent bonds include chloro-, bromo- and iodoacetamides, sulfonylfluorides, esters, nitrogen mustards, etc The chemically reactive 2-haloacetamide group can easily be introduced into any of the polyamine analogues by reaction with the appropriate 2-haloacetic acid halide. Other chemically reactive groups are described below.

B. Photochemically Activated Reagents

The use of photochemically activated functionalities on biologically active molecules is a well known (Fleming, S. A., *Tetrahedron* 51:12479–12520, 1995). In the polyamine field, Felschow et al. attached an azidobenzoic acid moiety to spermine and examined the interaction of the resulting adduct with cell surface proteins (Felschow, D M et al. *Biochem. J.* 328, 889–895, 1997; Felschow, D M et al., *J. Biol. Chem.* 270:28705–28711, 1995). Since their photo-probe had an apparent $K_i$ of 1 μM versus spermidine for the PATr, the photolabeled proteins described were a mixture of polyamine binding proteins. One of the most potent PAT inhibitors of the present invention, DACS, has a $K_i$ of <10 nM, which indicates an affinity 100 times higher than the compound reported by Felschow et al. Therefore introduction of a photoactivatable group to this molecule holds great promise in the isolation of the PATr protein(s).

1. Azide

Substitution of the dimethylamino group in dansyl chloride by azide produces a photochemically reactive chemical group. The preparation of 1-azido-5-naphthalene sulfonyl chloride has been described (Muramoto, K., *Agric. Biol. Chem.* 1984, 48 (11), 2695–2699), and it is also available commercially from Molecular Probes Inc. (Eugene, Oreg.). Introduction of this compound into the synthetic scheme for DACS is straightforward and merely requires substitution for dansyl chloride.

This azido derivative, would enable isolation and characterization of the PATr protein(s), and would also find use as an irreversible, photoactivatable drug molecule.

2. Diaziridines

Substitution of a diaziridine group on the head group would accomplish many of the same goals as noted above.

3. Diazo Groups

Polyamine analogues with photoactivatible head groups are made using p-nitrophenyl 3-diazopyruvate, a reagent for introduction of a photoactivatable 3-diazopyruvate group to an aliphatic amine. This agent is also available from Molecular Probes, Inc. The desired derivative is made by reacting this reagent with the free amino, p-nitrophenyl activated linker precursor, purifying the linker/head group intermediate, and reacting it with the polyamine.

Analytical and Diagnostic Uses

The bispolyamine analogues and derivatives of the invention may also be used as reporter molecules and probes to assay other pharmacological targets, including soluble proteins, as described in PCT/US98/14896, which also describes the use of reporter head groups and polyamine transport assays.

TESTING INHIBITORS OF POLYAMINE TRANSPORT

Through screening bispolyamine compounds made by the various synthetic routes described above, several compounds were found to effectively inhibit polyamine transport. "R" values were calculated as the ratio of the $IC_{50}$ in the absence of DFMO, or other polyamine synthesis inhibitor, over the $IC_{50}$ in the presence of DFMO, or other polyamine synthesis inhibitor. An "R" value of 1 reflects a polyamine transport inhibitor that shows no change in the presence of a polyamine synthesis inhibitor, suggesting that the transport inhibitor fails to inhibit the transporter or is not specific for the transporter.

As expected, the presence of a polyamine synthesis inhibitor enhances the inhibition of cell growth by the bispolyamine transport inhibitors of the invention when used alone. A large enhancement reflects a good transport inhibitor that is specific for the polyamine transporter because it suggests that the transport inhibitor does not interact significantly with other cellular components. Preferred transport inhibitors of the invention will have "R" values of about 2, but more preferably above about each of the following: 5, 10, 50, 100, 200, 300, and 400. Most preferred are compounds with "R" values of above about 500, above about 1000, or above about 10,000. Since significant "R" values may reflect conditions where neither the transport inhibitor nor the polyamine synthesis inhibitor alone are able to result in growth inhibition, the combination of the two may be considered to result in a synergistic effect, which varies according to the specificity of the transport inhibitor in combination with the specific synthesis inhibitor used. Such effects are not readily predictable in advance because the magnitude of inhibitory activity and degree of specificity are individual to each transport inhibitor.

The "R" values of the invention may also be considered in relation to the $IC_{50}$ values of this invention's polyamine transport inhibitors in the presence or absence of a polyamine synthesis inhibitor. Such a consideration provides useful information regarding the potential usefulness of the transport inhibitor as an active ingredient. Preferred is a review of the "R" value versus the $IC_{50}$ value in the presence of a polyamine synthesis inhibitor. This is useful because if that $IC_{50}$ value is too high, the transport inhibitor is unlikely to be a viable active agent because of the necessary high concentrations needed for inhibitory activity. This requirement for a high concentration would not necessarily be negated even by very high "R" values. Thus inhibitors of the invention are preferably those that exhibit a $IC_{50}$ value of about 100 $\mu$M or less when used in combination with a polyamine synthesis inhibitor. More preferable are inhibitors that exhibit $IC_{50}$ values, in the presence of a polyamine synthesis inhibitor, of less than about each of the following: 75, 50, and 25 $\mu$M. Most preferred are compounds that exhibit $IC_{50}$ values, in the presence of a polyamine synthesis inhibitor, of less than about 10, less than about 5, less than about 1, less than about 0.5, less than about 0.1, less than about 0.05, and less than about 0.01 $\mu$M.

Using both a kinetic measure and a biological assay, the present inventors observed high correlation between the inhibition of PAT and growth.

PHARMACEUTICAL AND THERAPEUTIC COMPOSITIONS

The bispolyamine analogues and derivatives of the invention, as well as the pharmaceutically acceptable salts thereof, may be formulated into pharmaceutical compositions. Pharmaceutically acceptable acid addition salts of the compounds of the invention which contain basic groups are formed where appropriate with strong or moderately strong, non-toxic, organic or inorganic acids in the presence of the basic amine by methods known in the art. Exemplary of the acid addition salts that are included in this invention are maleate, fumarate, lactate, oxalate, methanesulfonate, ethanesulfonate, benzenesulfonate, tartrate, citrate, hydrochloride, hydrobromide, sulfate, phosphate and nitrate salts.

As stated above, the compounds of the invention possess the ability to inhibit PAT or polyamine synthesis, properties that are exploited in the treatment of any of a number of diseases or conditions, most notably cancer. A composition of this invention may be active per se, or may act as a "pro-drug" that is converted in vivo to active form.

The compounds of the invention, as well as the pharmaceutically acceptable salts thereof, may be incorporated into convenient dosage forms, such as capsules, impregnated wafers, tablets or injectable preparations. Solid or liquid pharmaceutically acceptable carriers may be employed. Pharmaceutical compositions designed for timed or delayed release may also be formulated.

Preferably, the compounds of the invention are administered systemically, e.g., by injection. When used, injection may be by any known route, preferably intravenous, subcutaneous, intramuscular, intracranial or intraperitoneal. Injectables can be prepared in conventional forms, either as solutions or suspensions, solid forms suitable for solution or suspension in liquid prior to injection, or as emulsions.

Solid carriers include starch, lactose, calcium sulfate dihydrate, terra alba, sucrose, talc, gelatin, agar, pectin, acacia, magnesium stearate and stearic acid. Liquid carriers include syrup, peanut oil, olive oil, saline, water, dextrose, glycerol and the like. Similarly, the carrier or diluent may include any prolonged release material, such as glyceryl monostearate or glyceryl distearate, alone or with a wax. When a liquid carrier is used, the preparation may be in the form of a syrup, elixir, emulsion, soft gelatin capsule, liquid containing capsule, sterile injectable liquid (e.g., a solution), such as an ampoule, or an aqueous or nonaqueous liquid suspension. A summary of such pharmaceutical compositions may be found, for example, in *Remington's Pharmaceutical Sciences*, Mack Publishing Company, Easton Pa. (Gennaro 18th ed. 1990).

The pharmaceutical preparations are made following conventional techniques of pharmaceutical chemistry involving such steps as mixing, granulating and compressing, when necessary for tablet forms, or mixing, filling and dissolving the ingredients, as appropriate, to give the desired products for oral or parenteral, including , topical, transdermal, intravaginal, intranasal, intrabronchial, intracranial, intraocular, intraaural and rectal administration. The pharmaceutical compositions may also contain minor amounts of nontoxic auxiliary substances such as wetting or emulsifying agents, pH buffering agents and so forth.

Although the preferred routes of administration are systemic, the pharmaceutical composition may be administered topically or transdermally, e.g., as an ointment, cream or gel; orally; rectally; e.g, as a suppository, parenterally, by injection or continuously by infusion; intravaginally; intranasally; intrabronchially; intracranially intra-aurally; or intraocularly.

For topical application, the compound may be incorporated into topically applied vehicles such as a salve or ointment. The carrier for the active ingredient may be either in sprayable or nonsprayable form. Non-sprayable forms can be semi-solid or solid forms comprising a carrier indigenous to topical application and having a dynamic viscosity preferably greater than that of water. Suitable formulations include, but are not limited to, solution, suspensions, emulsions, creams, ointments, powders, liniments, salves, and the like. If desired, these may be sterilized or mixed with auxiliary agents, e.g., preservatives, stabilizers, wetting agents, buffers, or salts for influencing osmotic pressure and the like. Preferred vehicles for non-sprayable topical preparations include ointment bases, e.g., polyethylene glycol-1000 (PEG-1000); conventional creams such as HEB cream; gels; as well as petroleum jelly and the like.

Also suitable for topical application are sprayable aerosol preparations wherein the compound, preferably in combination with a solid or liquid inert carrier material, is packaged in a squeeze bottle or in admixture with a pressurized volatile, normally gaseous propellant. The aerosol preparations can contain solvents, buffers, surfactants; perfumes, and/or antioxidants in addition to the compounds of the invention.

For the preferred topical applications, especially for humans, it is preferred to administer an effective amount of the compound to a target area, e.g., skin surface, mucous membrane, eyes, etc. This amount will generally range from about 0.001 mg to about 1 g per application, depending upon the area to be treated, the severity of the symptoms, and the nature of the topical vehicle employed.

The compositions of the invention be given in combination with one or more additional compounds that are used to treat the disease or condition. For treating cancer, the polyamine analogues and derivatives are given in combination with anti-tumor agents, such as mitotic inhibitors, e.g., vinblastine; alkylating agents, e.g., cyclophosphamide; folate inhibitors, e.g., methotrexate, pritrexim or trimetrexate; antimetabolites, e.g., 5-fluorouracil and cytosine arabinoside; intercalating antibiotics, e.g, adriamycin and bleomycin; enzymes or enzyme inhibitors, e.g., asparaginase; topoisomerase inhibitors, e.g., etoposide; or biological response modifiers, e.g., interferon. In fact, pharmaceutical compositions comprising any known cancer therapeutic in combination with the polyamine analogues and derivatives disclosed herein are within the scope of this invention. Most preferably, the present compounds are administered in combination with a polyamine synthesis inhibitor such as DFMO.

The pharmaceutical compositions of the invention may also comprise one or more other medicaments such as anti-infectives including antibacterial, anti-fungal, anti-parasitic, anti-viral, and anti-coccidial agents.

Typical single dosages of the compounds of this invention are between about 1 ng and about 10 g/kg body weight. The dose is preferably between about 0.01 mg and about 1 g/kg body wt. and, most preferably, between about 0.1 mg and about 100 mg/kg body wt. For topical administration, dosages in the range of about 0.01–20% concentration of the compound, preferably 1–5%, are suggested. A total daily dosage in the range of about 1–500 mg is preferred for oral administration. The foregoing ranges are, however, suggestive, as the number of variables in regard to an individual treatment regime is large, and considerable excursions from these recommended values are expected and may be routinely made by those skilled in the art.

Effective amounts or doses of the compound for treating a disease or condition can be determined using recognized in vitro systems or in vivo animal models for the particular disease or condition. In the case of cancer, many art-recognized models are known and are representative of a broad spectrum of human tumors. The compounds may be tested for inhibition of tumor cell growth in culture using standard assays with any of a multitude of tumor cell lines of human or nonhuman animal origin. Many of these approaches, including animal models, are described in detail in Geran, R. I. et al., "Protocols for Screening Chemical Agents and Natural Products Against Animal Tumors and Other Biological Systems (Third Edition)", *Canc. Chemother. Reports*, Part 3, 3:1–112.

Synthetic Methods

The synthetic methods necessary to produce the polyamine analogues and derivatives for the preparation of bispolyamines of the invention, including parallel library synthesis and combinatorial approaches, have been described in PCT/US98/14896.

Additionally, this invention provides synthetic methods whereby bispolyamines may be readily produced (see FIGS. 3A and 3B as well as examples below). Briefly, the method uses 'Boc protected polyamine derivatives as starting substrates that are linked to form bispolyanines. These bispolyamine products are then purified by ion exchange chromatography. Elution of the products permits recovery and availability for optional subsequent deprotection.

Having now generally described the invention, the same will be more readily understood through reference to the following examples which are provided by way of illustration, and are not intended to be limiting of the present invention, unless specified.

EXAMPLE I

Screening of Polyamine Analogues in Transport and Growth Assays

The effect of a number of potential PAT transport inhibitors on PAT and growth of MDA cells is summarized in FIG. 2 (3–98) The ratio "R" is the $IC_{50}$ for polyamine alone relative to the $IC_{50}$ for the polyamine analogue combined with an ODC inhibitor. This value of "R", indicates the relative level of "synergism" between the polyamine analogue and ODC inhibitor. Under the growth assay conditions, the ODC inhibitor alone shows no inhibition.

EXAMPLE II

Ki Determinations and Structure Activity Relationships

The bispolyamine analogues and derivatives of the invention may be evaluated for their ability to inhibit the uptake of spermidine into MDA cells in culture. Joro spider toxin JSTx-3 is available from Calbiochem;

1-Naphthylacetylspermine is available from RBI. Deoxyspergualin was a generous gift from Paul Gladstone. $K_i$s were measured for the bispolyamine analogues in FIG. 16 and the results are shown therein.

EXAMPLE III

$IC_{50}$ Against MDA Cells With DFMO and Spermidine

A cellular assay was developed to highlight the ability of the amino acid/spermine amides to work in concert with the ODC inhibitor DFMO in the presence of added 1 μM spermidine. In this assay, no growth inhibition is observed with DFMO alone because the cells are able to utilize the spermidine added to the culture media even when polyamine biosynthesis is inhibited. Thus inhibition of uptake of the exogenously added spermidine by any of the tested analogues or derivatives results in observable growth inhibition due to polyamine depletion.

Figure 16C:
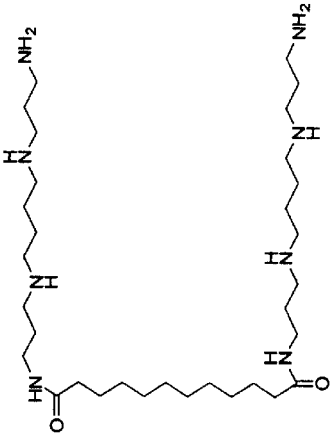
FIG. 16 is a table of preferred deprotected bispolyamines of the invention.
Figure 17A:
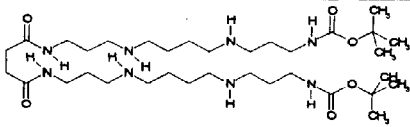
FIG. 17 is a table of preferred protected bispolyamines of the invention.
Figure 17A:
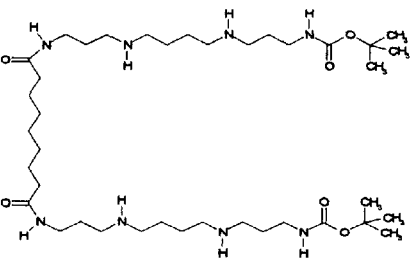
Figure 17A:
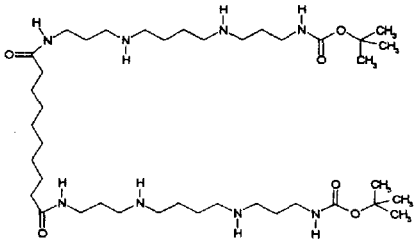
Figure 17A:
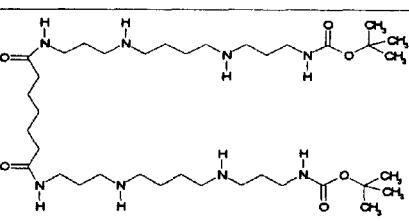
Figure 17A:
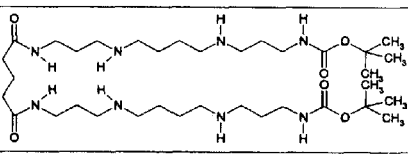
Figure 17A:
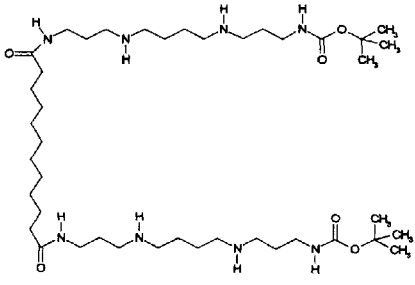
Figure 17A:
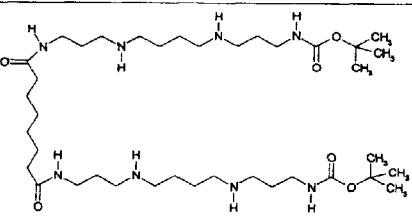

Results with some deprotected bispolyamines are shown in FIG. 16.

EXAMPLE IV

Synthesis of Bispolyamines

The substrates for synthesizing bispolyamines may be prepared by a two part process: synthesis of a linker moiety and synthesis of monoprotected polyamines.

Figure 4:
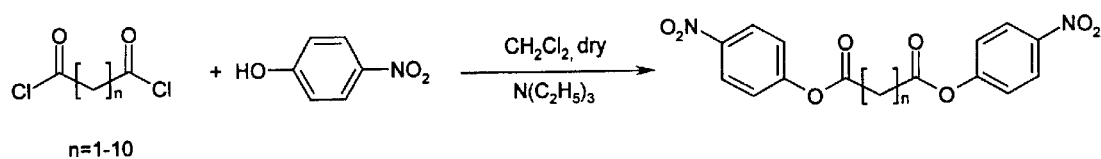
FIG. 4 shows representative synthetic routes for the preparation of p-nitrophenyl activated esters by conversion from the corresponding acid chlorides.
Figure 18:
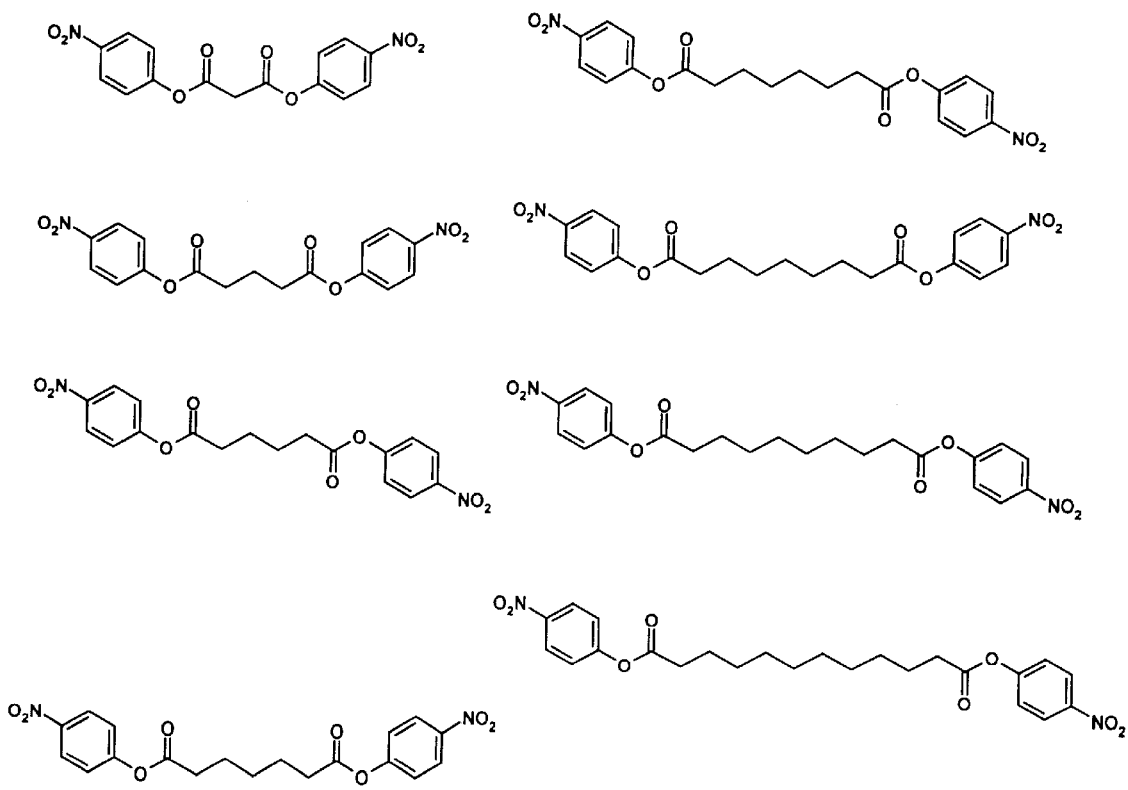
FIG. 18 shows some activated esters suitable for preparation of bispolyamines.

Exemplary linkers are prepared by converting the corresponding acid chlorides to p-nitrophenyl activated esters using 4-nitrophenol. See FIG. 4. Examples of such activated esters are shown in FIG. 18. These are purified by recrystallization in $EtOH/CH_2Cl_2$ (10–30% EtOH) and dried under high vacuum.

Figure 5:
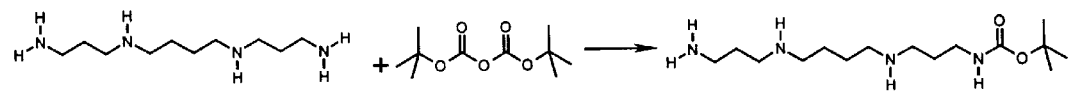
FIG. 5 shows a representative reaction for the protection of a terminal amine group in spermine by treatment with di-tert-butyldicarbonate.
Figure 6:
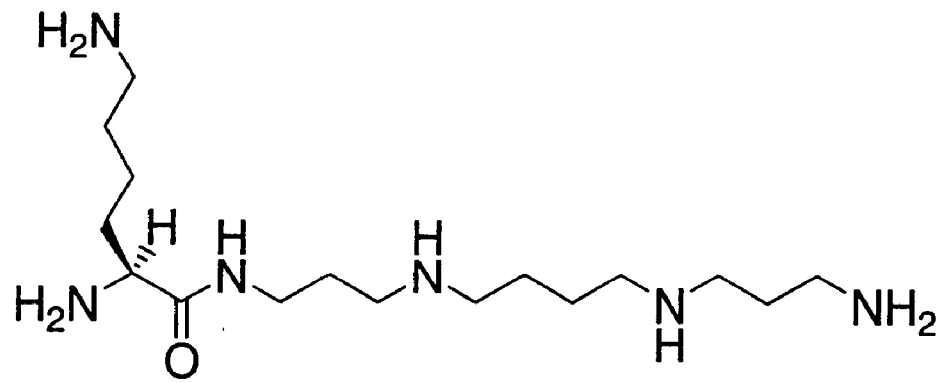
FIG. 6 shows preferred polyamine analogs of the invention that may be linked to form a bispolyamine.
Figure 6:
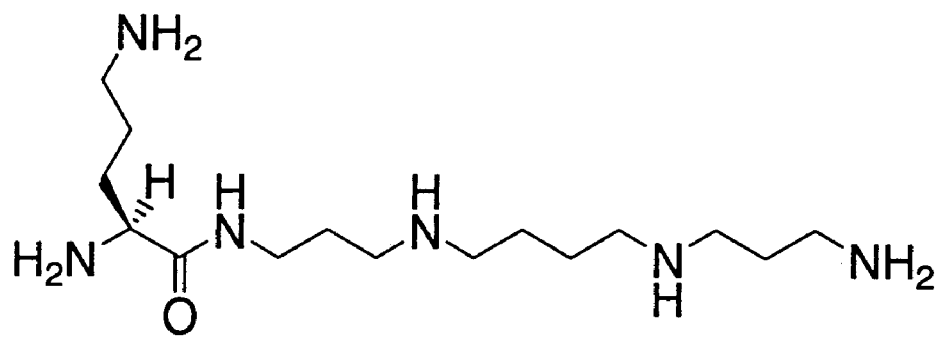
Figure 6:
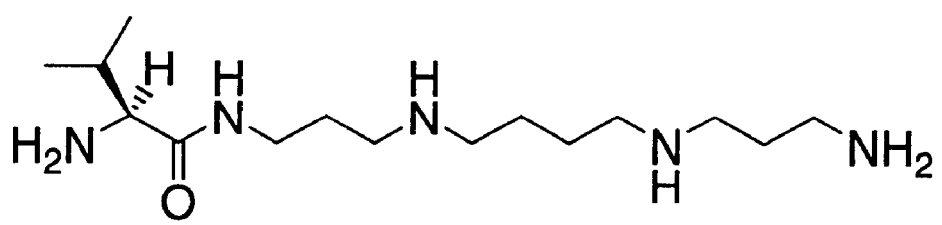
Figure 7:
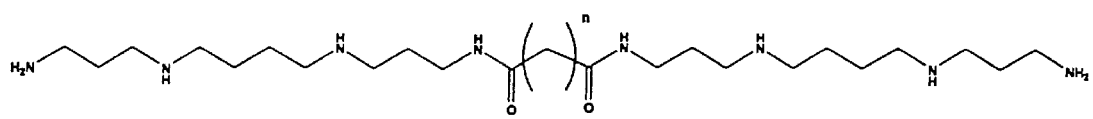
FIG. 7 shows the general structure of bis-amide dimers of spermine linked by an aliphatic or aromatic di-acid chain.
Figure 7:
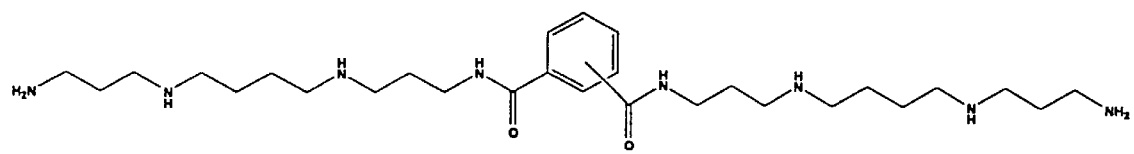

Polyamines may be protected by methods well known in the art. For example, spermine (3 equivalents or "eq") is monoprotected with di-tert-butyldicarbonate (1 eq) which is slowly added over a 1.5 hour time frame to a solution of spermine in dioxane/water with NaOH (1 eq). See FIG. 5. After stirring for 24 hours, the solvent is evaporated and the compound purified over a Bio-Rex cation exchange column (45×2.5 cm).

Figure 3A:
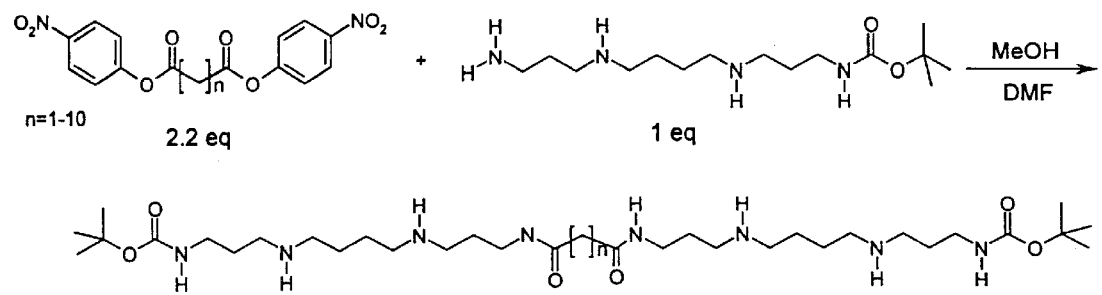
FIG. 3A shows a representative synthetic route for the preparation of bispolyamines of the invention. In this synthetic scheme, a bispolyamine containing two $N^1$-$^t$Boc-spermine polyamines is produced by linking the spermine derivatives with 4-nitrophenyl ester. The crude product from this reaction, after removal of the methanol (MeOH) and dimethyl formamide (DMF) solvents by evaporation and/or high vacuum, can be dissolved in either water or 50% MeOH/water for purification by column chromatography such as with a cation exchange column. Elution was with a gradient ranging from 0 to 1 or 2N $NH_4OH$.
Figure 3B:
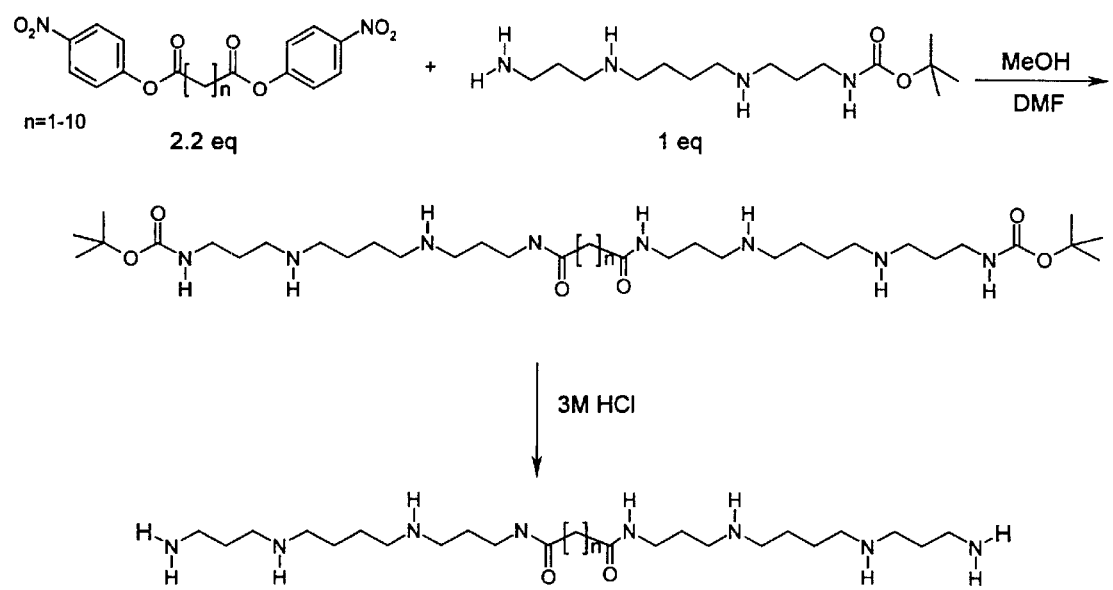
FIG. 3B shows the same representative synthetic route as FIG. 3A but with a further step of removing the $N^1$-$^t$Boc protecting group with 3M HCl.

Synthesis of bispolyamines may be by the reaction scheme shown in FIG. 3A, where p-nitrophenyl activated esters are reacted with protected spermines.

For example, to a flask of 2.2 equivalents of $N^1$-$^t$Boc-spermine in 10 mL methanol, 1 equivalent of 4-nitrophenyl ester dissolved in 5 mL DMF and 10 mL of MeOH was added drop by drop with stirring for three hours or overnight.

A second equivalent of the 4-nitrophenyl ester may be added as a solid and allow to stir for an additional 3 hours. The solvent was evaporated and the DMF removed under high vacuum. The crude product was originally redissolved in water and purified over a Bio-Rex cation exchange columnn (45×2.5 cm).

Optionally, 50% MeOH/water may be used as the solvent for improved solubility of the bispolyamine. The compounds were eluted with a gradient ranging from 0 through 1–2 N $NH_4OH$. The appropriate fractions were pooled and the solvent evaporated to produce the bispolymer.

$N^1$-$^t$Boc-spermine has been coupled to the eight paranitrophenyl esters shown in FIG. 18, including the succinyl (n=2) linked dispermine. I have purified six of these compounds using Bio-Rex cation exchange chromatography. The crude product is generally a mixture consisting of two spots when analyzed on thin layer chromatography (TLC). Both spots migrate higher than $N^1$-$^t$Boc-spermine with one generally migrating close to the solvent front and the other migrating somewhat higher than $N^1$-$^t$Boc-spermine but this varies with the p-nitrophenyl ester.

In general, this spot migrates higher as n increases in value. In the case where n=10 (dodecanedioyl derivative) the two spots migrate very close to each other near the solvent front. The purification of compounds with greater n values are generally eluted with a 0 to 1 or 1.5 N $NH_4OH$ gradient.

One exception, however, is the succinyl derivative which consists of four reaction products on TLC. This derivative was successfully purified using 50% MeOH/water instead of water as solvent.

For removal of the $N^1$-$^t$Boc protecting group, 5 mL of 3M HCl may be added to the above reaction conditions followed by stirring for one hour.

$^1$H and $^{13}$C NMR spectra for the t-boc protected bispolyamines have been completed except for ORI 1268 where only a $^1$H was completed. Likewise, $^1$H and $^{13}$C NMR spectra have also been obtained for the deprotected final products ORI 1236, 1288, 1289, 1290. Mass spec analysis has been completed for ORI 1288 and ORI 1290.

EXAMPLE V

Polyamine Transport Inhibition by Bispolyamines

Most of the spermine dimers that have been tested provided very good $K_i$ for transport inhibition with values under 75 nM. ORI 1236 was the most potent inhibitor with a $K_i$ of 22 nM. This value is comparable with the $K_i$ for ORI 1090 (between 10–22 nM for MDA cells). Only ORI 1275 had a $K_i$ that was above 100 nM ($K_i$=219 nM). The results were generally mirrored in the growth inhibition assay. All of the compounds where synergistic with DFMO with $IC_{50}$s of 10 μM or less. The most potent growth inhibitor was ORI 1288 followed by ORI 1286>1236>1289>1290>1275>1299.

Without being bound by theory, it appears that shorter linked spermine dimers are slightly more potent than the longer chained analogs. Because there was not a more dramatic difference in activity between the analogs, it is suggested that there is a fairly large degree of tolerance for the length of the aliphatic linker in a transporter's polyamine binding site. This also supports the finding that there is some leeway in linker length of PTI inhibitors such as 1202 and 1090. These bispolyamine molecules may interact in similar fashion with respect to the transporter as ORI 1202 and ORI 1090.

It was observed that ORI 1236 in combination with DFMO gave a maximum growth inhibition that was less than the ORI 1202/DFMO control. This suggested that ORI 1236 may partially rescue from polyamine depletion. Subsequently, ORI 1236 was found to partially rescue from DFMO. Almost all other bispolyamine compounds tested except for ORI 1287 gave a maximum growth inhibition that was less than the ORI 1202/DFMO control. ORI 1236 and 1290 have been re-tested and only ORI 1290 displayed rescue All references cited herein are hereby incorporated by reference in their entireties, whether previously specifically incorporated or not.

Having now fully described this invention, it will be appreciated by those skilled in the art that the same can be performed within a wide range of equivalent parameters, concentrations, and conditions without departing from the spirit and scope of the invention and without undue experimentation.

While this invention has been described in connection with specific embodiments thereof, it will be understood that it is capable of further modifications. This application is intended to cover any variations, uses, or adaptations of the invention following, in general, the principles of the invention and including such departures from the present disclosure as come within known or customary practice within the art to which the invention pertains and as may be applied to the essential features herein before set forth as follows in the scope of the appended claims.

What is claimed is:

1. A polyamine analog or derivative, that binds to a polyamine-binding site of a molecule and/or inhibits polyamine transport, said analog or derivative having the structure polyamine-linker-polyamine wherein said polyamine comprises spermine or the $N^{12}$-t-butyl carbamate of spermine and said linker comprises a 1–12 aliphatic carbon alkyl chain, an alicyclic or an aromatic moiety.

2. The analog or derivative according to claim 1 wherein said linker is a 1–12 aliphatic carbon alkyl chain.

3. The analog or derivative according to claim 1 wherein said linker is an aromatic moiety.

4. The analog or derivative according to claim 3 wherein said aromatic moiety is selected from a benzene ring and napthalene.

5. The analog or derivative according to claim 3 wherein said moiety is a benzene ring.

6. The analog or derivative according to claim 3 wherein said moiety is napthalene.

7. The analog or derivative according to claim 1 wherein each polyamine is spermine which is attached to said linker via the $N^1$ position.

8. The analog or derivative according to claim 7 wherein each spermine is attached to said linker via an amide linkage or a sulfonamide linkage.

9. The analog or derivative according to claim 8 wherein each spermine is attached to said linker via an amide linkage.

10. The analog or derivative according to claim 8 wherein each spermine is attached to said linker via a sulfonamide linkage.

11. The analog or derivative according to claim 1 wherein said polyamine is spermine with an amide linkage to a linker selected from 1,3-dimethyl-adamantylene, naphthalene, ethylene, propylene, butylene, pentylene, hexylene, heptylene, octylene, nonylene, and decylene.

12. The analog or derivative according to claim 1 wherein said polyamine is the $N^{12}$-t-butyl carbamate of spermine with an amide linkage to a linker selected from 1,3-dimethyl-adamantylene, naphthalene, ethylene, propylene, butylene, pentylene, hexylene, heptylene, octylene, nonylene, and decylene.

13. The analog or derivative according to claim 10 wherein said polyamine is spermine and said linker is naphthalene.

14. The analog or derivative according to claim 1 wherein said polyamine is a spermine comprising a protecting group at the $N^{12}$ position.

15. The analog or derivative according to claim 14 wherein said polyamine is the $N^{12}$-t-butyl carbamate of spermine with an amide linkage to a linker selected from ethylene, propylene, pentylene, hexylene, heptylene, octylene, and decylene.

16. A composition useful for treating a disease or condition in which the inhibition of polyamine transport is desirable, comprising an analog or derivative according to claim 1 and one or more pharmaceutically acceptable excipients.

17. A composition useful for treating a disease or condition in which the inhibition of polyamine transport and synthesis is desirable, comprising the composition of claim 16 and an inhibitor of polyamine synthesis.

18. A composition according to claim 17 wherein said inhibitor of polyamine synthesis is difluoromethylornithine (DFMO).

19. A composition according to claim 16, further comprising, in combination with said composition, one or more additional agents known to be useful for treating said disease or condition.

20. A composition according to claim 16 wherein said polyamine is spermine with an amide linkage to a linker selected from 1,3-dimethyl-adamantylene, naphthalene, ethylene, propylene, butylene, pentylene, hexylene, heptylene, octylene, nonylene, and decylene.

21. A composition according to claim 20 wherein said polyamine is spermine with a sulfonamide linkage to naphthalene.

22. A composition according to claim 20 wherein said polyamine is the $N^{12}$-t-butyl carbamate of spermine with an amide linkage to a linker selected from 1,3-dimethyl-adamantylene, naphthalene, ethylene, propylene, butylene, pentylene, hexylene, heptylene, octylene, nonylene, and decylene.

23. A method for treating a disease or a condition in a subject associated with undesired proliferation of cells and/or cell types and/or which is treatable by inhibition of polyamine transport, comprising administering to said subject an effective amount of an analog or derivative according to claim 1.

24. A method according to claim 23 wherein said undesired proliferation of cells and/or cell types is associated with cancer.

25. A method comprising administering to said subject an effective amount of an analog or derivative according to claim 1 such that an anti-diarrheal effect is produced in said subject.

26. A method for treating a disease or a condition in a subject associated with undesired proliferation of cells and/or cell types and/or which is treatable by inhibition of polyamine transport and synthesis, comprising administering to said subject an effective amount of an analog or derivative according to claim 1, and an inhibitor of polyamine synthesis.

27. A method according to claim 26 wherein said inhibitor of polyamine synthesis is difluoromethylornithine (DFMO).

28. A method according to claim 23 wherein said undesired proliferation of cells an or cell types is associated with an autoimmune disease.

* * * * *